US008471072B2

(12) United States Patent
Suppes et al.

(10) Patent No.: US 8,471,072 B2

(45) Date of Patent: Jun. 25, 2013

(54) SOY-BASED POLYOLS

(75) Inventors: Galen Suppes, Columbia, MO (US); Zuleica Lozada, Columbia, MO (US); Arnold Lubguban, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 426 days.

(21) Appl. No.: 12/698,652

(22) Filed: Feb. 2, 2010

(65) Prior Publication Data

US 2010/0190951 A1 Jul. 29, 2010

Related U.S. Application Data

(63) Continuation-in-part of application No. 11/746,445, filed on May 9, 2007, now Pat. No. 7,696,370.

(60) Provisional application No. 60/799,061, filed on May 9, 2006, provisional application No. 60/857,438, filed on Nov. 7, 2006, provisional application No. 61/206,717, filed on Feb. 2, 2009.

(51) Int. Cl.
*C07C 29/10* (2006.01)

(52) U.S. Cl.
USPC ................. 568/700; 554/24; 554/25; 554/26; 549/512

(58) Field of Classification Search
None
See application file for complete search history.

(56) References Cited

U.S. PATENT DOCUMENTS

| | | | | |
|---|---|---|---|---|
| 2,611,788 | A | 9/1952 | Bloch | |
| 3,355,306 | A * | 11/1967 | Krol | 106/122 |
| 3,827,993 | A | 8/1974 | Cunningham et al. | |
| 4,530,938 | A | 7/1985 | White | |
| 4,717,738 | A | 1/1988 | Fukuda et al. | |
| 4,831,076 | A | 5/1989 | Lidy et al. | |
| 5,374,446 | A | 12/1994 | Ferenz et al. | |
| 5,482,980 | A | 1/1996 | Pcolindky | |
| 6,057,375 | A | 5/2000 | Wollenweber et al. | |
| 6,258,869 | B1 | 7/2001 | Shah et al. | |
| 6,399,698 | B1 | 6/2002 | Petrovic et al. | |
| 6,476,244 | B2 | 11/2002 | Mahlum | |
| 6,686,435 | B1 | 2/2004 | Petrovic et al. | |
| 6,759,542 | B2 | 7/2004 | Mahlum | |
| 7,691,914 | B2 * | 4/2010 | Abraham et al. | 521/172 |
| 2002/0095007 | A1 | 7/2002 | Larock et al. | |
| 2006/0041156 | A1 | 2/2006 | Casper et al. | |
| 2006/0041157 | A1 | 2/2006 | Petrovic et al. | |
| 2006/0178456 | A1 | 8/2006 | Seats et al. | |
| 2006/0264524 | A1 | 11/2006 | Abraham et al. | |

(Continued)

FOREIGN PATENT DOCUMENTS

| | | | |
|---|---|---|---|
| WO | 2007127379 | A1 | 11/2007 |
| WO | 2008063595 | A2 | 5/2008 |
| WO | 2009105400 | A1 | 8/2009 |

OTHER PUBLICATIONS

EPOXOL 7-4 Specifications, 2012, American Chemical Service, Inc., 1 page.*

(Continued)

*Primary Examiner* — Yate K Cutliff
(74) *Attorney, Agent, or Firm* — Polsinelli PC

(57) ABSTRACT

The invention provides processes for preparing soy-based oligomeric polyols or substituted oligomeric polyols, as well as urethane bioelasteromers comprising the oligomeric polyols or substituted oligomeric polyols.

10 Claims, 23 Drawing Sheets
(2 of 23 Drawing Sheet(s) Filed in Color)

Epoxide compound
Poly-alcohol compound
Ether compound
Alkene compound
Poly Ether alcohol

U.S. PATENT DOCUMENTS

2007/0265459 A1 11/2007 Suppes et al.
2008/0281071 A1 11/2008 Ionescu et al.
2010/0036177 A1* 2/2010 Ward ............................ 568/865

OTHER PUBLICATIONS

Shpan'ko I.V. et al., Effrect f the structues of arylsulfonic acids on the kinetics of oxirane ring opening in 4-nirtophenyloxirane, 2000, Theoretical and Experimental Chemistry, vol. 36, No. 6, pp. 338-341.*

Dasari et al., "Low-pressure hydrogenolysis of glycerol to propylene glycol", Applied Catalysis A:General, 2005, pp. 225-231, vol. 281, Nos. 1-2.

International Search Report for PCT/US07/83694, dated Mar. 27, 2008; 3 pages.

Lee et al., "Modification of soybean oil for intermediates by epoxidation, alcoholysis and amidation", The Korean Journal of Chemical Engineering, 2008, pp. 474-482; vol. 25, No. 3.

Lubguban et al., "Functionalization via Glycerol Transesterification of Polymerized Soybean Oil", Journal of Applied Polymer Science, 2009, pp. 19-27, vol. 112.

Yerrakondreddygari; "Polyols made from Vegetable Oil and Their Applications", a thesis presented to the faculty of the Graduate School at University of Missouri—Colombia, 2005; Made available to the public Mar. 22, 2007.

Written Opinion and International Search Report for PCT/US11/23275, dated Jun. 13, 2011, 11 pages.

Notice of Allowance from U.S. Appl. No. 12/713,342 dated Dec. 6, 2011, 10 pages.

* cited by examiner

ESBO o-Phosphoric acid

Phosphate ester

Phosphate ester polymeric MDI

Bioelestomer

SOY-BASED POLYOLS

CROSS REFERENCE TO RELATED APPLICATIONS

The application is a continuation-in-part of U.S. patent application Ser. No. 11/746,445 filed May 9, 2007, which claims the benefit of U.S. Provisional Application No. 60/799,061 filed May 9, 2006 and U.S. Provisional Application No. 60/857,438 filed Nov. 7, 2006, each of which is incorporated by reference in its entirety. This application also claims priority to U.S. Provisional Application No. 61/206,717 filed Feb. 2, 2009, which is hereby incorporated by reference in its entirety.

GOVERNMENTAL RIGHTS

The present invention was made, at least in part, with support from the U.S. Department of Energy Agreement Numbers DE-FG36-02GO12026 and GO12026-227. Accordingly, the United States Government has certain rights in the invention.

FIELD OF INVENTION

This invention relates soy-based derived polyols and use of these polyols in urethane formulations. More specifically, this invention relates to processes for preparing oligomeric polyols or substituted oligomeric polyols, as well as the urethane formulations comprising the oligomeric polyols or substituted oligomeric polyols.

BACKGROUND

Soy-based polyols are of interest because they are produced from renewable and domestic feed stocks rather than non-renewable petroleum-based feed stocks. Another advantage of soy-based polyols is the low cost of the feed stocks.

A variety of processes have been employed to produce polyols. Blown vegetable oils are an example of a soy-based polyol. U.S. Pat. Nos. 6,476,244 and 6,759,542 describe methods of synthesizing blown vegetable oils, which include use of air blown through the vegetable oils at elevated temperatures to promote partial oxidation. U.S. Pat. No. 6,686,435 describes a method of making natural oil-based polyols consisting of reacting the epoxy moiety of an epoxidized natural oil with a hydroxyl moiety of an alcohol in the presence of 10% to 30% water. U.S. Pat. No. 6,258,869 is on a process for production of polyols by reacting an agricultural feed stock with a multi-functional alcohol in the presence of a tin catalyst. U.S. Pat. No. 5,482,980 describes a method of preparing a flexible foam by using an epoxidized soybean oil at 7 to 25 parts by weight per hundred parts polyol.

A need, therefore, exists in the art for a process to convert vegetable oils to polyols of higher molecular weight that is more efficient and economical than those described in the prior art.

SUMMARY OF THE INVENTION

The presently disclosed processes advance the art and overcome problems associated with the conversion of vegetable-derived triglycerides into polymers. Accordingly, the processes produce polyols with unique and improved properties.

One aspect of the invention provides a process for preparing an oligomeric polyol. The process comprises contacting a soy-based epoxidized triglyceride with a hydroxyl-containing reactant in the presence of an aromatic sulfonic acid.

Another aspect of the invention encompasses a urethane bioelastomer formulation comprising a phosphate ester-substituted polyol, wherein the formulation has a tensile strength at break of at least about 0.4 MPa.

Other aspects and features of the invention are described in more detail herein.

DESCRIPTION OF THE FIGURES

Reference To Color Figures

This application file contains at least one photograph executed in color. Copies of this patent application publication with color photographs will be provided by the Office upon request and payment of the necessary fee

DETAILED DESCRIPTION OF THE INVENTION

Figure 1:
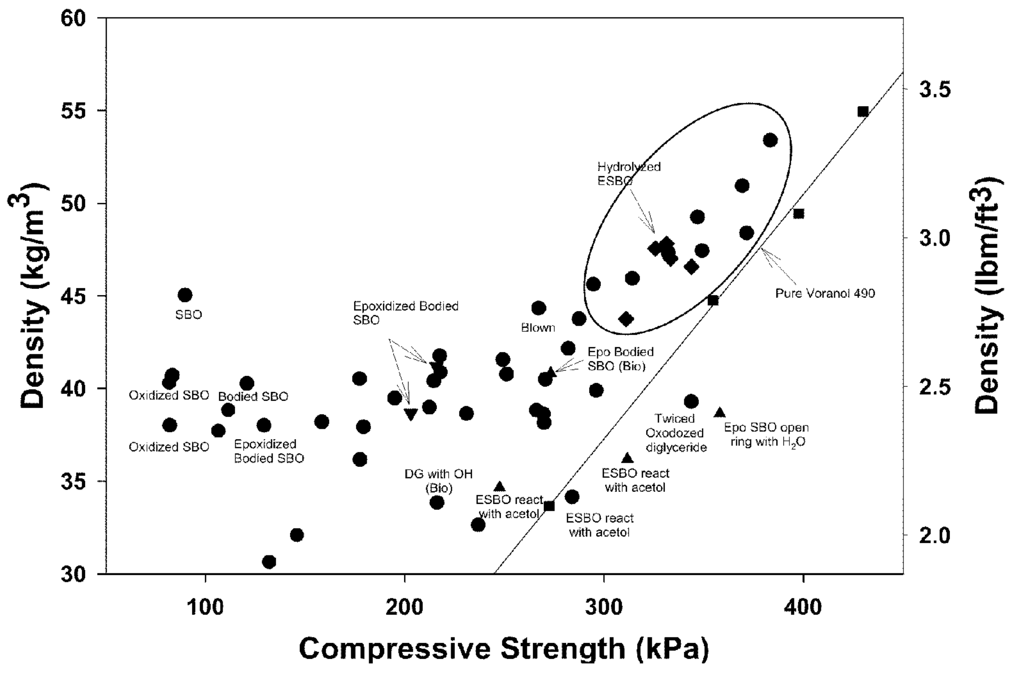
FIG. 1 presents a comparison of the performance of several soy-based formulations with a commercially available petroleum-based polyol, VORANOL® 490 (line). The formulations used 50% VORANOL® and 50% soy-based derivative in the B-side.

Provided herein are processes for preparing oligomeric polyols or substituted polyols from soy-based triglycerides. The soy-based polyols provided herein may be used as alternatives to petroleum-based polyols in urethane formulations. The oligomeric polyols substituted polyols formed by the processes disclosed herein may comprise epoxy groups, oxirane rings, keto groups, ether groups, substituted hydroxyl groups, phosphate ester-substituted groups, and/or other alcohol-substituted groups. Also provided herein are urethane bioelastomer formulations comprising the oligomeric polyols or substituted polyols disclosed herein, wherein the urethane bioelastomers have excellent tensile and thermal properties.

Process for Preparing Oligomeric Epoxidized Polyol

Provided herein is a process for preparing a soy-based oligomeric epoxidized polyol. The process comprises contacting a soy-based epoxidized triglyceride with a hydroxyl-containing reactant in the presence of an aromatic sulfonic acid. The aromatic sulfonic acid is an effective catalyst for promoting reaction of the hydroxyl groups of the hydroxyl-containing reactant with epoxy groups on the triglyceride to produce the oligomeric epoxidized polyol. Accordingly, the oligomeric polyol may be modified to contain targeted amounts of epoxy functionality, alcohol functionality, and oligomerization. Typically, the aromatic sulfonic acid remains in the polyol and/or the final urethane and can be detected by analytical means. Example 13 provides an illustrative example of this process for preparing oligomeric epoxidized polyols.

Epoxidized triglyceride. Typically, the soy-based triglycerides used herein comprise unsaturated fatty acids. The soy-based triglyceride may be epoxidized using procedures well known in the art. For example, the triglyceride may be contacted with formic acid and hydrogen peroxide. The molar ratio of triglyceride to formic acid may range from about 1:0.1 to about 1:1.0. In some embodiments, the molar ratio of triglyceride to formic acid may range 1:0.2 to about 1:0.6. In preferred embodiment, molar ratio of triglyceride to formic acid may be about 1:0.4. The molar ratio of the triglyceride to hydrogen peroxide may range from about 1:0.1 to about 1:1.5 In some embodiments, the molar ratio of triglyceride to hydrogen peroxide may range 1:0.5 to about 1:0.7. In preferred embodiment, molar ratio of triglyceride to hydrogen peroxide may be about 1:0.7. The temperature of the epoxidation reaction may range from about 20° C. to about 100° C., preferably about 40° C. Typically, the epoxidation reaction is conducted in the absence of a solvent.

The epoxidized triglyceride may be fully epoxidized, wherein 100% of the double bonds of the molecule comprise an oxirane ring. Alternatively, the epoxidized triglyceride may be partially epoxidized, wherein at least 20% of the double bonds of the molecule comprise an oxirane ring. Thus, a partially epoxidized triglyceride may comprise about 20%, 20-25%, 25-30%, 30-35%, 35-40%, 45-50%, 50-60%, 60-70%, 70-80%, 80-90%, or 90-99% of epoxidized double bonds. In other embodiments, the epoxidized triglyceride may comprise about 60-90% of epoxidized double bonds.

The epoxy content of the fully or partially epoxidized triglyceride may vary. In general, the epoxy content will range from about 2% to about 10%. In various embodiment, the epoxy content may be from 2-3%, 3-4%, 4-5%, 5-6%, 6-7%, 7-8%, or 8-10%. In one embodiment, the epoxy content of the fully or partially epoxidized triglyceride may range from about 5% to about 6.5%.

The viscosity of the fully or partially epoxidized triglyceride can and will vary. Typically, the viscosity of the epoxidized triglyceride may range from about 500 to about 10,000 cP at 22° C. In one embodiment, the viscosity of the epoxidized triglyceride may range from about 3,000 to about 6,000 cP at 22° C. In another embodiment, the viscosity of the epoxidized triglyceride may range from about 3,500 to about 4,500 cP at 22° C.

Hydroxyl-containing reactant. The hydroxyl-containing reactant comprises at least one hydroxyl (or alcohol) group and preferably more than one hydroxyl (or alcohol) group. Preferred reagents include difunctional (two moiety) compounds capable of reacting with epoxy moieties. Known good performers for this reaction are alcohol moieties, epoxy moieties, and other moieties known to react with epoxy moieties. Generally, the hydroxyl-containing reactant is chosen from alcohols and diacids.

In some embodiments, the hydroxyl-containing reactant may be a difunctional alcohol, e.g., a diol. Preferred diols include ethylene glycol, propylene glycol, diethylene glycol, trithethylene glycol, and tetraethylene glycol. In one preferred embodiment, the diol is ethylene glycol. In other embodiments, the hydroxyl-containing reactant may be a mono functional alcohol. In particular, the alcohol may be a C1-C4 alcohol such as methanol, ethanol, n-propanol, isopropanol, n-butanol, isobutanol, s-butanol, t-butanol, and the like.

The molar ratio of the epoxidized triglyceride to the hydroxyl-containing reactant can and will vary. Generally, the molar ratio of the epoxidized triglyceride to the hydroxyl-containing reactant may range from about 1:0.1 to about 1:3. In some embodiments, the molar ratio of the epoxidized triglyceride to the hydroxyl-containing reactant may range from about 1:0.25 to about 1:2. In further embodiments, the molar ratio of the epoxidized triglyceride to the hydroxyl-containing reactant may range from about 1:0.4 to about 1:0.8. In one embodiment, the molar ratio of the epoxidized triglyceride to the hydroxyl-containing reactant may be about 1:0.64.

Aromatic sulfonic acid. Non-limiting examples of suitable aromatic sulfonic acids include p-toluenesulfonic acid and benzenesulfonic acid. In a preferred embodiment, the aromatic sulfonic acids is p-toluenesulfonic acid.

The molar ratio of the epoxidized triglyceride to the aromatic sulfonic acid may range from about 1:0.0005 to about 1:0.2. In some embodiments, the molar ratio of the epoxidized triglyceride to the aromatic sulfonic acid may range from about 1:0.01 to about 1:0.1. In a preferred embodiment, the molar ratio of the epoxidized triglyceride and the aromatic sulfonic acid may range from about 1:0.02 to about 1:0.05. In one embodiment, the molar ratio of the epoxidized triglyceride and the aromatic sulfonic acid may be about 1:0.03.

Reaction conditions. Contact between the epoxidized triglyceride, the hydroxyl-containing reactant, and the aromatic sulfonic acid is typically conducted at a temperature that ranges from about 100° C. to about 240° C. In some embodiments, the reaction temperature may range from about 120° C. to about 200° C. In preferred embodiments, contact between the epoxidized triglyceride, the hydroxyl-containing reactant, and the aromatic sulfonic acid may occur at a temperature ranging from about 130° C. to about 160° C.

The duration of the reaction can and will vary. In general, the reaction may proceed from about 1 minute to about 24 hours. In some embodiments, the duration of the reaction may range from about 1 hour to about 12 hours. In preferred embodiments, the reaction may proceed for about 3 hours to about 10 hours.

Preferred reactants and reaction conditions are presented below:

| | Preferred | More-Preferred | Most-Preferred |
|---|---|---|---|
| Percent Epoxide in PESBO | 0.2-7 | 1-5 | 1.5-4.5 |
| Co-Reagent | Known Reagent with Epoxy | Diol or diacid | Ethylene Glycol |
| Catalyst | | | TSA |
| Molar Ratio of PESBO:Di-Functional Co-Reagent | 0.1-3 | 0.25-2- | 0.4-0.8 |
| Molar Ratio of PESBO:Catalyst | 0.005-0.2 | 0.01-0.1 | 0.02-0.05 |
| Temperature | 100-240° C. | 120-200° C. | 130-160° C. |
| Reaction Time at Temperature | 0.02-24 hr | 1-12-hr | 3-10 hr |

Oligomeric polyols. The oligomeric epoxidized polyol prepared by this process may have the following properties:

| | Preferred | More-Preferred | Most-Preferred |
|---|---|---|---|
| Avg. MW | 1,000-10,000 | 1,200-4,000 | 1,500-3,500 |
| Avg. OH Functionality per molecule | 1-10 | 1.5-6 | 2-5 |
| Avg. Epoxy Functionality per molecule | 0.2-10 | 0.5-6 | 1-4 |
| (OH + Epoxy) Equ. Wt | 200-1500 | 300-1100 | 400-1000 |
| OH-Equ. Wt | 200-3000 | 400-2000 | 500-1500 |
| Epoxide-Equ. Wt | 200-4000 | 400-3000 | 500-2000 |
| Viscosity (cP) | 100-20,000 | 400-8,000 | 800-4,000 |
| Acid Number | 0-20 | 0-5 | 0-2 |
| % Epoxy | 0-2% | 0.2-1.5% | 0.4-01.2% |
| Iodine Number | 0-80 | 15-50 | 25-45- |
| Low Concentration (mass fraction) Components in Polyol and implicitly in isocyanate in more-diluted mass fraction | | | |
| Phosphoric Acid | 0.002-4 | 0.1-3 | 0.5-2.5 |
| Toluene Sulfonic Acid (TSA) | 0.002-4 | 0.1-3 | 0.3-1.5 |
| Other Oligomerizing Agent | 0.002-4 | 0.1-3 | 0.3-1.5 |

The oligomeric epoxidized polyol formed by the process disclosed herein has a substantially increased hydroxyl value and reduced acid number as compared to that of the starting epoxidized triglyceride. In general, hydroxyl value of the oligomeric polyol is at least about 100 mg KOH/g. The viscosity of the oligomeric epoxidized polyol is also substantially increased, as detailed in the table above. Preferably, the oligomeric epoxidized polyol may have a viscosity of at least about 500 cP at 22° C.

Single Pot Chemistry

The preferred "single pot" approach to synthesizing soy-based oligomeric epoxidized polyols includes the step of solvent-free epoxidation. The term "single pot" indicates that it may be conducted in a vessel through multiple steps, but does not indicate that the preferred method is in a single vessel as a semi-batch process. Methods known in the art are available to scale-up laboratory procedures to a range of possible production scale processes.

Synthesis reactions are preferably at temperatures where increased acidity is not created from decomposition (less than 4 acidity without treatment). The steps in this approach include: 1) solvent-free epoxidation of an unsaturated triglyceride at a preferred temperature below 120° C., more preferably between 15 and 80° C. and most preferably between 25 and 60° C. with hydrogen peroxide and an acid like formic acid, 2) removal of water from the epoxidized triglyceride with the preferred water-removal means being vacuum flash separation, and 3) polymerization by adding a co-monomer such as a diol or diacid. The preferred reactions conditions are detailed above.

Process for Preparing a Phosphate Ester-Substituted Polyol

A further aspect provided herein encompasses a process for preparing a phosphate ester-substituted soy-based polyol. The process comprises contacting an epoxidized triglyceride (see above) or an oligomeric epoxidized polyol (see above) with o-phosphoric acid ($H_3PO_4$). Without being bound to any specific theory it is believed that phosphoric acid is an effective reagent for binding epoxy groups on the epoxidized triglyceride or the oligomeric epoxidized polyol to create an phosphate ester-substituted polyol. The resultant phosphate ester-substituted polyol may be modified to contain targeted amounts of epoxy functionality, alcohol functionality, and oligomerization. The phosphate ester-substituted polyol may be further reacted with isocyanates or substitutes thereof to form a urethane formulation. Typically, the acid remains in the polyol and/or the final urethane formulation, wherein the acid may be detected by analytical means. Example 13 illustrates the preparation of phosphate ester-substituted polyols.

The oligomeric phosphate ester-substituted polyol is prepared by contacting a soy-based epoxidized triglyceride or an oligomeric epoxidized polyol with o-phosphoric acid. In some embodiments, the epoxidized triglyceride or oligomeric epoxidized polyol may be contacted with o-phosphoric acid prior to formation of a urethane bioelastomer formulation (see below). In other embodiments, the epoxidized triglyceride or oligomeric epoxidized polyol may be contacted with o-phosphoric acid simultaneously with formation of a urethane bioelastomer.

The ratio of the epoxidized triglyceride or oligomeric epoxidized polyol to o-phosphoric acid may range from about 1:0.2% by weight to about 1:5% by weight. In some embodiments, the ratio of the epoxidized triglyceride or oligomeric epoxidized polyol to o-phosphoric acid may range from about 1:0.4% by weight to about 1:3% by weight. In preferred embodiments, the ratio of the epoxidized triglyceride oligomeric epoxidized polyol to o-phosphoric acid may range from about 1:0.5% by weight to about 1:1.5% by weight.

Typically, the reaction is conducted in the absence of any additional solvent. The temperature of the reaction may range from about 15° C. to about 150° C. In various embodiments, the reaction temperature may range from about 15° C. to about 100° C. In preferred embodiments, the temperature of the reaction may range from about 20° C. to about 60° C. In one preferred embodiment, the reaction may be conducted at room temperature.

Preferred reactants and reaction conditions are presented below:

| | Preferred | More-Preferred | Most-Preferred |
|---|---|---|---|
| Percent Epoxide in partially epoxidized soybean oil (PESBO) | 0.2-7 | 1-5 | 1.5-4.5 |
| Agent | Known Reagent with Epoxy | Acid or isocyanate | Phosphoric Acid |
| Mass Ratio of Agent to Epoxy molecule | 0.2-5 | 0.4-3 | 0.5-1.5 |
| Temperature | 15-150° C. | 20-100° C. | 25-60° C. |
| Reaction Time at Temperature | 0.01-8 hr | 0.1-2-hr | 0.2-1 hr |

The phosphate ester-substituted polyol has a reduced oxirane oxygen content relative to that of the starting epoxidized triglyceride or oligomeric epoxidized polyol (see Table 32 in Examples). Additionally, the phosphate ester-substituted polyol generally has a viscosity of greater than about 500 cP at 22° C. (see Table 32 in Examples).

Urethane Bioelastomer Formulations

Also provided herein are urethane bioelastomer formulations comprising phosphate ester-substituted polyols. The urethane bioelastomer formulations disclosed herein have high tensile strengths (at break) of at least about 0.4 MPa. The urethane bioelastomer formulations are prepared by contacting the phosphate ester-substituted polyol prepared as disclosed herein with isocyanate monomers or substitutes thereof (see Example 13). Suitable isocyanate monomers include those known in the art, as well as organic molecules (such as, e.g., ethylene glycol or phosphoric acid) that may react with the reactive groups of the phosphate ester-substituted polyol. Methods for preparing urethane polymers are known to those of skill in the art, as are suitable ratios of reactants.

Because the phosphate ester-substituted polyols prepared as described herein have reduced oxirane oxygen contents, lower amounts the isocyanate monomer or substitute thereof may be used to form the urethane bioelastomer formulation than typically are used in urethane formulations that do not comprise phosphate ester-substituted polyols. For example, at least 10% less isocyanate may be used to prepare urethane bioelastomer formulations comprising phosphate ester-substituted polyols. In other embodiments, at least 20%, 30%, or 40% less isocyanate may be used to prepare urethane bioelastomer formulations comprising phosphate ester-substituted polyols.

The urethane bioelastomers prepared with the phosphate ester-substituted polyol (which are also called acid-catalyzed polyols) tend to be highly crosslinked. Accordingly, these urethane bioelastomer formulations have a low percentage of extractable oils. The percentage of extractable oil content may be less than 10%, or more preferably less than about 5% (see, e.g., Table 30 in the Examples and FIG. 17). Moreover, the urethane bioelastomers comprising phosphate ester-substituted polyols tend to have high tensile strength and high thermal properties (see, e.g., Table 33 in the Examples)

A comparison of non-oligomeric soy-based polyols with functionality of 4 (NOSBP-4) to oligomeric polyols is presented in the following table. PAPI™ 27 (available from the Dow Chemical Company) is a 2-functional isocyanate capable of joining two NOSBP-4 molecules (or join oligomers of the NOSBP-4 or join the oligomers to the non-oligomers).

| | Approximate Values | | |
|---|---|---|---|
| Molecule | Functionality | MW | OH Equ. Wt. |
| 1. NOSBP-4 | 4 | 980 | 245 |
| 2. NOSBP-4 joined by One PAPI 27 | 6 | 2228 | 371 |
| 3. NOSBP-4 joined by Two PAPI 27 | 8 | 4284 | 536 |
| 4. NOSBP-3 | 3 | 980 | 327 |
| 5. NOSBP-3 joined by One PAPI 27 | 4 | 2228 | 557 |
| 6. NOSBP-3 joined by Two PAPI 27 | 5 | 4284 | 857 |

PAPI 27 has an isocyanate equivalent weight of 134 (http://www.adhesivesmag.com/directories/539/2007/294455/isocyanates-0807.pdf). This table presented above illustrates how B-side surrogates may be prepared by connecting NOSBP molecules. Even though the example is with an isocyanate, because such complexes are known to be vital to urethane polymers, the approach is not limited to isocyanate co-reagents. This invention comprises an embodiment in which a B-side oligomer is prepared with reactants alternative to PAPI 27 (such as ethylene glycol or phosphoric acid) to form products that are similar to products 2, 3, 5, and 6 of this table. The net impact is that when this oligomeric polyol is used in a final urethane formulation application (relative to the non-oligomeric product) the amount of isocyanate is reduced thereby meeting the goal of reducing isocyanate loading.

Bodied Oil with Monomer Addition of Moiety

A preferred embodiment of this invention is bodied soybean oil with which acetol is reacted to attach hydroxyl moieties. In the broader sense, this embodiment is a process for converting an unsaturated molecule containing at least six carbon atoms to an alcohol, comprising the steps of: bodying the unsaturated molecule at temperature between 150° to 350° C. for less than 48 hours until the viscosity of the bodied product is at least 20% greater than the viscosity of the unsaturated molecule, and reacting carbon-carbon π-bonds remaining in the bodied product with a monomer containing an oxygen containing moiety. The bodying is performed in the absence of diatomic oxygen.

The unsaturated molecule is preferably an unsaturated triglyceride. The monomer containing an oxygen-containing moiety is preferably at least one monomer selected from the group consisting of acetol, allyl alcohol, glycerol, glycols, epichlorohydrin, and acrolein.

Acetol may be reacted at temperatures between about 180° to about 250° C. Preferably, the reaction conditions include temperatures between about 195° to about 225° C. for 0.2 to 6 hours at a pressure/volume to keep greater than about 80% of the acetol in a liquid phase during the reaction. No catalyst is generally necessary. Lower temperatures, such as down to about 140° C., provide the reaction with acetol at the expense of longer reaction times. Use of heterogeneous catalysts is an option. It is to be noted that while acetol reacts under these conditions, bodying of soybean oil with or without simultaneous reaction with acetol is preferably at temperatures between about 160° to about 280° C., and more preferably, between about 200° to about 240° C.

The pressure of the reaction is preferably maintained above the bubble point of the reaction mixture, which is largely determined by the concentration of the most volatile component. Typically, the monomers are present at a concentration between about 5% and about 20%. Pressures of 3 to 30 bars are generally adequate to maintain these monomer concentrations in solution.

A semibatch process is preferred to lessen vapor pressures. Generally, all glyceride reagents are loaded at zero reaction time and the monomers are added stepwise or continuously during reaction. Such an approach also applies to batch and continuous (such as a flow reactor designed to approach plug flow behavior) processes.

The bodying reaction may also be performed in the presence of a cross-linking monomer. Preferably, the cross-linking monomer is at least one cross-linking monomer selected from the group consisting of dicyclopentadiene and divinylbenzene. The monomer addition step may be performed after the bodying step, or in the same reactor and at the same time as the bodying step. The monomer and the cross-linker are preferably present at concentrations between about 2% and about 20%, and more preferably, between about 8% and about 16%.

Allyl alcohol may be reacted with the bodied product at a temperature between about 240° to about 340° C. More preferred reaction conditions for reaction with allyl alcohol include a reaction temperature between about 250° to about 310° C.

Glycerol and glycols such as ethylene glycol react with bodied ester products to attach hydroxyl moieties, without being bound by any particular theory or mechanism, by at least two mechanisms. First, carboxylic acid moieties on the bodied product may esterify with the hydroxyl groups on the glycerol or glycol. Second, ester moieties in the bodied product may transesterify with the alcohols. In the presence of base catalysts, transesterification may be performed at ambient temperatures, but more preferably at temperatures above about 50° C. Preferred reaction temperatures for glycerol and glycol addition are between about 50° and about 340° C. At temperatures above 230° C., glycerol may undergo side-reactions, and so, preferred temperatures are below about 230° C. The more-preferred temperatures are between about 150° and about 230° C. because in this temperature range the reaction proceeds without catalysts. Reaction times from 30 minutes to 3 hours are typical for these esterification and transesterification reactions, and these times can and will vary based on mixing, viscosity of mixture, and the alcohol.

Glycerol and glycols may react with the unsaturated molecule containing at least six carbon atoms at the same time the bodying reaction occurs or after the bodying reaction. Reaction after the bodying reaction may be conducted at lower temperatures with advantages associated with reduced degradation of the glycerol and glycols. Mixing may be utilized to promote the esterifications and transesterifications since glycerol and glycols tend to form immiscible phases with soybean oil and the bodied products. Use of heterogeneous catalysts is preferred for the transesterification reactions. Suitable catalysts include solid acid catalysts, solid basic catalysts, and nickel-containing catalysts.

Preferably, the bodied product with the attached oxygen-containing moiety is formed under process conditions that result in an acid number less than 30 and a hydroxyl number greater than 20. Excess acidity (i.e., greater than about 10) is preferably neutralized as described in the section entitled Epoxy Neutralization of Residual Acidity.

Bodying and monomer addition reactions may be enhanced with catalysts. Preferably, the catalyst is at least one catalyst from the anthracene derivatives group including anthraquinone (i.e., 9,10-dioxoanthracene) and other organic catalysts having at least one ketone moiety and at least one carbon-carbon π-bond. The catalyst is preferably a solid at temperatures below about 100° C. The catalyst may be present at a concentration between about 0% and about 10% (wt), and preferably between, about 1% and about 5%. The catalyst is preferably a solid at temperatures less than about 100° C., such that it may be readily filtered as a solid from the liquid bodied product for recycling.

The bodied product with the attached oxygen-containing moiety may be further reacted with an isocyanate to form a urethane polymer.

Temperatures higher than about 350° C. may be used to produce bodied soybean oil prior to addition of monomers. For example, an iodine number of 105 was obtained in a flow reactor at 370° C. feed with refined soybean oil with a residence time of 82 minutes; however, the acid number was 33. By comparison, an iodine number of 101 was obtained in a flow reactor at 350° C. feed with refined soybean oil with a residence time of 93 minutes with an acid number of 22. Generally speaking, higher temperatures lead to greater acidity and poorer product. Temperatures up to about 390° C. will work to produce bodied soybean oil, but the oil is not as good of quality as that produced at lower temperatures.

Epoxy Neutralization of Residual Acidity

This product, or one of many products of these embodiments having an acidity greater than 10, may be reacted with an epoxy-containing molecule to reduce the acid number. A product having an attached oxygen-containing moiety and an acid number greater than 20 is preferably reacted with an epoxy-containing molecule to reduce the acid number to a value less than 15. The epoxy-containing molecule is preferably epoxy soybean oil (i.e., epoxidized soybean oil, ESBO), and the reaction with epoxy soybean oil is preferably at a temperature between 140° and 190° C. without any additional catalyst. Typically, the epoxy soybean oil is applied at concentrations between about 1% and about 20% (wt). It has been shown that 20% works to neutralize an acid number of 50. The reaction time is preferably between about 2 and 17 hours, with times less than about 9 hours being desirable. The more preferred reaction conditions are 170° C. for 6 to 8 hours. The use of ESBO may lead to cross-linking, increased molecular weights of the polyol, and higher viscosities. Other epoxy compounds such as butylene oxide, propylene oxide, and ethylene oxide will neutralize the acid without the crosslinking and without significant increases in viscosity.

Partially Hydrolyzed Bodied Soybean Oil

An alternative embodiment of this invention is a B-side monomer of a urethane formulation prepared by partially hydrolyzing bodied soybean oil. In the broader sense, this embodiment is a process for synthesizing a B-side monomer of a urethane formulation comprised of the following steps: bodying an unsaturated glyceride to form a bodied glyceride, hydrolyzing some of the ester bonds of the bodied glyceride to form hydroxyl moieties on the glyceride and a free fatty acid, and separating the free fatty acid from the B-side monomer containing the hydroxyl moieties. Water is typically needed to promote hydrolysis, preferably from about 0.5% to about 10%, and most preferably, about 5%. A surfactant may be used since it promotes faster hydrolysis.

The hydrolysis may be a selective hydrolysis performed in a manner to selectively remove saturated fatty acids from the glyceride. Preferably, the hydrolysis is a selective hydrolysis performed by an enzymatic reaction at a temperature between about 30° and 50° C. in a phosphate buffer solution in a manner to selectively remove saturated fatty acids from the glyceride. Preferably, the partially hydrolyzed bodied glyceride has a hydroxyl number greater than 20 and is reacted with an epoxy-containing molecule to reduce the acid number. Typically, the partially hydrolyzed bodied glyceride has an acid number greater than 10 and a hydroxyl number greater than 20 and is reacted with an epoxy-containing molecule to reduce the acid number. Longer hydrolysis times may lead to greater acidity and hydroxyl numbers—these times are highly dependent on the enzyme and state (i.e., free versus immobilized) of the enzyme. The preferred means to handle high acidity is through neutralization with epoxy as described earlier in the section entitled Epoxy Neutralization of Residual Acidity.

Hydrolysis may be effectively performed using a packed-bed of immobilized enzyme. Enzyme loading may be such that 10 minutes of flow creates a mass of bodied product equal to the mass of immobilized enzyme when the bodied product reached 15% hydrolysis. The enzyme may be a lipase from *Burkholderia cepacia*. Free enzyme concentrations are typically less than about 0.5%, with lower loadings having slower reaction times. When performing the reaction in a stirred tank, typical reaction times may range from about 1 hour to about 48 hours.

This embodiment includes the steps of bodying and reacting with a monomer containing an oxygen-containing moiety to produce a B-side molecule capable of reacting with A-side monomers to form a polyurethane. In the broader sense, the B-side molecule is a hydroxyl-functional molecule. The preferred hydroxyl-functional molecule has the following properties: an average of at least 1.5 oxygen ester bonds per molecule but less than 8 oxygen ester bonds per molecule, a viscosity between 500 and 12,000 centipoise at 25° C. (more preferably between 500 and 4,000 centipoise), reactivity with Karl-Fischer reagent indicating a hydroxyl number between 30 and 200 (more preferably between 40 and 150), and a chemical analysis spectrum indicating the presence of six-carbon ring moieties indicating a Diels-Alder formation mechanism. Preferably, an average of between 0.5 and 5 six-carbon ring moieties consistent with a Diels-Alder reaction product are contained on the hydroxyl-functional molecule. The average molecular weight generally is greater than about 500 but less than about 5,000. In the case of glycerolysis products, the upper end of the hydroxyl number is up to about 500. In the case of products formed from the bodying of epoxy containing intermediates, the products may contain greater than an average of 0.5 ether bonds per molecule but less than 8 ether bonds per molecule. In some instances, a viscosity as low as 100 may have utility.

Vegetable Oil with Monomer Addition of Moiety

An alternative embodiment of this invention is soybean oil with which acetol is reacted to attach hydroxyl moieties. In the broader sense, this embodiment is a process for converting an unsaturated molecule containing at least six carbon atoms to an alcohol, comprising the steps of: reacting carbon-carbon $\pi$-bonds of the unsaturated molecule with a monomer containing an oxygen-containing moiety at a temperature between about 150° to about 350° C. for less than 48 hours to form an oxygen-containing product.

The unsaturated molecule is preferably an unsaturated triglyceride. The monomer containing an oxygen-containing moiety is preferably at least one monomer selected from the group consisting of acetol, allyl alcohol, glycerol, glycols, epichlorohydrin, and acrolein.

Acetol is preferably reacted at temperatures between about 180° to about 250° C., and most-preferred reaction conditions are temperatures between about 195° to about 225° C. for 0.2 to 6 hours at a pressure/volume to keep greater than about 80% of the acetol in a liquid phase during the reaction. No catalyst is generally necessary. But use of a heterogeneous catalyst is a good option.

Allyl alcohol preferably is reacted with the bodied product at a temperature between about 240° to about 340° C. More preferred reaction conditions for reaction with allyl alcohol include a reaction temperature between about 250° to about 310° C.

The addition of monomers at these temperatures may increase acidity, often resulting in an acid number greater than 10 and a hydroxyl number greater than 20. The product may be reacted with an epoxy-containing molecule to reduce the acid number. The preferred means to handle high acidity is through neutralization with epoxy, as described earlier in the section entitled Epoxy Neutralization of Residual Acidity. When a multi-functional epoxy compound is used, both the hydroxyl number and molecular weight of the product may increase.

The oxygen-containing product may be further reacted with an isocyanate to form a urethane polymer.

B-Side Monomer Containing Both Epoxy and Hydroxyl Moieties

An alternative embodiment of this invention is a monomer urethane formulation where the monomer has both hydroxyl and epoxy moieties. In the broader sense, this embodiment comprises a B-side monomer that may be used in a urethane formulation. The B-side monomer comprises the following: a molecular structure containing at least 30 carbon atoms, at least one hydroxyl moiety, and at least one epoxy moiety. Preferably, the molar ratio of epoxy to hydroxyl moieties in the formulation (before reaction) is greater than 1:4, more preferably greater than 1:3 and less than 1:0.5, and most preferably, between 1:2.8 and 1:1.

Preferably, the monomer is a glyceride and the epoxy moiety is a secondary epoxy moiety on a fatty acid containing at least 16 carbon atoms. In one embodiment, the glyceride is a diglyceride. In another embodiment, the glyceride is an oligomer of at least two glycerides.

The most-preferred embodiment of this invention is a mixture of soybean oil that is epoxidized to form epoxy soybean oil and a polyol having a functionality greater than 3 and molecular weight greater than 500.

Diglyceride Formed from Selective Hydrolysis of Epoxy Soybean Oil

An alternative embodiment of this invention is a B-side monomer of a urethane formulation containing the diglyceride formed by the selective hydrolysis of epoxy soybean oil. In the broader sense, this embodiment is a process for synthesizing a B-side monomer of a urethane formulation comprised of the following: hydrolyzing some of the ester bonds of a glyceride-containing material to form hydroxyl moieties on the glyceride and a free fatty acid, and separating the free fatty acid from the B-side monomer containing the hydroxyl moieties that react with isocyanates.

Preferably, the hydrolysis is selective hydrolysis performed in a manner to selectively remove saturated fatty acids from the glyceride. Preferably, the glyceride-containing material is selected from the group consisting of castor oil or epoxy soybean oil. While this embodiment has been described as a B-side monomer, the use of this diglyceride in a urethane formulation may be other than as a B-side monomer.

Urethane Formulation with a B-Side that is a Monomer Containing Both Epoxy and Hydroxyl Moieties An alternative embodiment of this invention is a urethane formulation comprising a B-side that includes a monomer containing both hydroxyl and epoxy moieties. In the broader sense, this embodiment is a urethane formed by foaming process. The urethane formulation comprises: an A-side monomer comprised of isocyanate molecules, a B-side monomer comprised of at least one monomer containing at least one epoxy moiety and at least one hydroxyl moiety, and at least one catalyst and at least one surfactant. The A-side, the B-side, the catalyst, and the surfactant react to form a foam (i.e., a PUF formulation). Preferably, the molar ratio of epoxy to hydroxyl moieties in the formulation (before reaction) is greater than 1:4, more preferably greater than 1:3 and less than 1:0.5, and most preferably, between 1:2.8 and 1:1.

The catalyst (e.g., a liquid tertiary amine) serves to speed up the reaction of isocyanate and polyols. Generally, it is a crosslinking agent that forms a covalent bond in the polyurethane foam matrix. Typically, the function of the surfactant is to aid in the foam-forming processes and to avoid foam collapse and foam splitting.

Preferably, the monomer containing at least one epoxy moiety and at least one alcohol moiety is the diglyceride of epoxy soybean oil. Optionally, the hydrolysis uses enzymes that selectively remove the saturated fatty acid groups from the epoxy soybean oil. Preferably, the monomer containing at least one epoxy moiety and at least one alcohol moiety comprises from about 10% to about 50% of the B-side monomer mixture. Preferably, the PUF formulation contains 3% water in the B-side monomer mixture, and the isocyanate loading provides an isocyanate index between 100 and 130.

Urethane Formulation with B-Side that is Mixture of Epoxidized and Alcohol Monomers An alternative embodiment of this invention is a urethane formulation with a B-side comprising a mixture of an epoxy-containing monomer and a hydroxy-containing monomer. In the broader sense, this embodiment is a urethane formulation formed by a foaming process. The urethane formulation comprises the following: an A-side monomer comprised of isocyanate molecules, a B-side monomer mixture comprised of at least one monomer containing at least two epoxy moieties and at least one monomer containing at least two hydroxyl moieties, wherein the B-side contains at least 20% by weight of the monomer containing the epoxy moieties and at least 30% by weight of the monomer containing the hydroxyl moieties, at least one catalyst, and at least one surfactant. Stated differently, the molar ratio of epoxy to hydroxyl moieties in the formulation (before reaction) is greater than 1:4, more preferably, greater than 1:3 and less than 1:0.5, and most preferably, between 1:2.8 and 1:1. The A-side, B-side, catalyst, and surfactant react to form a foam (i.e., a PUF formulation).

Preferably, the monomer containing at least two epoxy moieties is epoxy soybean oil. Preferably, the monomer containing at least two epoxy moieties comprises from 10% to 50% of the B-side monomer mixture. Preferably, the PUF formulation contains 3% water in the B-side monomer mixture, and the isocyanate loading provides an isocyanate index between 100 and 130.

Urethane Formulation with B-Side that is Mixture of Epoxidized and Alcohol Monomers and Reduced Isocyanate Loading An advantage of a B-side monomer having both epoxy and hydroxyl groups is that the epoxy may be an intermediate in forming the alcohol, and so, conversion costs can be reduced if some epoxy is allowed in the final formulation. Thus, an advantage of a foam formulation containing both epoxy and hydroxyl groups is that the epoxy groups have delayed reactions and react with a wider range of other functional groups. A reaction strategy that has cost advantages includes using reduced isocyanate loading in the formation such that the alcohols react with the isocyanate to form a network that is substantial enough to retain its shape. Then, in a delayed reaction, the epoxy groups react with other functional groups in the urethane network to increase cross-linking and improve the structural properties of the final urethane product.

Methods and catalysts known to promote the reaction of epoxy groups with alcohol, urethane, and other groups are useful in these formulations. Catalysts effective for these reactions in other systems are generally effective in the formulations of this invention if they do not detrimentally interfere with other catalysts in the formulations.

Addition Reaction to Epoxy SBO

An alternative embodiment is a process for synthesizing a polyol via an addition reaction. The method comprises reacting a carboxylic acid having a carbon number of at least 12 reacts with a glyceride having at least two epoxy moieties. During the reaction each epoxy moiety is converted to a hydroxyl moiety or an ester moiety, with the ester moiety comprising a hydrocarbon chain containing at least 12 carbons. Preferably, the carboxylic acid is a free fatty acid having a carbon number greater than 13, the epoxy is an epoxidized vegetable oil, and the mass ratio of epoxidized vegetable oil and fatty acid is between 2 and 1. More preferably, this ratio is between 2 and 1.4. The preferred reaction conditions are 170° C. for 6 to 8 hours. More generally, the reaction conditions are from 140° to 190° C. for 2 to 17 hours. An even more general temperature range is from 120° to 260° C.

Alternatively, the carboxylic acid may be an estolide comprised of a chain of fatty acids having carbon numbers greater than 13 and the epoxy is an epoxidized vegetable oil. In yet another alternative, the carboxylic acid may be a hydrolyzed oligomer of a bodied vegetable oil.

The preferred epoxy is an epoxidized vegetable oil such as epoxy soybean oil. Preferably, the addition reaction is carried out at a temperature between 140° to 190° C.

B-Side Monomer with Large Non-Functional Branch

An alternative embodiment is a B-side monomer of a urethane formulation. The B-side monomer comprises a molecular structure containing at least 30 carbon atoms, at least one oxygen containing moiety, and at least one branch attached to a carbon containing an oxygen function. The branch contains at least eleven carbon atoms, no oxygen containing moieties, and terminates with a methyl group. The process for synthesizing this B-side monomer includes reacting a carboxylic acid with an epoxified glyceride, such as epoxy soybean oil. A suitable carboxylic acid is a free fatty acid such as linoleic acid. By example, linoleic acid will form a branch that is a straight-chain hydrocarbon branch. These monomers may react with isocyanates to form urethane polymers, where the branch of at least eleven carbons is a branch in the urethane polymer.

Bodied Oil with Epoxidation of Carbon-Carbon $\pi$-Bonds

An alternative embodiment of this invention is bodied soybean oil that is epoxidized to attach epoxy moieties. The bodied soybean oil may be prepared by the methods described earlier. Epoxidation is by ways known in the art.

Bodying of an unsaturated vegetable oil may be attained by maintaining the vegetable oil at a temperature greater than 180° C. for a time greater than one minute and until the ambient-temperature viscosity of the unsaturated vegetable oil is at least 25% greater than the viscosity prior to the bodying, and partially oxidizing the bodied unsaturated vegetable oil.

Preferably the following applies. The unsaturated vegetable oil is soybean oil. The bodying step is without a catalyst and at a temperature between 240° and 360° C. More preferably, the bodying step is performed at a temperature between 260° and 340° C. for a reaction time between 10 and 180 minutes.

More preferably, the following applies. The partially oxidizing step is an epoxidation reaction. The epoxidation is chemo-enzymatic epoxidation performed by enzyme catalysis including an immobilized lipase, hydrogen peroxide, soy-based fatty acids and organic solvent. The immobilized lipase is lipase B from *Candida antarctica* (NOVOZYME-435®) and 8% to 9% (wt) of the immobilized lipase is used.

By example, the soy-based fatty acids are stearic acid or linoleic acid and 15% (wt) of the fatty acid is used. The organic solvent is toluene and (3-4 ml solvent/g oil) is used. The hydrogen peroxide is 30 to 50% solution and is excessively charged to obtain the complete epoxidation. The chemo-enzymatic epoxidation is carried out at room temperature for longer than 24 hours. The epoxidation is performed by a reaction including hydrogen peroxide and an organic acid.

B-Side Components Synthesized with Functionalized Triglyceride Followed by Bodying A process for converting unsaturated vegetable oils into polyols is comprised of one or more of the following conversion mechanisms: 1) bodying the vegetable oil to allow for increased hydroxyl equivalent weights, 2) partially oxidizing carbon-carbon n-bonds to attach reactive moieties such as epoxy or hydroxyl moieties, 3) reacting carbon-carbon n-bonds with monomers containing oxygen moieties, and 4) hydrolyzing ester bonds to replace ester moieties with hydroxyl moieties. More specifically, a preferred process is addition of an oxygen function to a triglyceride followed by bodying of the triglyceride. Previously discussed embodiments of this invention that use this approach include: Epoxy Neutralization of Residual Acidity, Addition Reaction to Epoxy Soybean Oil, and B-Side Monomer with Large Non-Functional Branch.

An additional embodiment with functionalization of an unsaturated vegetable oil followed by bodying includes: formation of the epoxidized oil with from 15% to 100% of the carbon-carbon pi-bonds epoxidized (referred to as epoxy-containing intermediate) followed by a bodying process conducted at temperatures between 150° and 350° C. for less than 48 hours until the viscosity of the bodied product is at least 20% greater than the viscosity of the material prior to bodying. Alternatively, the epoxy-containing intermediate may be reacted with an unsaturated vegetable oil. In this bodying process, at least a fraction of the epoxy groups are transformed to alcohol groups and bodying occurs by both the Diels-Alder mechanism and mechanisms of the epoxy reaction.

The more-preferred reaction conditions for bodying the epoxy-containing intermediate is to react for 10 to 300 minutes at a temperature between 275° and 340° C.

Extended Applications

The triglyceride-based polyol products (and intermediates) of this invention are not limited to applications with isocyanates to form urethanes. The polyols are more-widely applicable to polyol applications known in the art as based on the properties of the respective polyols. In the broader sense, these compounds are known as hydroxyl-functional polyesters.

EXAMPLES

The following examples demonstrate preferred embodiments of the invention. They shall be interpreted are illustrative and not in a limiting sense.

Example 1

Reaction of Bodied Soybean Oil with Allyl Alcohol or Acetol

Reactions of bodied soybean oil were conducted in sealed containers in an oven without agitation. The bodied soybean oil (BSBO) was prepared by maintaining refined soybean oil at 330° C. for 30 minutes—a notable increase in viscosity indicated that oligomerization occurred in this bodying process. Iodine values were followed where a decrease in iodine values indicated that carbon-carbon n-bonds reacted.

The iodine number of soybean oil was 134. The BSBO had an iodine number of 97. Table 1 summarizes the results for the reaction of allyl alcohol with BSBO. In the course of these reactions at varying loadings of allyl alcohol, the iodine value of soybean oil decreased from 97 to 65-68. Exp. #4 and #5 of Table 1 show that soybean oil also reacted directly with allyl alcohol.

TABLE 1

Reaction of bodied soybean oil (BSBO) and soybean oil (SBO) with allyl alcohol.

| Exp. # | Oil (g) | Allyl Alcohol (g) | Allyl Alcohol (wt %) | T (° C.) | Duration (h) | Iodine Value |
|---|---|---|---|---|---|---|
| 1 | 6.02 (BSBO) | 0.74 | 12.3 | 300 | 2 | 68 |
| 2 | 6.03 (BSBO) | 0.35 | 5.8 | 300 | 2 | 66 |
| 3 | 6.02 (BSBO) | 1.10 | 18.3 | 300 | 2 | 65 |
| 4 | 6 (SBO) | 0.9 | 15 | 300 | 2 | 100 |
| 5 | 6 (SBO) | 0 | 0 | 300 | 2 | 118 |

The iodine value of soybean oil was 134.
The iodine value of soybean oil bodied for 30 minutes at a temperature of 330° C. (BSBO) was 97.

Table 2 summarizes the results for the reaction of acetol with BSBO or SBO. In the course of these reactions at varying loadings of acetol the iodine value of BSBO decreased from 97 to 63-65. Exp. #4 of Table 2 shows that soybean oil also reacted directly with acetol.

These results indicate that both allyl alcohol and acetol reacted with the carbon-carbon π-bonds of BSBO and presumably attached to the molecule, leading to polyols having primary alcohols. To confirm that the decreases in iodine numbers were not simply the further oligomerization of BSBO with other BSBO, a control was performed using glycerol.

TABLE 2

| Reaction Of BSBO With Acetol. | | | | | | |
|---|---|---|---|---|---|---|
| Exp. # | BSBO (g) | Acetol (g) | Acetol (wt %) | T (° C.) | Duration (h) | Iodine Value |
| 1 | 6.03 | 1.39 | 23 | 180 | 9 | 65.9 |
| 2 | 6.05 | 0.91 | 15 | 180 | 9 | 65.2 |
| 3 | 6.00 | 0.45 | 7.5 | 180 | 9 | 63.1 |
| 4 | 6.00 (SBO) | 1.39 | 23 | 180 | 9 | 95 |

Table 3 summarizes the results for the reaction of glycerol with BSBO. In the course of these reactions at varying loadings of glycerol the iodine value of BSBO remained at 97. The results of the glycerol reaction indicate that glycerol did not interact with the carbon-carbon π-bonds and is further indication that both allyl alcohol and acetol reacted with the carbon-carbon π-bonds.

A single-pot reactor approach that should have processing costs less than $0.15 per pound, as of the filing date of this patent application.

Ample and good degrees of freedom to control the average number of alcohols per molecule and the average hydroxyl equivalent weight.

The ability to create primary alcohol moieties.

FIG. 1 summarizes the performance of several synthesized and commercial soy-based polyols. A product based on reacting an acetol monomer with soybean oil is one of only two formulations that out-performed the petroleum-based commercial polyol (VORANOL® 490) used as a control.

Unlike glycerolysis of a triglyceride which only attaches a maximum of one glycerol per each polyol product, the glycerolysis products of bodied triglycerides can result in multiple glycerols per molecule. More importantly, the glycerolysis product of a bodied triglyceride incorporates much of

TABLE 3

| Reaction Of BSBO With Glycerol-Referred To As Glycerolysis Reaction. | | | | | | |
|---|---|---|---|---|---|---|
| Exp. # | BSBO (g) | Glycerol (g) | Glycerol (wt %) | T (° C.) | Duration (h) | Iodine Value |
| 1 | 6.02 | 0.74 | 12.3 | 210 | 9 | 96 |
| 3 | 6.0 | 1.12 | 18.7 | 210 | 9 | 98 |
| Exp. # | | Glycerol (wt %) | T (° C.) | Duration (h) | OH Number | Viscosity (cP) |
| B0 | | 5 | N/A | 0 | 90.0 | |
| B1 | | 5 | 225 | 3 | 78.8 | |
| B2 | | 5 | 225 | 5 | 77.8 | |
| B3 | | 5 | 250 | 3 | 74.7 | |
| B4 | | 5 | 250 | 5 | 73.8 | |
| B5 | 10.8 | 6 | 250 | 3 | 89 | 1760 |
| B6 | 8.5 | 6 | 250 | 5 | 82 | 1698 |
| B7 | 6.4 | 10 | 215 | 6 | 148.8 | 1338 |

The B-series reactions were performed with bodied soybean oil (BSBO) initially having an acid number of 37.3, iodine value of 90.9, OH number of 16.3, and viscosity of 940.5 cP.

In the case of ally alcohol and acetol reactions, a series of screening reactions were conducted to identify conditions that led to the desired interaction. Higher temperatures were required for good allyl alcohol reaction than for acetol reaction. The lower threshold temperature for good acetol reaction was indicative of observations that acetol tends to polymerize at temperatures near 200° C. (Dasari et al., Appl. Catal. A (2005) 281(1-2):225-231).

In the interpretation of these data it was assumed that if glycerol did not react with the carbon-carbon bonds π-bonds at 210° C., then it would also not react at 180° C.

FTIR analysis was performed in addition to the iodine value tests to determine if alcohol was present in the products of these reactions. In each case, the products were washed several times with water and dried. Any free alcohol should be readily removed through these washing steps. In addition, the self-polymerization products of both allyl alcohol and acetol are water-soluble and would also be removed in the water washes. Therefore, any alcohol moiety that showed up in the FTIR would be indicative of alcohols attached to the BSBO.

In the FTIR spectrum of the BSBO control for these studies, the absence of a transmittance peak at the 3470/cm wavelength indicated that no alcohol moieties were present on the BSBO. FTIR product spectra indicated that alcohol moieties were present on BSBO for both the allyl alcohol and the acetol reaction products.

These preliminary results indicate that soy-based polyols may be prepared with the following advantages:

the fatty acid backbone between alcohol groups which is necessary for good chain growth in subsequent urethane reactions. Addition of more glycerol leads to greater OH numbers for the final product. Catalysts such as potassium hydroxide promote the glycerolysis reaction. Preferred glycerolysis temperatures are between 150° and 300° C.; more-preferably between 190° and 260° C. The products of this reaction were successfully used to make flexible and rigid foams.

These results demonstrate the great potential for using acetol as a monomer for converting soybean oil to polyols in a very simple process.

Example 2

Simultaneous Bodying with Reaction Addition

This example illustrates a single-step reaction for the simultaneous bodying of the soybean oil and the reactive addition of acetol. The effects of anthraquinone as a catalyst and dicyclopentadiene as a crosslinker were also evaluated. The following abbreviations are used in Tables 4 and 5: soybean oil (SBO), dicyclopentadiene (DCP), anthraquinone (AQ). These reactions were conduced in a Par reactor or in small steel vessels.

TABLE 4

Summary of Parr reactor studies on simultaneous bodying and reaction addition.

| RXN # | SBO (g) | Acetol (g) | DCP (g) | AQ (g) | T (° C.) | Time (hr) | Acid No. | Iodine No. | OH No. |
|---|---|---|---|---|---|---|---|---|---|
| 1 | 100 | 15 | 0 | 2.5 | 250 | 20 | 24 | 95 | 52 |
| 2 | 100 | 15 | 0 | 2.5 | 250 | 20 | 25 | 92 | 55 |
| 5 | 100 | 15 | 14 | 0* | 250 | 20 | 46 | 106 | 72 |
| 6 | 100 | 15 | 14 | 0* | 250 | 20 | 45 | 100 | 72 |
| 7 | 100 | 15 | 14 | 2.5 | 250 | 20 | 39 | 99 | 52 |
| 8 | 100 | 15 | 14 | 5 | 250 | 20 | 54 | 98 | 60 |

*viscosity was low indicating lack of bodying reaction

TABLE 5

Summary of steel vessel reactor studies on simultaneous bodying and reaction addition.

| RXN #. | SBO (g) | Acetol (g) | DCP (g) | AQ (g) | Acid No. | Iodine No. | OH No. |
|---|---|---|---|---|---|---|---|
| v7 | 100 | 15 | 0 | 2.5 | 72.3 | 88.3 | 62 |
| v8 | 100 | 15 | 0 | 2.5 | 67.5 | 92.6 | 61 |
| v9 | 100 | 15 | 14 | 0* | 54.0 | 91.0 | 74 |
| v10 | 100 | 15 | 14 | 0* | 48.0 | 105.7 | 67 |
| v11 | 100 | 15 | 14 | 2.5 | 49.7 | 100.1 | 70 |
| v12 | 100 | 15 | 14 | 2.5 | 47.8 | 98.9 | 74 |
| v13 | 100 | 15 | 14 | 2.5 | 48.1 | 100.1 | 81 |
| v14 | 100 | 15 | 14 | 2.5 | 47.1 | 100.4 | 80 |

*viscosity was low indicating lack of bodying reaction

Several conclusions can be drawn from these reactions. Anthraquinone increased the viscosity as a result of this processing (observation not recorded in the tables) and it was recoverable as a filterable solid after the reaction. Therefore, it acted as a bodying catalyst that allowed bodying at temperatures of about 240-250° C., whereas temperatures >300° C. are normally needed for this effect. Concentrations of anthraquinone greater than 2.5% did not significantly promote a faster reaction. Bodying at lower temperatures resulted in a product with less darkening. Acetol provided for increased hydroxyl (OH) numbers. The presence of dicyclopentadiene led to higher acid and OH numbers possibly due to the abundance of conjugated carbon-carbon π-bonds that allowed for more abundant acetol addition.

For all of these reactions, the iodine number decreased from 36% to 46% (note that acetol in the initial reaction mixture caused an increase of initial iodine numbers to values between 130 and 145) indicating that the carbon-carbon π-bonds reacted. At least part of these reactions occurred between the acetol and the oil, leading to the attachment of the acetol and desired alcohol functionality. This was further substantiated by the increase in OH numbers above and beyond the increase in acid numbers. For the reactions without the anthraquinone, the reduction in iodine numbers was less (36-39% versus 41-46%), indicating that the anthraquinone catalyzed the bodying process. This was further substantiated by the observed higher viscosity of solutions with this catalyst. It is hypothesized that the acetol attachment increased the acidity, and that the increased acidity was not solely due to hydrolysis side-reactions.

Example 3

Hydrolysis of Bodied Soybean Oil

This example illustrates the enzymatic hydrolysis of bodied soybean oil to form a polyol. The reagents included lipases from *Candida rugosa* (Lipase AY “Amano”), *Burkholderia cepacia* (Lipase PS “Amano”), *Penicillium roquefortii* (Lipase R “Amano”), *Aspergillus niger* (Lipase A “Amano”), and *Mucor javanicus* (Lipase M “Amano”) from Amano Enzyme USA (Elgin, Ill., USA) and a lipase from *Rhizomucor miehei* from Sigma-Aldrich (St. Louis, Mo., USA) as well as food-grade refined soybean oil from a local grocery store.

Bodied soybean oil was produced by heating soybean oil at 330° C. for 45 min under a nitrogen gas environment. The heating process was done in a 1-liter Parr reactor and the volatile matters were removed during the reaction with a nitrogen purge. After 45 min, the viscosity of the oil was increased by 23% and the iodine number was reduced by 45%; the viscosity and iodine values for the bodied soybean oil were 0.67 $cm^2 s^{-1}$ and 80, respectively. Molecular weight distribution was determined by GPC.

The bodied soybean oil was partially hydrolyzed by commercial lipases without any surfactant or organic solvent. Bodied soybean oil (15 g), phosphate buffer at pH 7.0 (15 g) and lipase (70 mg) were placed in a 125-ml flask and the reaction conditions were controlled by an incubator shaker (Psycrotherm, New Brunswick, N.J., USA) at 45° C. and 300 rpm. Triplicate samples and one control sample (substrate+buffer, and without enzyme) were carried out concurrently.

Three reaction times were used: 1.5, 3, and 24 h. After the desired reaction times, the reaction products were left at room temperature to cool, and then washed and analyzed. The reaction conditions produced 15% to 50% of hydrolysis and the isolated polyols were typically about 50% by weight of the bodied soybean oil.

After the reaction, 45 ml of $Na_2CO_3$ (0.5 M) and 90 ml of diethyl ether were mixed together with the reaction product in a separatory funnel. The mixture was left overnight before high speed centrifuge was applied to help separate the fatty acid soap from the ether phase. Ester glycerides were in the ether phase (upper portion), whereas liberated fatty acids (free fatty acid soaps) were in the water phase (lower portion). Free fatty acids were recovered by acidification with HCl (conc.) and then solvent extraction by diethyl ether. Finally, diethyl ether in both the ether glycerides and hydrolyzed fatty acids was removed at 50° C. in an oven. Washing studies were also performed with the polyol product and $NaHCO_3$ (aqueous 0.5 M, pH 8.0).

The percent of hydrolysis (Table 6) is defined by the acid number of the hydrolyzed product. Acid enrichment numbers (AEN) of saturated fatty acids in the acid residue phase were calculated and reported in Table 6. An acid enrichment number of 1 or greater indicates that the enzyme significantly hydrolyzed the saturated fatty acids.

The hydroxy (OH) numbers reported in Table 6 were equal to the acid number of the hydrolyzed product (before product workup) because one mole of hydroxy is formed when one mole of acid is hydrolyzed. The hydroxy numbers of a few of the polyol products were determined using the standard method of hydroxy number titration (ASTM D4274, 2005). The reported hydroxy numbers in Table 6 were comparable to the numbers from the titration method.

TABLE 6

| Hydrolysis (%) and acid enrichment numbers of saturated fatty acids in the acid residue phase after the hydrolysis of bodied soybean oil. | | | | |
|---|---|---|---|---|
| | | 1.5 h/3 h/24 h | | |
| Enzyme | | AEN | Hydrolysis (%) | OH-number (mgKOH/g) |
| *C. rugosa* | (C16:0) | 1.6 ± 0.1/1.4 ± 0.2/1.3 ± 0.2 | | |
| | (C18:0) | 1.1 ± 0.1/0.9 ± 0.1/0.9 ± 0.1 | | |
| | | — | 22/27/42 | ~42/~51/~80 |
| *B. cepacia* | (C16:0) | 1.1 ± <0.1/1.2 ± 0.1/1.2 ± 0.1 | | |
| | (C18:0) | 1.0 ± <0.1/1.1 ± 0.1/1.1 ± 0.1 | | |
| | | — | 24/35/44 | ~46/~67/~84 |
| *A. niger* | (C16:0) | 1.2 ± <0.1/1.1 ± 0.1/1.0 ± 0.1 | | |
| | (C18:0) | 1.1 ± <0.1/1.0 ± 0.1/1.0 ± 0.1 | | |
| | | — | 15/15/23 | ~29/~29/~44 |
| *M. javanicus* | (C16:0) | 1.1 ± 0.1/1.1 ± 0.1/1.1 ± <0.1 | | |
| | (C18:0) | 1.0 ± 0.1/1.1 ± 0.1/1.0 ± <0.1 | | |
| | | — | 17/21/43 | ~32/~40/~82 |
| *R. miehei* | (C16:0) | —/1.1 ± 0.1/1.1 ± 0.1 | | |
| | (C18:0) | —/1.0 ± <0.1/1.1 ± 0.1 | | |
| | | — | —/29/39 | —/~55/~74 |

Two reactions were performed to hydrolyze bodied soybean oil with enzyme from *C. rugosa* (1.8 mg enzyme/gram oil). After the reaction reached 40% hydrolysis (acid number about 76 mg KOH/g), the products were washed with different base solutions; $Na_2CO_3$ (0.5 M, pH 11.0) and $NaHCO_3$ (0.5 M, pH 8.0), to remove fatty acids. The pH11 solution wash reduced the acid number of the oil to 10, while the pH 9 solution only reduced the acid number to 75.

Example 4

Acetol Addition to Soybean Oil

Acetol was reacted with soybean oil in small, closed steel reactors at the temperatures and times indicated in Table 7. The hydroxyl number increased as indicated for the reaction product after washing with water. The iodine values were between 132 and 118 cg Iodine/g as compared to an initial value of 132 for soybean oil. The acid values fluctuated from 10 to 25 in the product of low concentrations of acetol (7% to 10% per samples 1 to 10) and from 40 to 58 mgKOH/g at higher acetol concentrations. These data illustrate the successful addition of acetol to soybean oil. Evidence suggests that acetol reacts with conjugate carbon-carbon π-bonds in soybean oil. Reaction times of more than 9 hrs provided good results (as well as the times indicated in Table 7).

TABLE 7

| Results for reaction addition of acetol to soybean oil. | | | | |
|---|---|---|---|---|
| No. | Reaction | Temp (° C.) | Time (h) | OH number |
| 1 | SBO + Acetol (7%) | 180 | 13 | 15 |
| 2 | SBO + Acetol (10%) | 160 | 36 | 23.9 |
| 3 | SBO + Acetol (10%) | 170 | 20 | 21.2 |
| 4 | SBO + Acetol (10%) | 158 | 16 | 23.3 |
| 5 | SBO + Acetol (10%) | 170 | 18 | 24.4 |
| 6 | SBO + Acetol (10%) | 165 | 24 | 38.3 |
| 7 | SBO + Acetol (10%) | 180 | 16 | 47.3 |
| 8 | SBO + Acetol (10%) | 190 | 16 | 39.9 |
| 9 | SBO + Acetol (14%) | 190 | 28 | 34.0 |
| 10 | SBO + Acetol (10%) | 180 | 24 | 44.7 |
| 11 | SBO + Acetol (20%) | 160 | 48 | 21.7 |
| 12 | SBO + Acetol (15%) | 185 | 48 | 39.9 |
| 13 | SBO + Acetol (15%) | 185 | 96 | 37.1 |
| 14 | SBO + Acetol (15%) | 190 | 48 | 44.2 |

TABLE 7-continued

| Results for reaction addition of acetol to soybean oil. | | | | |
|---|---|---|---|---|
| No. | Reaction | Temp (° C.) | Time (h) | OH number |
| 15 | SBO + Acetol (15%) | 190 | 72 | 37.4 |
| 16 | SBO + Acetol (15%) | 220 | 24 | 69.2 |
| 17 | SBO + Acetol (15%) | 220 | 72 | 60.7 |
| 18 | SBO + Acetol (15%) | 240 | 24 | 44.5 |
| 19 | SBO + Acetol (15%) | 240 | 48 | 55.3 |
| 20 | SBO + Acetol (20%) | 220 | 24 | 64.4 |

Example 5

Soy-Based Polyols from Selective Hydrolysis

This example provides experimental results for the selective hydrolysis of soybean oil. Chemicals/enzymes used for the example are lipases from *C. rugosa* (Lipase AY "Amano"), *B. cepacia* (Lipase PS "Amano"), *Pseudomonas* sp. (Cholesterol esterase, "Amano" 2), *P. roquefortii* (Lipase R "Amano"), *P. camembertii* (Lipase G "Amano"), *A. niger* (Lipase A "Amano"), *M. javanicus* (Lipase M "Amano"), immobilized lipase from *B. cepacia* that were purchased from Amano Enzyme USA, Elgin, Ill.; lipase from *R. miehei* purchased from Sigma-Aldrich, St. Louis, Mo.; epoxy soybean oil (VIKOFLEX7-170®) purchased from ATOFINA Chemicals Inc, Philadelphia, Pa.; refined soybean oil (Food Club brand vegetable oil) from a local grocery store; Diazald, Tetramethylammonium Hydroxide (TMAH, 25% in methanol), Oleic acid (90%), Linolenic acid (99%), Hydrogen Peroxide and NOVOZYME-435® (lipase B from *Candida antarctica*) from Sigma-Aldrich, St. Louis, Mo.; linoleic acid (90%) purchased from City Chemical LLC, West Heaven, Conn.; flax seed oil from Jedwards International, Inc., Quincy, Mass.; and methanol, Diethyl ether, Potassium bicarbonate and Sulfuric acid from Fisher, Houston, Tex.

The enzymes obtained from Amano Enzyme Inc. were studied at their optimum pH and temperature as recommended in the product specification sheets and the reactions with *R. miehei* lipase were conducted at 45° C. and pH 7.0. Table 8 shows operating conditions, and enzyme activity as reported from the enzyme suppliers.

Two grams of soybean oil or epoxy soybean oil and two grams of buffer solution were mixed in a 125-mL Erlenmeyer flask. The reactions were performed in a controlled environment incubator shaker (PSYCROTHERM, New Brunswick, N.J.) at the speed of 300 rpm. For a reaction at given pH, temperature and time, three replications and one control (substrate+buffer, and without enzyme) were carried out concurrently. The enzyme unit was 67.5 units per gram of substrate. The reaction was stopped by adding 20 mL of a mixture of methanol and diethyl ether (80:20).

TABLE 8

Operating pH and temperature for enzyme hydrolysis screening test

| Lipase | pH | Temperature (° C.) | Activity, (units/gram) |
|---|---|---|---|
| *C. rugosa* | 7.0 | 45 | ≧30,000 |
| *B. cepacia* | 7.0 | 50 | ≧30,000 |
| *Pseudomonas* sp. | 7.0 | 35 | ≧10,000 |
| *P. camembertii* | 5.0 | 30 | ≧50,000 |
| *P. roquefortii* | 7.0 | 40 | ≧10,000 |
| *A. niger* | 6.0 | 45 | 12,000-15,000 |
| *M. javanicus* | 7.0 | 40 | ≧10,000 |
| *R. miehei* | 7.0 | 45 | ≧20,000 |

Only in the limit of zero hydrolysis will the true, fundamental selectivity of the hydrolysis be revealed in a single concentration profile. Conversion data at 100% hydrolysis will not reveal information on selectivity. Reaction times of this investigation were selected to provide about 15% conversion since soybean oil contains about 15% saturated fatty acids. The actual conversions are presented in FIG. 2 and typically varied from 5% to 20%.

After stopping the reaction, 80 mL of 0.5 M potassium bicarbonate and 15 mL of diethyl ether were added into the reaction product (glyceride-fatty acid mixtures). The mixture was placed in a separatory funnel. The glyceride portion (oil phase) was separated from the free fatty acid soap, which was in the lower water phase. Free fatty acid soap residues were recovered from the water phase by acidification with sulfuric acid and then by solvent extraction with diethyl ether. Lastly, the diethyl ether in both the glyceride fraction and acid residue fraction was evaporated at 45° C.

Figure 2:
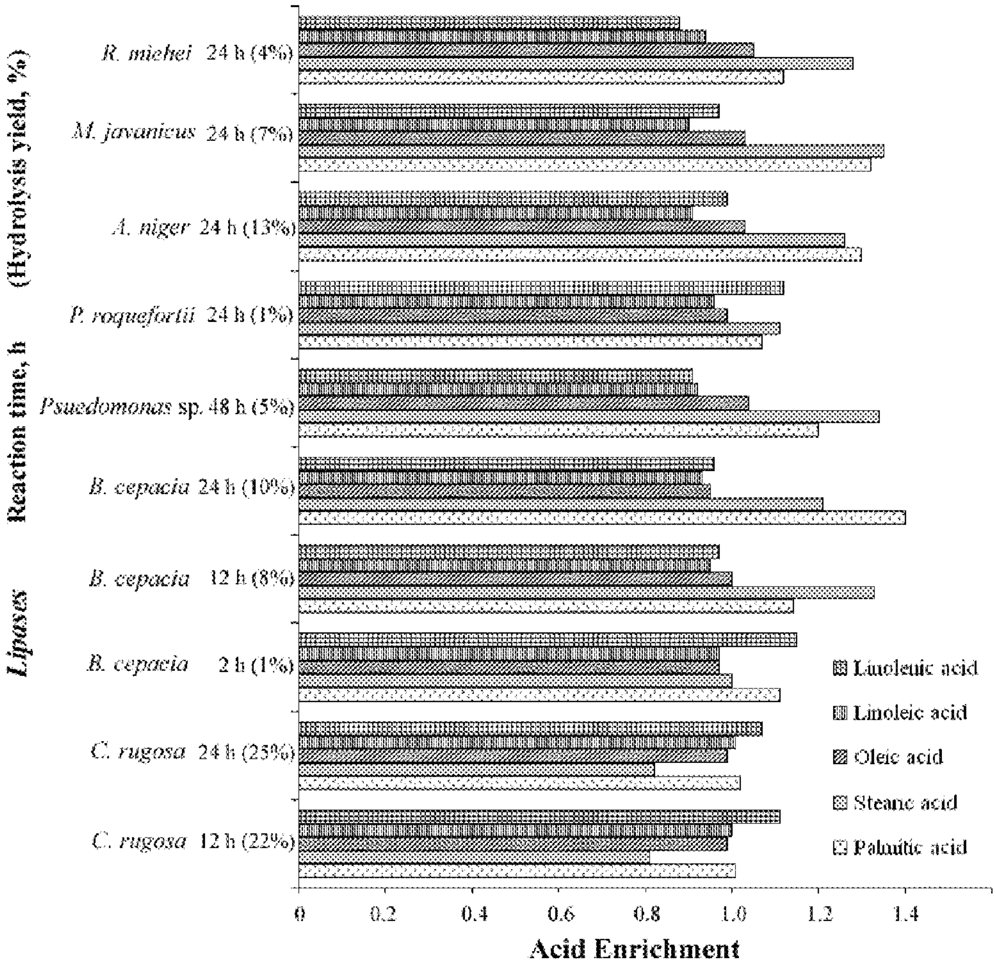
FIG. 2 presents the acid enrichment numbers of fatty acid products after enzymatic hydrolysis of soybean oil.
Figure 3:
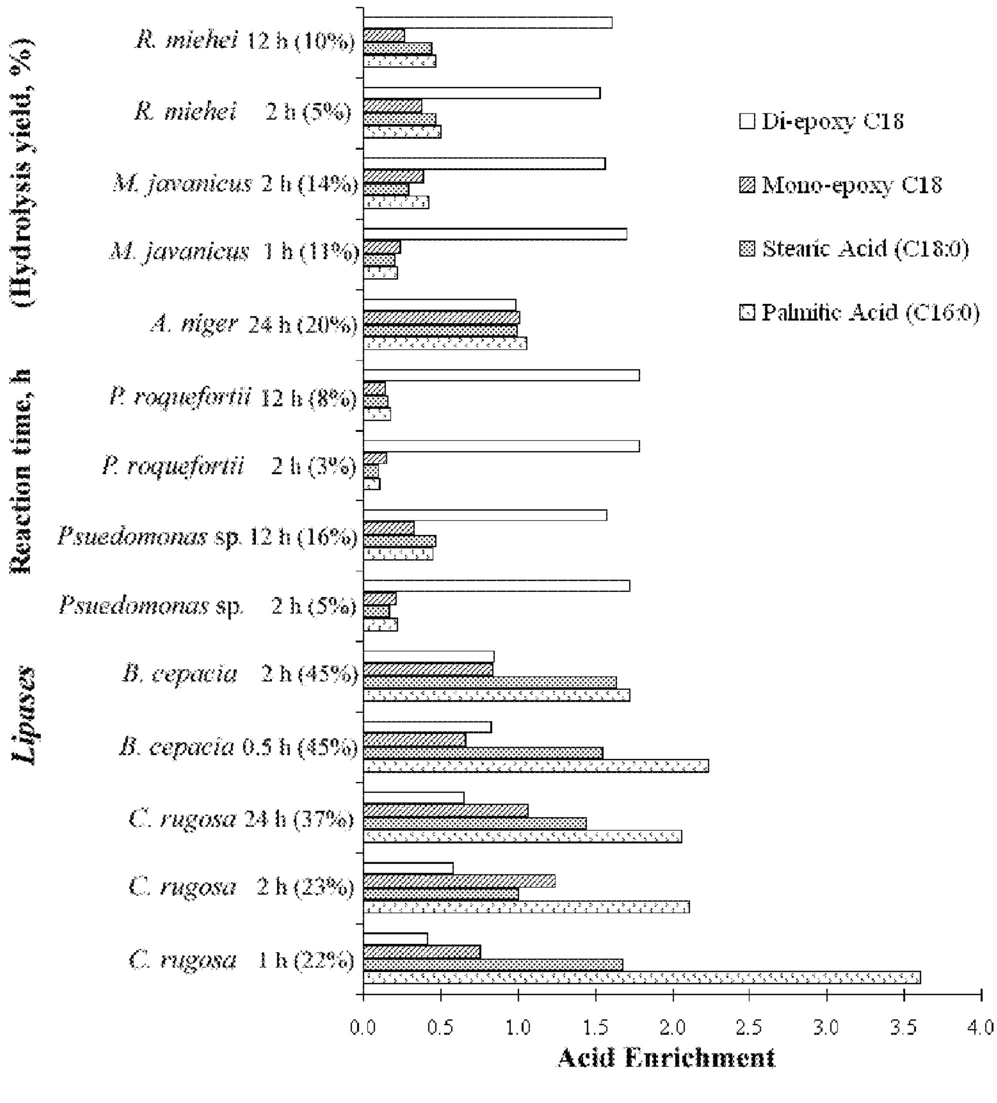
FIG. 3 presents the acid enrichment numbers of fatty acid products after enzymatic hydrolysis of epoxy soybean oil.

FIG. 2 presents the hydrolysis conversions and the compositions of the glyceride phase and the fatty acid phase after enzyme hydrolysis of soybean oil. FIG. 3 shows the hydrolysis conversions and the constituents in the glyceride phase and the fatty acid phase after enzyme hydrolysis of epoxy soybean oil.

After product workup, the enrichment number of each acyl moiety in the fatty acid phase was calculated in order to investigate enzyme selectivity. The following equation defines the enrichment number:

$$\text{Enrichment number of acylmoiety } 'A' \text{ in fatty acid residue} = \frac{(\%\text{ normalization of } 'A' \text{ in fatty acid phase})}{(\%\text{ normalization of } 'A' \text{ in triglyceride substrate})}$$

where A is palmitic acid, stearic acid, or other acyl moieties. The total of every component's signal is 100 in percent normalization.

The higher the acid enrichment number, the higher the enzyme selectivity toward hydrolyzing a particular acyl moiety. FIG. 2 and FIG. 3 show enrichment numbers from the reactions of soybean oil triglyceride and of epoxy soybean oil triglyceride, respectively.

Rates of hydrolysis significantly increased in the reaction of epoxy soybean oil relative to soybean oil (see FIG. 2 and FIG. 3). The reaction conversion increased from 25% to 37% (24 h) by *C. rugosa* lipase. The hydrolysis of epoxy soybean oil by *B. cepacia* lipase resulted in a 45% conversion (2 h) while the reaction with soybean oil yielded only 1% (2 h). This is likely due to the emulsifying characteristics of the epoxy group, which tends to increase the interface area between lipids and water.

The emulsifying nature of epoxy soybean oil was confirmed by observations. Lipid-water mixtures during and after the hydrolysis of epoxy soybean oil were cloudy, while mixtures with soybean oil were less cloudy and more-readily separated into isolatable phases.

Example 6

Rigid Foam with Epoxy in B-Side

Rigid polyurethane foams were made using a standard mixing procedure. This procedure involved intensive mixing using a commercial drill press (Colcord-Wright, St. Louis, Mo.) fitted with a 25.4 cm shaft with a 5 cm impeller arranged to turn at 3450 rpm. The B-side mixture components, which included polyether polyol (Voranol 490), soybean oil polyols, catalyst, surfactant, and water (as a blowing agent), as shown in Table 9, were sequentially weighed by a balance and added into a 0.946 L (1 quart) disposable paperboard container fitted with a steel frame with four baffles next to the container wall, and mixed at 3450 rpm for 10-15 s. Then stirring was stopped, to allow the mixture to degas. After 120 s, polymeric isocyanate was rapidly added and stirring was continued for another 10 s at the same speed. Finally, the reacting mixtures were poured immediately into wooden boxes (220 by 220 by 150 mm) and allowed to rise at ambient conditions. Foams were removed from boxes after 1 hour and allowed to cure at room temperature (23° C.) for one week before cutting into test specimens with a band saw. The properties of typical rigid polyurethane foams made from 50% polyether polyol and 50% soybean oil polyols are shown in Table 10. The isocyante indices include the epoxy as two hydroxyl groups (e.g., reaction of water to form two hydroxyl groups).

TABLE 9

Composition of the B-side mixture.

| Materials | Parts |
|---|---|
| VORANOL ® 490 | 90-50 |
| Soybean oil polyol | 10-50 |
| Water | 3 |
| POLYCAT ® 5 | 1.26 |
| POLYCAT ® 8 | 0.84 |
| DABCO ® DC 5357 | 2.5 |

TABLE 10

Properties of typical rigid polyurethane foams using 100% polyether polyol or 50% polyether polyol and 50% soybean oil polyols.

| Polyols | Isocyanate Index | Thermal conductivity (W/mK) | Density ($kg/m^3$) | Compressive strength (kPa) |
|---|---|---|---|---|
| 100% VORANOL ® 490 | 110 | 0.02724 | 49.44 | 397.6 |
| 50% VORANOL ® 490 50% Epoxidized and oxidized soybean oil | 110 | 0.02803 | 45.62 | 294.6 |
| 50% VORANOL ® 490 50% Epoxidized bodied soybean oil | 110 | 0.02744 | 46.57 | 343.8 |
| 50% VORANOL ® 490 50% Diglyceride of epoxy soybean oil | 110 | 0.02562 | 34.16 | 284.0 |
| 100% VORANOL ® 490 | 110 | 0.02724 | 49.44 | 397.6 |
| 50% VORANOL ® 490 50% Epoxidized soybean oil | 110 | 0.03247 | 49.25 | 346.89 |
| 50% VORANOL ® 490 50% Epoxidized soybean oil | 92.2 | 0.03261 | 44.04 | 256.96 |
| 50% VORANOL ® 490 50% Epoxidized soybean oil | 83.5 | 0.03214 | 41.62 | 227.42 |
| 50% VORANOL ® 490 50% Epoxidized soybean oil | 79.2 | 0.03304 | 41.13 | 225.49 |
| 50% VORANOL ® 490 50% Epoxidized soybean oil | 77 | 0.03330 | 38.85 | 209.0 |
| 50% VORANOL ® 490 50% Epoxidized soybean oil | 75.5 | 0.03388 | 38.86 | 195.28 |

The data of Table 10 illustrate that rigid formulations can include substantial amounts of epoxy functionality rather than hydroxyl functionality. The range of acceptable indices, for this formulation, are between those based on only including alcohol groups in the OH# and that which includes the alcohol groups plus two alcohol groups for each epoxy group.

As a control to the Table 10 data, a rigid foam was made with a B-side containing 50% VORANOL® 490 and 50% soybean oil. The control had a compressive strength of 90 kPa, which is clearly inferior to all the foams of Table 10.

Example 7

Polyols Formed from Reaction Addition to Epoxy Soybean Oil

This example illustrates the synthesis of higher molecular weight polyols from addition reaction to epoxy soybean oil. Chemicals used in the synthesis include castor oil from Alnor Oil Company (Valley Stream, N.Y.), soybean oil (food grade) obtained from a local grocery store, epoxy soybean oil (VIKOFLEX® 7170) from Atofina Chemicals (Philadelphia, Pa.). Ricinoleic acid (technical grade) from Arro Corporation (Hodgkins, Ill.), enzyme *Candida rugosa* (lipase Amano “AYS”) from Amano Enzyme Inc. USA (Elgin, Ill.), and immobilized lipase B from *C. antarctica* (NOVOZYME-435®), lipase from *R. miehei* and anthraquinone catalyst (90%) from Sigma Aldrich (St. Louis, Mo.).

Acid numbers of dry samples were evaluated according to the method of acid value, AOCS Te 1a-64. The hydroxyl number was evaluated according to the determination of hydroxyl numbers of polyols, ASTM 4274-05. The epoxy content of a dry sample was analyzed by an official method, AOCS Cd 9-57, oxirane oxygen.

Estolide Synthesis—To produce ricinoleic acid (RC) estolides, lipase from *C. rugosa* and immobilized lipase B from *C. antarctica* (NOVOZYME-435®) were used in the esterification without any organic solvent. The esterification took place at temperatures of 40° C. and 60° C., and at pressures of 1 atm (open system) and 0.63 atm. Vacuum pressure (0.63 atm) was applied to remove water, an esterification product, and prevent the reversible reaction from taking place.

Ricinoleic acid had an acid number of 142 (mg KOH/g), which can be converted to the acid equivalent weight of about 395. Acid numbers of ricinoleic acid decreased when the fatty acid was kept at room temperature (22° C.) due to slowly condensation polymerization. To maintain the acid number of the hydroxy fatty acids, all samples were kept in the refrigerator (below 5° C.).

To start the esterification, enzyme *C. rugosa* (0.6 g) or NOVOZYME-435® (1 g) was combined with 15 g of ricinoleic acid fatty acid in a 125-Erlenmeyer flask and the operation mode was well-mixed batch. Three reactions were performed concurrently and the standard deviation was calculated.

After the reaction was performed (usually after 120 h), the immobilized enzyme was removed from the reaction product by centrifuge. Acetone was used to wash NOVOZYME-435® and the immobilized enzyme was reused for the next reaction after evaporating the acetone at 60° C.

NOVOZYME-435® was reused to investigate the enzyme’s lifetime. The lipase was washed with acetone and dried after every reaction before being recycled.

Polyols with the higher hydroxyl equivalent weight were made by the cleavage of epoxy rings with fatty acid estolides. The fatty acid estolides were yielded from enzyme esterification of RC, as previously described. The RC estolide with acid number of 79 (produced under 60° C., 1 atm, 120 h by NOVOZYME-435®) was combined with ESBO, with the ratio of epoxy to acid being 1:0.66 by mole. The reaction took place in a batch well-mixed reactor at 170° C. and 1 atm until the acid number of polyols product was less than 10 (mg KOH/g).

Bodied Soybean Oil Synthesis—BSBO was produced by heating soybean oil with 2.5% of anthraquinone catalyst at 260° C. for 6 h. The bodying process was done in 1-liter Parr reactor with volatile matters being removed during the reaction by a venting channel. The solid catalyst was reusable and was removed from the BSBO by centrifugation. After 6 h, the bodying process increased the viscosity by 5.5 times and reduced the iodine number by 25%, with the viscosity and the iodine values for the bodied soybean oil being 313 mPa·s (at 22° C.) and 90, respectively.

BSBO was partially hydrolyzed by commercial lipases without any surfactant or organic solvent. The bodied soybean oil, phosphate buffer pH=7.0 (0.7 g/g oil), and *R. miehie* lipase (6.6 μl/g oil) were combined and mixed before the reaction started. The hydrolysis took place at 45° C. at 1 atm in a well mixed reactor for 3 days.

Figure 4:
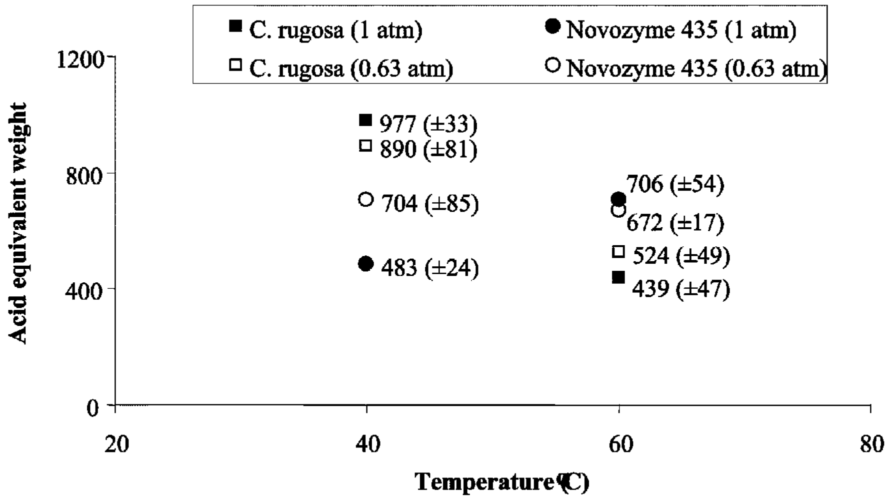
FIG. 4 presents the average acid equivalent weights of ricinoleic acid estolides after enzyme esterification (120 h).

After the reaction, water and enzyme were separated from the oil phase by centrifuging (4000 rpm, 30 min). The product HBSBO had an acid number of about 83 (mg KOH/g). Examples of BSBO and HBSBO are displayed in FIG. 4. The HBSBO had acid functional groups with high MW and were furthered used to open the epoxy ring of EBSO.

HBSBO (acid number=83 mg KOH/g) was produced from the enzyme hydrolysis of BSBO, which was previously described. The HBSBO and ESBO were combined with the ratio of epoxy per acid of 1:0.66. The reaction took place at 170° C. at 1 atm until the acid number was less than 10 (mg KOH/g). Acid number and epoxy content were determined against time.

Reaction Addition of Fatty Acids to Epoxy Soybean Oil—Linoleic acid (LA) and ricinoleic acid (RC) were used to open oxirane rings of epoxy soybean oil (ESBO). To perform the reaction, ESBO and LA (acid number=190 mg KOH/g), or ESBO and RC (acid number=142 mg KOH/g) were combined and reacted at 170° C. and at atmospheric pressure. The reaction was simply performed in a well-mixed batch reactor. Three ratios of epoxy functional group to acid functional group were used; 1:1, 1:0.8 and 1:0.5 by mole. Samples were collected with respect to time to measure acid number and epoxy content for the kinetic studies.

Figure 5:
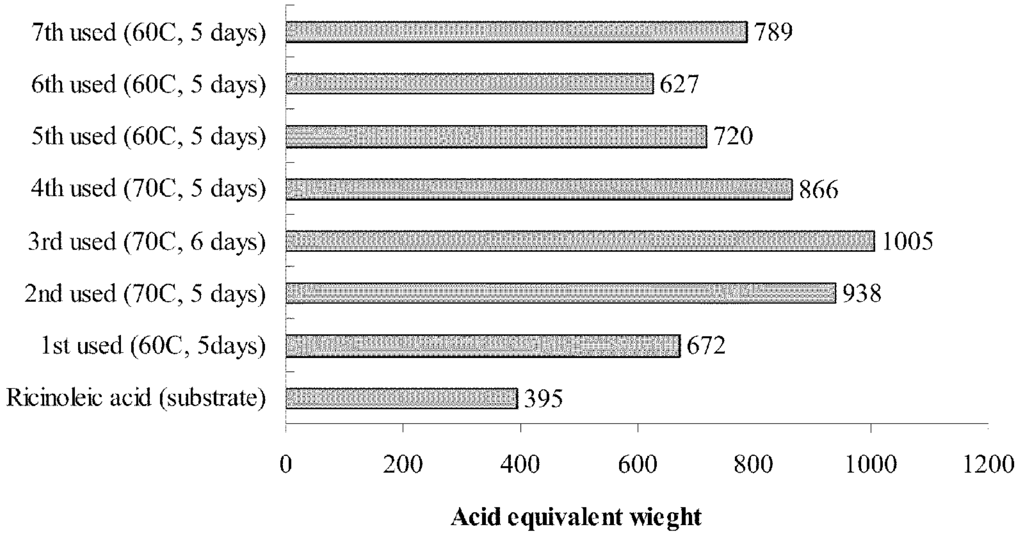
FIG. 5 illustrates the acid equivalent weights of ricinoleic acid estolides produced with recycled NOVOZYME-435®.

Summary of Product Properties—Acid equivalent weights of ricinoleic acid estolides synthesized by enzyme transesterification are shown in FIG. 5. The higher the reaction conversion is, the higher the acid equivalent weight is or the higher the average MW.

RC estolides produced from the recycled immobilized lipase, NOVOZYME-435®, are presented in FIG. 5. The immobilized enzyme, NOVOZYME-435®, was recycled and used at 1 atm (60° and 70° C.), as a result (FIG. 5), the enzyme's activity and reactivity were still good after 7 times of recycling with a batch well-mixed operation (60-70° C.).

Typical properties reported for the commercial polyols are acid number, hydroxyl number, OH equivalent weight, MW, functionality, and viscosity. The apparent MW of soy-based polyols analyzed by gel permeation chromatography (GPC) was found to be higher than their real value due to their bulky molecular structure. The relative MW of soy-based polyols can be easily observed by their viscosity and OH numbers. The higher viscosity, the higher the MW. However, the OH and epoxy functional groups also increased the polyols' viscosity.

Properties of high equivalent weight soy-based polyols produced from ESBO are shown in Table 11. Properties of a commercially available soy-based polyol, SOVERMOL® 1068 (alkoxyl hydroxyl soybean oil), are also shown in the same table.

TABLE 11

Properties of polyols made from ESBO and vegetable oil based acid moieties.

| Acid moieties (acid number | Ratio of epoxy to acid moieties | Rxn time (h) | Properties of Polyols: Acid # (mg KOH/g) | OH # (mg KOH/g) | OH Equ. weight | Epoxy wt % | Viscosity (22° C.) (mPa s) |
|---|---|---|---|---|---|---|---|
| LA (190) | 1:1 | 17 | 25 | 76 | 740 | <0.1 | 1400 |
| | 1:0.8 | 17 | 14 | 107 | 520 | <0.1 | 2540 |
| | 1:0.5 | 17 | 4 | 112 | 500 | 0.8 | 2860 |
| RC (142) | 1:1 | 13 | 16 | 159 | 350 | <0.1 | 9420 |
| | 1:0.8 | 13 | 16 | 163 | 340 | <0.1 | 8620 |
| | 1:0.5 | 10 | 5 | 152 | 370 | 0.2 | 7670 |
| RC estolide (79) | 1:0.66 | 6 | 8 | 109 | 520 | 0.3 | 5290 |
| HBSBO (83) | 1:0.66 | 6 | 10 | 82 | 680 | 0.3 | 3000 |
| Alkoxyl hydroxyl soybean oil (SOVERMOL ® 1068)* | | — | 0-3.9 | 180-205 | 270-310 | — | 3000-6000 (at 20° C.) |

*A commercial product and product's properties by Cognis Oleochemicals

Normally, the acid numbers of commercially available polyols are lower than 10 (mg KOH/g). An excess amount of epoxy group is needed to reduce the polyols' acid number because the possible side reactions could also take place.

Example 8

Flexible and Semi-Rigid Foams with Long Branch Groups

Foams were prepared using the formulations of Table 12. Table 13 reports the performance of these foams. Table 14 reports the preparation of the R10-R13 samples. The performance data indicates good performance for the R10-R13 performance, therein demonstrating the ability to use these soy-based polyols in flexible foam formulations.

TABLE 12

| Flexible foam formulations. |
|---|
| For 100% VORANOL ® 4701: |
| VORANOL ® 4701: 100 parts by weight (pbw) |
| Water: 5.0 pbw |
| DABCO ® 33-LV: 0.3 pbw |
| DABCO ® BL-17: 0.2 pbw |
| Diethanolamine: 2.2 pbw |
| DABCO ® 2585: 0.5 pbw |
| PAPI ® 27: Index 80 |
| For 50% of soy-based polyols and 50% of VORANOL ® 4701: |
| VORANOL ® 4701: 50 parts by weight (pbw) |
| Soy-based polyols: 50 pbw |
| Water: 5.0 pbw |
| DABCO ® 33-LV: 0.6 pbw |
| DABCO ® BL-17: 0.2 pbw |
| Stannous Octoate: 0.3 pbw |
| Dibutyltin Dilaurate: 0.3 pbw |
| Diethanolamine: 2.2 pbw |
| DABCO ® 2585: 1.0 pbw |
| PAPI ® 27: Index 80 |

TABLE 13

Performance of foams using formulations of Table 12. ESBO is epoxy soybean oil and LA is linoleic acid.

| | 1 VORANOL ® 3136 | 2 Castor Oil | 3 SOVERMOL ® 1068 | 4 Batch 5 | 5 ESBO + LA-4701 | 6 VORANOL ® 4701 | 7 R10 + R11 + R12 + R13 | 8 R10 + R11 + R12 + R13 |
|---|---|---|---|---|---|---|---|---|
| OH Value | 54 | 160 | 180-205 | 192.5 | 118.2 | 34 | 113.61 | 113.61 |
| Isocyanate Index | 80 | 80 | 80 | 80 | 100 | 80 | 100 | 80 |
| Density (kg/m3) | 42.29 | 48.29 | 51.05 | 37.6 | 41.29 | 44.83 | 42.6 | 46.75 |
| CFD, 50% Deflection (kPa) | 15.47 | 31.65 | 27.65 | 13.4 | 38.22 | 8.78 | 19.73 | 11.59 |
| CDC, 50%, Ct = [(to − tf)/to] 100 | 13.04 | 21.83 | 45.7 | 45.98 | 41.45 | 5.54 | 33.19 | 16.35 |
| Tear (N/m) | 149.21 | 241.32 | 332.56 | 188.54 | 256.94 | 142.4 | 187.22 | 153.73 |
| Resilience (%) | 46.36 | 19.83 | 18.22 | 16.78 | 36 | 44.89 | 34.44 | 36.78 |

TABLE 14

Properties and reaction conditions for R10-R13 epoxy soybean oil based polyol of Table 13. The acid is linoleic acid.

| | | Product properties | | | | |
|---|---|---|---|---|---|---|
| Epoxy:Acid (by mole) | Reaction conditions | Acid # (mg KOH/g) | OH # (mg KOH/g) | OH Equ. weight | Epoxy content (% by wt.) | Viscosity (22° C.) (cP) |
| 1:0.5 | 170° C./17 h | 4 | 112 | 500 | 0.8 | 2860 |

Example 9

Epoxidized Soy-Based-Materials from Enzymatic Epoxidation Including Diglycerides This example illustrates the synthesis of epoxy soybean oil. The chemicals for synthesis include refined soybean oil (food grade) from a local grocery store, linoleic acid (90%) from City Chemical LLC (West Heaven, Conn.), stearic acid (>90%), NOVOZYME-435® (immobilized lipase B from *Candida antarctica* on acrylic resin) from Sigma Aldrich (St. Louis, Mo.), and hydrogen peroxide solutions (30%) from Fisher (Houston, Tex.).

Well-Mixed Reactor—Soybean oil (5 g), linoleic acid (0.3 g) and toluene (10 ml) were combined in a 125-ml Erlenmeyer flask. Immobilized lipase, NOVOZYME-435®, (0.53 g) was added to the mixture when the reaction started. Hydrogen peroxide solution (30%) was added dropwise during the first 5 h of the reaction. Three ratios of hydrogen peroxide to C═C double bonds ($H_2O_2$:C═C) were used: 0.6, 0.8 and 1.0 by mole. The reaction further continued for 24 h in a controlled environment incubator shaker (PSYCROTHERM, New Brunswick, N.J.) at room temperature and the speed of 300 rpm.

Water, unreacted hydrogen peroxide, and immobilized enzyme were removed from the reaction product due to immiscibility of these materials in the oil phase. Fatty acid was removed by a saponification method. Either sodium dicarbonate, or sodium carbonate solution (0.5 N) was used to saponify the fatty acid after the reaction. After the saponification, the fatty acid soap was formed and stayed in the water phase. A centrifuge is also used to speed up the phase separation process. Toluene was finally removed from the epoxy soybean oil before measuring the epoxy content.

To study the effect of hydroperoxy on the enzyme's activity, the amount of hydrogen peroxide was varied; 0.6, 0.8 and 1.0 of $H_2O_2$:C═C by mole, which yielded an epoxy functionality of 2.8, 3.7, and 4.6 in complete epoxidation. The epoxidation conversion after the reaction was evaluated by the titration of epoxy weight percent and is shown in FIG. 6.

Figure 6:
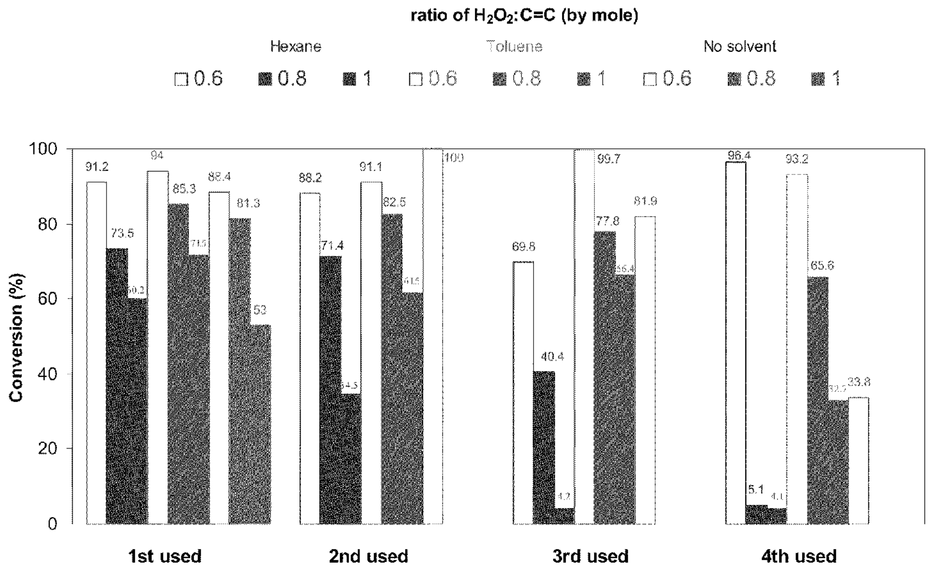
FIG. 6 presents the effects of organic solvent and hydrogen peroxide ($H_2O_2$) on chemo-enzymatic epoxidation of soybean oil triglyceride by NOVOZYME-435®.

From FIG. 6 it can be seen that commercially available immobilized lipase B from *C. antarctica* (NOVOZYME-435®) was an effective biocatalyst in the epoxidation of soybean oil triglyceride. The reaction yielded over 90% conversion and the lipase was also reusable with high activity under some operating conditions.

In hexane or toluene, the lipase's activity was well maintained after four reuses when less hydrogen peroxide is used (0.6 mole ratio of $H_2O_2$:C═C). These data suggest that the hydroperoxide solution reduced the enzyme's activity and shorted the enzyme's life, as indicated by the decrease of the reaction conversion after three uses when the higher amount of hydrogen peroxide was used.

The organic solvents preserved the enzyme's activity. At 0.8 and 1.0 mole ratios of $H_2O_2$:C═C and without any solvent, the enzyme did not yield any significant conversion after two uses. Toluene and hexane gave comparable results until the second use of the enzyme.

Figure 7:
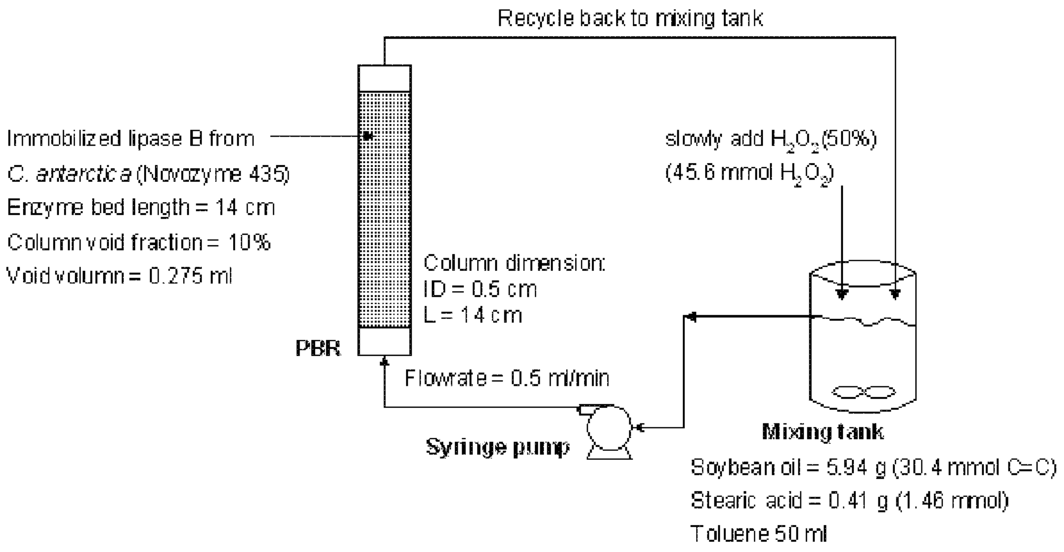
FIG. 7 diagrams the packed-bed reactor of chemo-enzymatic epoxidation to produce epoxy soybean oil triglyceride.

Packed-Bed Reactor—The PBR design and operation of chemo-enzymatic epoxidation of soybean oil is illustrated in FIG. 7. Every 24 h, a small sample (100 μl-200 μl) in the mixing tank was drawn and reacted with tetramethylammonium hydroxide in methanol to prepare methyl ester derivatives of the epoxidized products ready for GC-analysis.

According to the operation of PBR producing epoxy soybean oil in FIG. 7, a sample was taken every 24 h for 72 h. GC-FID analysis was used to determine the percentage of each fatty acid methyl ester. It was found that the maximum disappearance of unsaturated fatty acids occurred after 48 h with the percent disappearance of linolenic, linoleic, and oleic acid at 62%, 51%, and 30%, respectively.

Among unsaturated fatty acids in soybean oil, the disappearing percentage of the linolenic acid (18:3) was highest, followed by the linoleic acid (18:2) and the oleic acid (18:1), respectively. However, the reaction yields produced from PBR were not as high as those produced from the well-mixed reactor. In addition, the epoxy fatty acid moieties were predominately mono-epoxy stearic acids, as analyzed by GC-FID. Hydrophilicity of the enzyme's support might cause poor mass transfer resulting in low epoxidation yield. To increase epoxidation yield by the PBR operation, a surfactant could be used to create a reverse micelle system and not deactivate the enzyme.

Chemo-enzymatic epoxidation of blown soybean oil, bodied soybean oil and soy-based diglycerides—Soybean oil triglyceride has iodine number of 120 and 85% of unsaturated fatty acid. The epoxy content of epoxidized blown soybean oil, epoxidized bodied soybean oil and epoxidized soy-based diglycerides were evaluated by the titration method. The values were 3.8%, 5.5%, and 2.5% for soy-based diglyceride, bodied soybean oil, and blown soybean oil after chemo-enzymatic epoxidation versus 0.2%, 0.2%, and 0.8% before the reaction. For a reference, the complete epoxy soybean oil had 6.8-7.0% epoxy content (by wt).

Originally, the epoxy content in blown soybean oil was a little higher than in the other soy-based material. This is because blown soybean oil is the oxidized product from heat and oxygen gas. Blown soybean oil could have either epoxy or peroxy functional groups detected by the titration method. The production of bodied soybean oil was performed under $N_2$ gas environment where any oxidizing functional group should not be produced.

The iodine numbers of bodied soybean oil and soy-based diglyceride were comparable, and were about 55-58% of the iodine number of soybean oil triglyceride. However, the epoxidation product of bodied soybean oil was about 5.5% epoxy content and the epoxidation product of soy-based diglyceride was about 3.8% epoxy content.

Low reaction yield of the epoxidation of soy-based diglyceride was limited by the amount of hydrogen peroxide used, which was 0.5:1 of $H_2O_2$:C═C (by mole). From GC-analysis of ENOVA® oil, the substrate had C═C functionality of 3.4, which could be converted to 9% of epoxy content if the complete epoxidation was achieved.

As a result, the reaction conversion of the epoxidation of soy-based diglyceride under the described condition was about 76%. The reaction conversion was not changed when linoleic acid was replaced with formic acid, which is a common acid used in chemical route of the epoxidation.

Blown soybean oil had lower degrees of unsaturation, as indicated by the low iodine number. The epoxidized blown soybean oil, which was produced under the described conditions, contained 2.5% epoxy content.

Example 10

Flexible and Semi-Flexible Foams from Bodied SBO and Fatty Acid Addition Polyols This example illustrates the synthesis of several flexible foams. Polyols were prepared as follows:

Sample F1—BSBO (100 grams, iodine value of 103.8) was mixed with 15 grams of acetol and 14 grams DCP at 220° C. for 20 hours. The intermediate had an acid number of 48, iodine number of 106 (26% reduction) and OH number of 63. To this was added 16.2 grams of ESBO, which was reacted at 170° C. for 6 hours. The final polyol had an acid number of 7, epoxy content of 0.6%, and OH number of 98.

Sample F2—BSBO (100 grams, iodine value of 103.1) was mixed with 20 grams of acetol and 14 grams DCP at 220° C. for 20 hours. The intermediate had an acid number of 55, iodine number of 104 (25% reduction) and OH number of 66. To this was added 14 grams of ESBO, which was reacted at 170° C. for 6 hours. The final polyol had an acid number of 4.6, epoxy content of 0.6%, and OH number of 101.

Sample F3—BSBO (100 grams, iodine value of 103.8) was mixed with 20 grams of acetol and 14 grams DCP at 200° C. for 20 hours. The intermediate had an acid number of 52, iodine number of 111 (20% reduction) and OH number of 42. To this was added ESBO, which was reacted at 180° C. for 6 hours. The final polyol had an acid number of 6.3, epoxy content of 0.5%, and OH number of 95.

Sample F4—In an open reaction vessel mix: 50 grams ricinoleic acid (commercial Castor Oil) and 70.6 grams Epoxidized Soybean Oil (ESBO). The molar epoxy per acid ratio is 1:0.5. The mixture was heated to 170° C. for 16 hours under constant mixing (250 rpm).

Sample F5—In an open reaction vessel mix: 50 grams linoleic acid (commercial) and 79.7 grams ESBO. The molar epoxy per acid ratio was 1:0.5. The mixture was heated to 170° C. for 28 hours under constant mixing (250 rpm).

Sample F6—Bodied Soybean Oil (BSBO) was synthesized by reacting soybean oil (SBO) (about 600 g) and 2% by wt (based on SBO) anthraquinone (catalyst) in a Parr reactor heated to 300° C. for 3.5 hours. The catalyst was removed from the product by centrifugation. Hydrolyzed bodied soybean oil (HBSBO) was synthesized by reacting 250 grams of BSBO and 500 grams distilled water in an open well-mixed batch reactor. About 0.5-1.0 gram of *C. rugosa* lipase powder was added to the reaction at 40° C. for 3 days or until 47.3% hydrolysis of the BSBO (Acid #=89.8) was obtained. HBSBO was collected and separated from the reaction products by centrifugation. Then, in a closed reaction vessel mix: 50 grams HBSBO and 7.4 grams 1,2-epoxybutane. The molar epoxy per acid ratio was 1:0.7. The mixture was heated to 170° C. for 20 hours under constant mixing (250 rpm).

Sample F7—The same as F6 except that the molar epoxy per acid ratio was 1:0.5 where 10.3 grams of 1,2-epoxybutane was added to 50 grams of HBSBO.

The properties of these soy-based polyols are summarized in Table 15. They were tested in the flexible foam recipe of Table 16. The properties of the foam are summarized in Table 17. These results indicate the successful synthesis of these polyols and use in a flexible foam formulation.

TABLE 15

Summary of soy-based polyols prepared for flexible foam formulation.

| | Acid No. | OH No. | Epoxy Content % | η (cP) |
|---|---|---|---|---|
| F1 | 7.08 | 97.7 | 0.57 | 3075 |
| F2 | 4.58 | 101.3 | 0.59 | 5570 |
| F3 | 6.27 | 95.0 | 0.48 | 3606 |
| F4 | 2.8 | 149.3 | 0.58 | 12540 |
| F5 | 1.4 | 145.1 | 0.67 | 7786 |
| F6 | 2.8 | 138.5 | <0.1 | 230.9 |
| F7 | 8.4 | 187.9 | 1.13 | 118.7 |

TABLE 16

Foam recipe used to make foams from soy-based polyols of Table 15

| Ingredients | Parts by weight |
|---|---|
| B-side materials | |
| VORANOL ® 4701 | 50 |
| Vegetable Oil based Polyol | 50 |
| DABCO ® 33-LV ® | 0.6 |
| DABCO ® BL-17 | 0.2 |
| DABCO ® DC 2585 | 1.0 |
| Diethanolamine | 2.2 |
| Stannous Octoate | 0.3 |
| Dibutyltin Dilaurate | 0.3 |
| Blowing Agent (distilled water) | 5.0 |
| A-side material | |
| PAPI ® 27 | Index 80 |

TABLE 17

Properties of foam produced from Soy-based polyols of Table 15.

| | OH Value | Iso Index | Density ($kg/m^3$) | CFD 50% Deflection (kPa) | CDC 50%, $C_t = [(t_o - t_f)/t_o] \times 100$ | Tear (N/m) | Resilience (%) |
|---|---|---|---|---|---|---|---|
| F1 | 104.7 | 80 | 51.4 | 16.13 | 27.29 | 172.8 | 28.0 |
| F2 | 105.9 | 80 | 42.4 | 13.59 | 32.41 | 192.3 | 27.6 |
| F3 | 105.0 | 80 | 59.7 | 22.66 | 32.08 | 200.7 | 27.0 |
| F4 | 152.1 | 80 | 38.4 | 17.87 | 43.43 | 167.9 | 22.3 |
| F5 | 120.1 | 80 | 45.8 | 12.15 | 28.30 | 169.2 | 35.3 |
| F6 | 141.3 | 80 | 46.2 | 12.43 | 35.06 | 159.4 | 28.0 |
| F7 | 196.3 | 80 | 37.4 | 8.59 | 44.46 | 141.5 | 24.3 |

Example 11

Bodying of Soybean Oil Including Binder Applications

In this example, 9-10 Anthraquinone was used as a catalyst while dicylopendatiene and divinylbenzene were used as cross-linkers to promote the formation of oligomers that can be functionalized to form B-side prepolymers. These oligomers preferably have an average molecular weight of between 900 and 20,000, and more preferably between 1300 and 5,000. The oligomers themselves have multiple applications, including use as precursors for functionalizing, use as prepolymers, and use as binders.

The combination of time and temperature was sufficient to body soybean oil as is illustrated by the data of Table 18. Indications of the bodying reaction include a decrease in iodine number (starting at 134-135 with soybean oil) and an increase in viscosity (starting at about 52 with soybean oil). The data of Table 19 illustrate how 9-10 Anthraquinone allows the use of lower temperatures to achieve viscosities (degrees of polymerization) that are very difficult to obtain in the absence of a catalyst. The lower temperatures tend to preserve the quality of the bodied soybean oil where quality is indicated by lower odor and less color.

TABLE 18

Impact of temperature and residence time in flow reactor on bodying of soybean oil in the absence of catalyst or cross-linker.

| Samples | Temperature (° C.) | Flow rate mL/s | Retention time (min) | Iodine No. | Acid No. |
|---|---|---|---|---|---|
| B1 | 350 | 0.1 | 83.3 | 109.1 | 19.1 |
| B2 | 350 | 0.1 | 83.3 | 106.9 | 18.1 |
| B3 | 350 | 0.1 | 83.3 | 105.9 | 19.8 |
| B4 | 350 | 0.043 | 193.8 | 100.9 | 26.3 |
| B5 | 350 | 0.043 | 193.8 | 103.6 | 21.2 |
| B6 | 350 | 0.089 | 93.7 | 99.6 | 22.3 |
| B7 | 350 | 0.089 | 93.7 | 101.7 | 21.5 |

All bodied products had a viscosity of about 68 cP.

Note:

Reactor Volume 500 ml.

Note:

viscosity did not have a significant change.

TABLE 19

| Impact of 9-10 Anthraquinone on bodying of soybean oil in a batch reactor. | | | | | |
|---|---|---|---|---|---|
| Sample | Temperature (° C.) | Time (hrs) | Iodine No | Acid No. | Viscosity mPa-s (cP) |
| SBO no rxn. | — | — | 135 | 5 | 52 |
| BSBO no catalyst | 330 | 1 | 100 | 15 | 68 |
| BSBO catalyzed with AQ | 260 | 6 | 104 | 15 | 253 |
| BSBO catalyzed with AQ | 280 | 6 | 91 | 15 | 1158 |
| BSBO catalyzed with AQ | 300 | 6 | 70.5 | 15 | 2998 |

Note:
Catalyst: 9-10 Anthraquinone was using 2.5 to 5% wt. Reactor volume 2 liter.

Experiments were preformed to understand how dicylopendatiene and divinylbenzene cross-linkers further increase the crosslinking, leading to the formation of soft to very hard solids. The conditions were more severe than desired for oligomer formation. Soybean oil was first mixed with varying amounts divinyl benzene, dicyclopendaiene dimer, and boron triflouride diethyl ether complex to form a prepolymer. The mixture was heated at 120° C. in an oven for about 18 hours. Tables 21 through 23 illustrate the impact of the crosslinkers and boron trifluoride catalyst on promoting reaction at lower temperatures.

TABLE 20

| Effect of varying dicylopendatiene and divinylbenzene amounts on the final polymer. | | | | |
|---|---|---|---|---|
| SBO (g) | Dicyclo-pentadiene (g) | Divinyl-benzene (g) | Boron Trifluoride (g) | Appearance & State |
| 6.506 | 0 | 3.011 | 0.5 | Hard |
| 6.501 | 0.501 | 2.501 | 0.505 | Very Hard |
| 6.501 | 1.003 | 2.008 | 0.507 | Hard |
| 6.501 | 1.5 | 1.503 | 0.502 | Hard |
| 6.5 | 2.003 | 1.002 | 0.516 | Hard |
| 6.501 | 2.5 | 0.5 | 0.508 | Soft & Rubbery |
| 6.5 | 3 | 0 | 0.509 | Very Soft & Rubbery |

TABLE 21

| Effect of divinyl benzene amount on final polymer properties. | | | | |
|---|---|---|---|---|
| SBO (g) | Dicyclo-pentadiene (g) | Divinyl-benzene (g) | Boron Trifluoride (g) | Appearance & State |
| 7.002 | 0 | 3.004 | 0.515 g | Very Hard |
| 7.5 | 0 | 2.51 | 0.523 g | Hard |
| 8.019 | 0 | 2.01 | 0.522 g | Soft |
| 8.507 | 0 | 1.506 | 0.504 g | Soft |
| 9 | 0 | 1.007 | 0.502 g | Soft & Rubbery |
| 9.504 | 0 | 0.505 | 0.532 g | Very Soft |

TABLE 22

| Effect of catalyst on final polymer properties. | | | | |
|---|---|---|---|---|
| SBO (g) | Dicyclo-pentadiene (g) | Divinylbenzene (g) | Boron Trifluoride (g) | Appearance & State |
| 6.507 | 0 | 3.012 | 0.52 | Very Hard |
| 6.504 | 0 | 3.008 | 0.42 | Very Hard |
| 6.505 | 0 | 3 | 0.3 | Very Hard |
| 6.503 | 0 | 3.018 | 0.2 | Hard |
| 6.506 | 0 | 3.005 | 0.1 | Hard |
| 6.505 | 0 | 3.001 | 0.05 | Soft |

Example 12

Synthesis of B-Side Components Synthesized with Functionalizing Triglyceride Followed by Bodying An epoxy-containing intermediate was produced by epoxidizing about 25% of the carbon-carbon pi-bonds in soybean oil. The mixture was then reacted (bodied) in a one-liter Erlenmeyer flask with a nitrogen purge at atmospheric pressure at a temperature of 325° C. Tables 23 and 24 show conversion versus time where conversion was determined by following the iodine number and viscosity. Acid number, epoxy content, and OH number were also followed.

TABLE 23

| Bodying of epoxy containing intermediate at 325° C. | | | | | |
|---|---|---|---|---|---|
| Time (min) | Acid No. | Iodine No. | Viscosity (cP) | % Epoxy Content | OH No. |
| 0 | 1.03 | 114.5 | 73 | 2.11 | 0 |
| 15 | 4.59 | 107.4 | 201 | 0.78 | |
| 30 | 5.89 | 103.9 | 372 | 0.53 | |
| 45 | 6.50 | 101.5 | 497 | 0.34 | |
| 60 | 6.95 | 99.5 | 712 | 0.26 | 55.8 |
| 90 | 8.01 | 99.6 | 1473 | 0.13 | 50.4 |
| 120 | 8.00 | 93.8 | 2855 | 0.13 | 46.5 |
| 150 | 8.25 | 93.2 | 5678 | 0.11 | |
| 180 | 8.20 | 90.1 | 12140 | 0.09 | |
| 210 | 7.35 | 89.1 | 26140 | 0.08 | |
| 240 | 7.98 | 89.1 | 42200 | 0.07 | |

TABLE 24

| Bodying of epoxy containing intermediate at 325° C. | | | | | |
|---|---|---|---|---|---|
| Time (min) | Acid No. | Iodine No. | Viscosity (cP) | % Epoxy Content | OH No. |
| 60 | 3.84 | 87.40 | 1319 | 0.184 | 47.69 |
| 180 | 4.09 | 86.48 | 14183 | 0.057 | 84.64 |
| 90 | 4.02 | 84.20 | 5431 | 0.179 | 73.56 |
| 60 | 8.90 | 97.8 | ~900 | 0.095 | — |
| 75 | 7.44 | 94.95 | ~1000 | 0.125 | — |
| 90 | 8.05 | 86.04 | 1504 | 0.122 | 31.40 |
| 90 | 8.0 | 83.03 | 2005 | 0.154 | 59.62 |
| 150 | 6.95 | 81.01 | 2317 | 0.086 | 57.77 |

These data indicate that epoxy groups react to form alcohol groups and that viscosity increase with increasing time. The increasing viscosity and decreasing iodine number substantiate a mechanism that includes bodying. An epoxy group will react with an alcohol group to form a single functional alcohol, and so, the final alcohol content is not directly proportional to the initial epoxy content. Optionally, multi-functional alcohols like ethylene glycol may be added to the mix to as primary alcohol functionality.

Some of these polyols produced flexible and/or rigid foams when used with equal parts of a petroleum-based polyol. These foams demonstrated the reactivity of these polyols in urethane formulations.

Example 13

Synthesis of Soy-Based Polyol: Epoxidation Followed by Catalyzed Alcoholysis In this study, soy-based polyol was produced in one reactor by this sequence: epoxidation reaction, separation process and alcoholysis reaction. Full and partial epoxidized soybean oils were developed by different molar ratios of formic acid and hydrogen peroxide used in the reaction. Partial epoxidized soybean oil was formed with molar ratio of 1:0.4:0.7 ($SBO:FA:H_2O_2$) obtaining a yield of 93%. Alcoholysis reaction using 4% by wt. of ethylene glycol and 0.5% by wt. of p-toluenesulfonic acid was effective to increase the reactivity of the partial epoxidized soybean oil and increase the hydroxyl number around 100 in the soy-based molecule. FT-IR and $^1H$-NMR characterization of different samples were evaluated. A phosphate ester forming-reaction was carried out by mixing epoxidized soybean oil with up to 1.5% o-phosphoric acid. In situ oligomerization took effect almost instantly producing a clear, homogeneous, highly viscous, and a low-acid product with a high average functionality. The resulting epoxide was used as a reactant for urethane bioelastomer synthesis and pre-evaluated for rigid foam formulation. Results have shown that with a number of catalysts tested phosphoric acid significantly enhances a solvent-free oxirane ring cleavage and polymerization of the epoxidized soybean oil via phosphate-ester formation at room temperature. The resulting phosphoric acid-catalyzed epoxide-based bioelastomer showed decreased extractable content for up to five times and increased tensile strength at the same isocyanate loading relative to the non-catalyzed epoxide. With the same catalyzed epoxide used as a B-side reactant in the rigid foam formulation, the amount of isocyanate can be reduced to about 40% compared with the non-catalyzed epoxide reactant.

Figure 8:
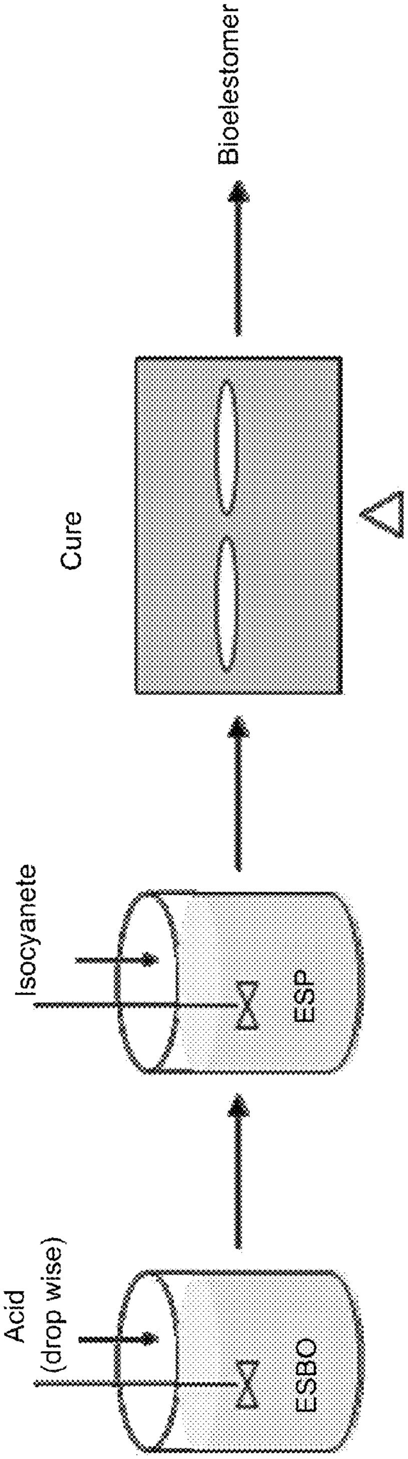
FIG. 8 illustrates an acid-promoted oligomerization process.

In this work, an urethane bioelastomer formulation is studied following epoxide-substituted polyol (ESP) and polymeric diphenylmethane diisocyanate (pMDI) interaction, including physico-chemical characterization of the elastomer products. In the first part, catalysts were evaluated to specifically promote epoxide reaction and o-phosphoric acid has shown significant effect in lowering the oxirane concentration of the epoxide even at room temperature with no solvents added. A simplified scheme of the process is shown in FIG. 8. ESP is made to react in an open glass vessel with the acid catalyst added drop wise until a homogeneous phase is obtained. Proper mixing is crucial in attaining a uniformly-catalyzed product. After completion of reaction, pMDI is added to ESP and the product degassed, then postcured in a convection oven. Bioelastomer products obtained display different phases ranging from viscous and tacky to hard and brittle which are attributed mainly to isocyanate index used and hydroxyl equivalent weight of the ESP.

This Example presents the study of full and partial epoxidation of soybean oil by varying the amount of the reactants without any heterogeneous catalysts or any solvents in the reaction. Separation process after epoxidation reaction followed by the alcoholysis reaction of the epoxy moieties using ethylene glycol and p-toluenesulfonic acid were done to produce hydroxyl functionalities in the soybean oil molecule. The main purpose of this work was to create a soy-based polyol by epoxidation reaction followed by epoxy-ring opening reaction using an alcohol to attach most of alcohol groups possible in the final product.

One of the main objectives of the ESP work were 1) developing catalyst formulation to specifically promote solventless epoxide reaction in ESP and effectively replace substantial amount of the polyol, and 2) developing urethane bioelastomer formulation using ESP to reduce total isocyanate content. Acid, hydroxyl, oxirane values, and viscosity of the ESP were measured to evaluate the effect of o-$H_3PO_4$ on ring-opening hydrolysis and oligomerization of the monomers. Results showed that reduction of oxirane concentration and increases in hydroxyl value of the final ESP were dependent on the amount of o-$H_3PO_4$ added. Change in acid value was considerably small. Extractability tests showed that bioelastomers containing o-$H_3PO_4$-catalyzed ESP gave much lower unreacted oil extractability than those without and FTIR tests revealed their difference in polymeric structure.

a) Experimental Materials

Soybean oil (RBD grade, Iodine no. 127-130 mg $I_2$/g) was obtained in a local grocery store. Formic acid (88 wt %), hydrogen peroxide (30 wt % aqueous solution), p-toluenesulfonic acid monohydrate (98 wt %) and ethylene glycol (99 wt %, HPLC grade), o-phosphoric acid (85 wt %) were purchased from Sigma (St. Louis, Mo.). Epoxidized Soybean Oil (Vikoflex®7170, ESBO-7.0% oxirane content) from Arkema Co.(Praire, Mn.), polymeric diphenylmethane diisocyanate (MDI, PAPI® 27) 31.4 wt % NCO from Dow Chemical and castor oil from Alnor Oil.

Figure 9:
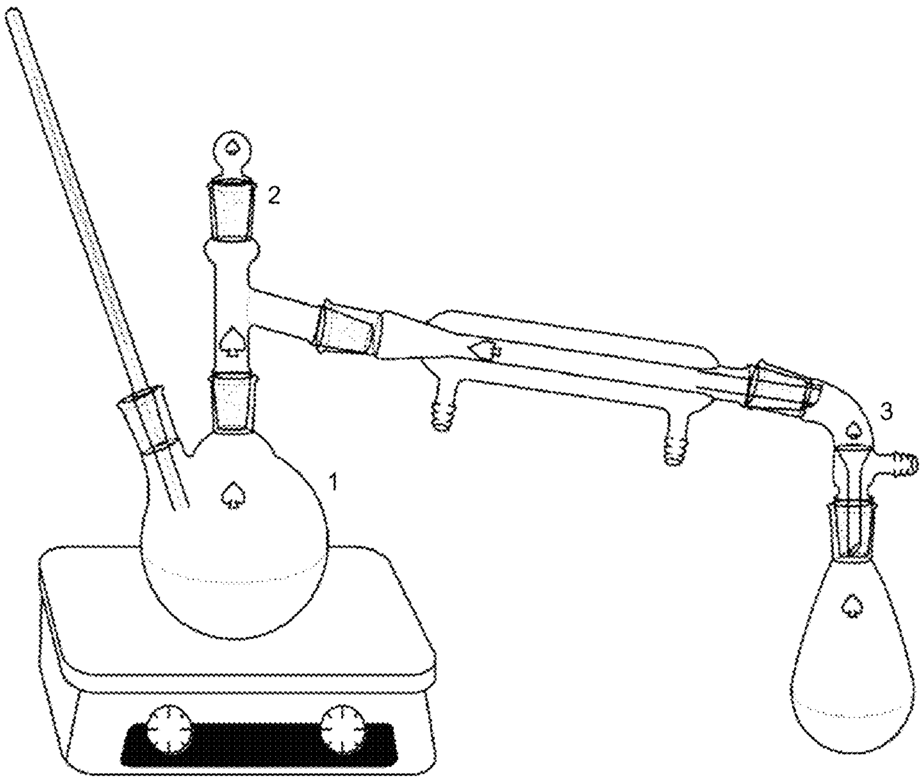
FIG. 9 diagrams the reaction and distillation system.

Epoxidation reaction. An epoxidation reaction was carried out in a two-necked round-bottom flask of 500 mL over a hot plate with a thermometer and condenser connected with a 100 mL round flask as a collector for product distillation, as shown in FIG. 9. Soybean oil and formic acid were placed in the two-necked round-bottom flask of 500 mL with a magnetic stirrer. Hydrogen peroxide (30% aq. Soln.) was poured slowly into the flask for about 30 minutes. The reaction was heated at 40° C. and stirred at 300 rpm for 30 hours of reaction. The amounts of the reactants were determined in terms of the epoxy content or epoxidation degree desired. Partial and full epoxidized soybean oil was estimated at 5.0 and 7.0% of epoxy content, respectively. Different molar ratios were evaluated as illustrated in Table 25.

After the reaction was completed, the resultant hydrogen peroxide and formic acid was distilled at 100° C. for about 4 hours or until the water was removed from the oil sample. A vacuum pump was connected into the system to enhance the distillation process as illustrated on FIG. 9.

Alcoholysis Reaction. Ethylene glycol (4% by weight based on soybean oil) and p-toluenesulfonic acid (0.5% by weight) were poured into the round-bottom flask with the epoxidized soybean oil previously prepared. The reactants were heated at 150° C. for about 7 to 10 hours of reaction.

Synthesis of epoxide-substituted polyol (ESP). Full epoxidized soybean oil was reacted with 0.5-2.0% o-$H_3PO_4$ added drop wise in a beaker under vigorous mechanical stirring at room temperature. A homogeneous and highly viscous product is obtained after mixing for 5 minutes. The next step was the preparation of a series of ESPs by varying the amount of the acid-catalyzed ESBO in castor oil. This was done by moderately mixing the catalyzed ESBO and castor oil at room temperature until a homogeneous ESP is obtained.

Preparation of urethane bioelastomers. Two types of bioelastomers were prepared, ESPs using only 0.5% o-$H_3PO_4$ and acid-catalyzed ESBO using 0.5-2.0% o-$H_3PO_4$ without castor oil. The preparation procedure of ESP-made bioelastomer consists of the following steps: (1) Mixing 5.0 g ESP and 2.5 g pMDI in a 50-mL beaker on a hotplate equipped with stirrer. Careful stirring must be done to obtain uniform phase and consistency and also avoid bubble formation. Stirring is done at room temperature. (2) Placing the samples in a 7 cm×11 cm rectangular plastic mold and degassed for 10 mins at 45° C. vacuum oven to get rid of $CO_2$, air trapped, or gases evolved during reaction; 3) Postcuring samples for about 48 h at 45° C. oven with no vacuum applied. Extractability of unreacted oil phase of the finely-cut samples is measured after 48 h of curing. The second type of bioelastomers is prepared the same way but the amount of o-$H_3PO_4$ is varied (0.5, 1.0, 1.5%) and no alcohol source (castor oil) is added. Polymeric MDI was added at 15% and 25% by weight of the acid-reacted ESBO. After postcure, dumbbell-shaped specimens are cut out from bioelastomer samples using an ASTM D638 Type V cutter.

Analytical Methods for Polyols. The final product was analyzed for acid number, iodine number, hydroxyl number, epoxy content and dynamic viscosity. The acid number (mg KOH/g sample) indicates the number of carboxylic acid functional group per gram of a dry sample, according to the AOCS official method (AOCS Te 1a-64 1997). The iodine value characterizes the concentration of carbon-carbon double bonds (unsaturation) according to ASTM D1959-97. The hydroxyl number (mg KOH/g sample) is defined as the milli grams of potassium hydroxide equivalent to the hydroxyl content per gram of sample according to AOCS official method (AOCS Tx 1a-66 1997). The epoxy content percent of a dry sample is analyzed by AOCS method Cd 9-57 (1997), oxirane oxygen in epoxidized materials. The dynamic viscosity of the samples was measured in centipoises (cP) at 22° C. using a Model RS100 Rheometer made by Haake-Thermo-electron.

Characterization of ESPs and bioelastomers. Tensile properties of the bioelastomers were determined by a TA.HDi Texture Analyzer (Texture Technologies Corp., Scarsdale, N.Y.) following ASTM Procedure D 882-02. DSC measurements were carried out on a TA Instruments (New Castle, Del., USA) DSC Q100. All the DSC measurements were performed following the ASTM E 1356-03 standard. About 10 mg of the bioelastomer samples were heated at a rate of 10° C./min from −60° C. to +100° C. under dry nitrogen gas atmosphere.

Characterization Analyses for Polyols. A Fourier transforms infrared spectroscopy (FT-IR; Thermo Scientific Nicolet 4700) equipped with Smart Detectors™ and multiple spectral range capability was used to characterize the functional groups of the bioelastomers and soy-polyols. The sample was pressed against ATR diamond to have a good contact and a total of 64 scans from 4000-400 $cm^{-1}$ wavenumber range were obtained at a resolution of 4 $cm^{-1}$.

A proton nuclear magnetic resonance spectroscopy ($^1H$-NMR) analysis was used to evaluate the chemical structure of the polyols. All $^1H$-NMR spectra were recorded in $CDCl_3$ using a Varian Unity spectrometer at 300 MHz (Palo Alto, Calif.).

Extractability test. A single-step unreacted oil phase extraction method was used to determine the extent of polymer crosslinking between pMDI and epoxides. Polymeric MDI and the sample epoxide in a specified weight ratio were well mixed in a small disposable aluminum pan. The resulting elastomeric wafer product was left to cure for 24 hours in a convection oven at 140° C. in the case of samples evaluated for catalyst performance and 48 hours/45° C. in the case of final bioelastomers tested. The cured wafer samples were then cooled to room temperature and cut into thin sheets for unreacted oil extraction. About a gram of each cut sample was soaked with occasional stirring in a 1:4 by volume n-hexane-cyclohexanol solution for 15 minutes after which the mixture is filtered. Both permeate and retentate were dried in a vacuum oven at 110° C. for 2 hours. The percentage of unreacted oil phase was calculated by mass balance. This test is a straightforward reaction of epoxides and pMDI. This basic polymerization reaction is described elsewhere (see Herrington, Flexible Polyurethane Foams, $2^{nd}$ Ed, 1997, The Dow Chemical Company, Freeport, Tex.).

b. Experimental Results

Figure 10:
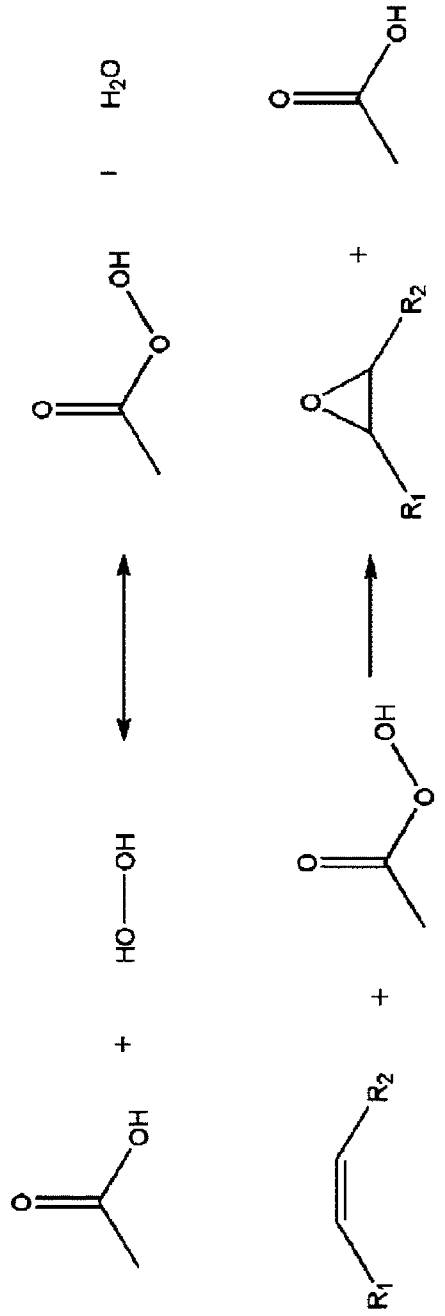
FIG. 10 presents general epoxidation reaction mechanisms.

Epoxidation Reaction. In the epoxidation reaction there are two main reactions involved: peroxoacids formation and epoxy groups formation. The first reaction is an acid-catalyzed formation of peroxoformic acid from formic acid and hydrogen peroxide, while the second reaction is the uncatalyzed epoxidation of unsaturated soybean oil with the peroxoformic acid formed previously, shown in FIG. 10. Simultaneous side reactions such as epoxy ring opening followed by dimerization of hydroxy or acetoxy compounds previously formed may precede (illustrated in FIG. 11).

TABLE 25

The mole ratio of the reactants used in the epoxidation reaction.

| mole ratio | | |
|---|---|---|
| Soybean Oil | Formic Acid | Hydrogen Peroxide |
| 1 | 0.5 | 1.2 |
| 1 | 0.5 | 0.9 |
| 1 | 0.5 | 0.8 |
| 1 | 0.5 | 0.4 |
| 1 | 0.5 | 0.7 |
| 1 | 0.4 | 0.7 |
| 1 | 0.2 | 0.7 |
| 1 | 0.1 | 0.7 |

As mentioned in the experimental procedure, different molar ratios of formic acid and hydrogen peroxide were used in the epoxidation reaction of soybean oil, illustrated in Table 25. Table 26 shows the results obtained in the epoxidation reaction with the different concentrations of the reactants. In our calculations, we estimate a partially epoxidized soybean oil (PESBO) with an epoxy content of 4.90%. In most of the previous work, the hydrogen peroxide was used in excess (25 to 50% by mole) to avoid side reactions during the reaction and obtain a 100% conversion. Table 27 illustrated the full epoxidation reaction results of soybean oil at different molar ratios of hydrogen peroxide and the properties of each ESBO product after the distillation process for water and acid removal.

TABLE 26

Results for the partial epoxidized soybean oil for different molar ratios of soybean oil (SBO), formic acid (FA) and hydrogen peroxide ($H_2O_2$).

| | Molar Ratio | | | PESBO Product | | |
|---|---|---|---|---|---|---|
| | | | | Epoxy Content | Acid no. | Yield |
| no. | SBO[a] | FA | $H_2O_2$ | (%) | (mg KOH/g) | (%) |
| 1 | 1 | 0.5 | 0.4 | 3.09 | 23.60 | 63.06 |
| 2 | 1 | 0.5 | 0.7 | 4.67 | 16.13 | 95.31 |
| 3 | 1 | 0.4 | 0.7 | 4.85 | 25.00 | 98.98 |
| 4 | 1 | 0.2 | 0.6 | 4.65 | 7.80 | 94.90 |
| 5 | 1 | 0.2 | 0.7 | 4.70 | 5.40 | 95.92 |
| 6 | 1 | 0.1 | 0.7 | 4.00 | 3.50 | 81.63 |

[a]Molar ratio based on the double bond present in the soybean oil (functionality of 4.6).

Lower molar ratio of formic acid used in the reaction resulted in a low acidity product, as illustrated in the Table 26 and 27. It is possible to decrease the amount of formic acid to half for partial epoxidized soybean oil production and 0.8 mole ratio for full epoxidized soybean oil for a 94% yield or higher. The low acid numbers indicate that no side reaction occurs during the epoxidation reaction. The formation of hydroxyl groups during the epoxidation reaction are desired for future applications studies. One of the objectives is to create a soy-molecule with high hydroxyl group content by epoxidation reaction followed by epoxy ring opening reaction using an alcohol to attach most of alcohol groups as possible.

TABLE 27

Results for the full epoxidation reaction of soybean oil (SBO) with different molar ratios of hydrogen peroxide ($H_2O_2$) and the final properties after the water and acid removal (distillation process).

| | mole ratios | | | Properties of ESBO | | | Distill | Final Properties of ESBO | | |
|---|---|---|---|---|---|---|---|---|---|---|
| | | | | Epoxy | Acid | Yield | 100° C. | Epoxy | Hydroxyl | Iodine |
| # | SBO[a] | FA | $H_2O_2$ | (%) | no. | (%) | 4 hrs | (%) | no.[b] | no. |
| 1 | 1 | 0.5 | 1.2 | 7.10 | 1.00 | 101.43 | | 6.80 | 8.05 | 1.50 |
| 2 | 1 | 0.5 | 1.2 | 6.68 | 1.30 | 95.43 | | 6.68 | 6.55 | 1.30 |
| 3 | 1 | 0.5 | 0.9 | 6.45 | 2.00 | 92.14 | | 5.01 | 67.22 | 5.00 |
| 4 | 1 | 0.5 | 0.9 | 6.78 | 1.50 | 96.86 | | 6.78 | 7.63 | 1.50 |
| 5 | 1 | 0.5 | 0.8 | 6.80 | 2.00 | 97.14 | | 5.50 | 31.04 | 11.00 |
| 6 | 1 | 0.5 | 0.8 | 6.89 | 2.00 | 98.43 | | 5.60 | 42.47 | 10.00 |

[a]Molar ratio based on the double bond present in the soybean oil (functionality of 4.6).
[b]AOCS method for hydroxyl number.

Figure 11:
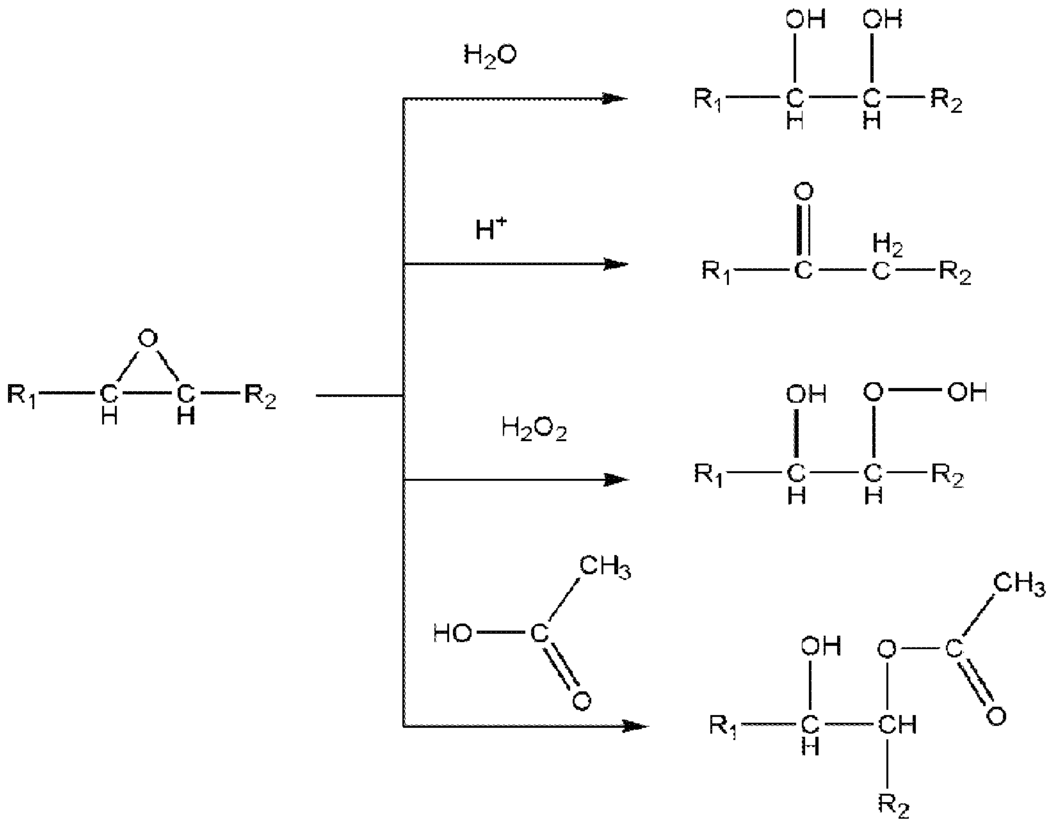
FIG. 11 illustrates possible side reactions of an epoxy group.

To remove all the water and the acid content in the reaction vessel, the system was connected to a vacuum pump and heated at 100° C. for 3 to 4 hours for distillation process. Table 27 demonstrates the results before and after distillation process for full epoxidized soybean oil. A reduction in the epoxy content caused by the heat applied to the system indicates the formation of alcohol groups in the sample. In theory, if one epoxy-ring was opened, it will form at least one hydroxyl group and a substituent group in the molecule, as shown in FIG. 11. The little increment in the iodine number can results due to the heat in combination with the formic acid present to form an alkene compound, illustrated in FIG. 12.

Table 28 shows the results of partial epoxidized soybean oil samples after water and acid removal by distillation process. Partial epoxidized soybean oil shows the same characteristic behavior for epoxy-groups opening during the distillation process that the full epoxidized soybean oil was observed before, as shown in Tables 26 and 28. Most of the samples show a reduction in the acid number before the distillation process suitable by the reaction between the epoxy and acid groups. The amount of formic acid used in the epoxidation varies directly with the alcohols groups formed during the distillation process. As the molar ratio of formic acid decreases the hydroxyl number decrease, it is a proportional variable for this property. Moreover, the amount of formic acid used in the epoxidation reaction also determines the acidity in the sample after the reaction.

TABLE 28

Final properties of partial epoxidized soybean oil after water and acid removal (distillation process at 100° C. for 4 hours).

| | Molar Ratio | | | Final Properties | | | |
|---|---|---|---|---|---|---|---|
| | | | | Epoxy content | Acid no. (mg | Iodine no. | Hydroxyl no.[b] (mg |
| # | SBO[a] | FA | $H_2O_2$ | (%) | KOH/g) | (mg $I_2$/g) | KOH/g) |
| 1 | 1 | 0.5 | 0.4 | 1.88 | 8.20 | 26.50 | 49.22 |
| 2 | 1 | 0.5 | 0.7 | 3.08 | 4.08 | 25.40 | 41.47 |
| 3 | 1 | 0.4 | 0.7 | 3.80 | 4.10 | 22.40 | 34.21 |
| 4 | 1 | 0.2 | 0.6 | 3.22 | 3.85 | 22.50 | 33.45 |
| 5 | 1 | 0.2 | 0.7 | 3.73 | 2.40 | 23.22 | 21.51 |
| 6 | 1 | 0.1 | 0.7 | 3.54 | 2.40 | 27.10 | 16.81 |

[a]Molar ratio based on the double bond present in the soybean oil (functionality of 4.6).
[b]AOCS method for hydroxyl number.

Figure 12:
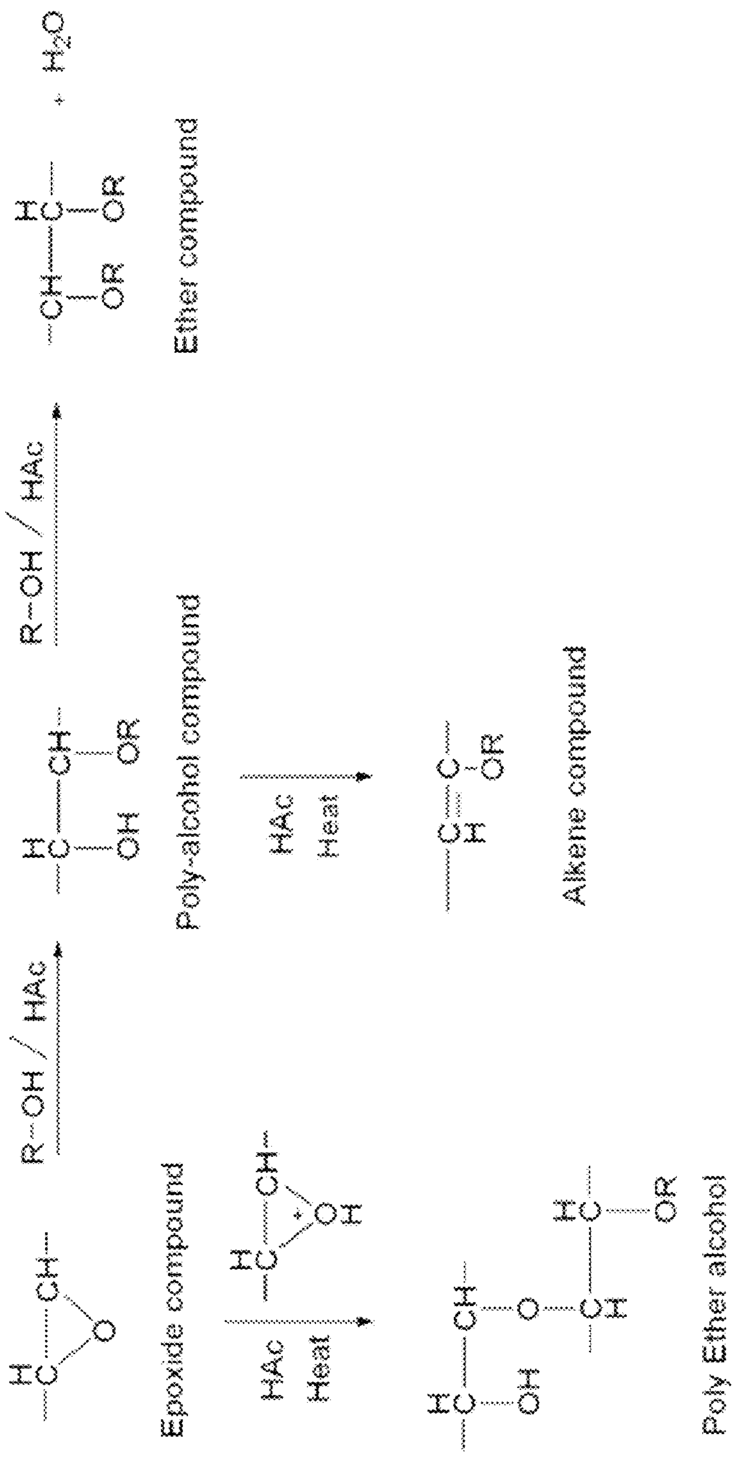
FIG. 12 diagrams general mechanisms for the epoxy-ring opening hydrolysis reaction (R—OH is an alcohol and HAc is an acid).

Alcoholysis Reaction of PESBO. To increase the reactivity of the partial epoxidized soybean oil (PESBO), ethylene glycol was added as a co-reagent into the ring-opening hydrolysis reaction of PESBO. Ethylene glycol is relatively inexpensive and has a high hydroxyl number, 1807 mg KOH/g. A general reaction mechanism for epoxy-ring opening hydrolysis of oxirane-containing compound with an alcohol compound followed by glycol formation and alcohol dehydration producing ethers and alkenes are shown in FIG. 12.

Ethylene glycol acts as a nucleophile with the p-toluenesulfonic acid monohydrate in the hydrolysis reaction forming equivalent hydroxyl functionalities in the final soy-polyol. The increases of hydroxyl numbers are showed in Tables 28 and 29 for each sample, respectively. Insignificant changes in the iodine number were observed before and after alcoholysis reaction, as illustrated in Tables 28 and 29. This behavior indicates that the reaction undergo an ether and alcohol formation route rather than the alkene formation route. Also, the viscosity for each sample has increased gradually relative to the viscosity of the starting material (soybean oil ~80 cP).

TABLE 29

Results for the alcoholysis reaction of partially epoxidized soybean oil with 4% by wt. of ethylene glycol using 0.5% by wt. of p-toluenesulfonic acid (p-TSA) as catalyst.

| | | | | Rxn Conditions | | Product Properties | | | | |
|---|---|---|---|---|---|---|---|---|---|---|
| | mole ratios | | | Temp | Time | Epoxy | Acid no. | Iodine no. | Hydroxyl no. (mg | Viscosity |
| # | PESBO | EG | pTSA | (° C.) | (hours) | (%) | (mg KOH/g) | (mg $I_2$/g) | KOH/g) | (cP) |
| 1 | 1 | 0.64 | 0.03 | 140 | 6 | 0.37 | 1.05 | 25.40 | 125.90 | 669.72 |
| 2 | 1 | 0.64 | 0.03 | 150 | 5 | 0.38 | 0.98 | 30.50 | 106.20 | 1491.40 |
| 3 | 1 | 0.64 | 0.03 | 140 | 8 | 0.80 | 1.50 | 24.83 | 102.40 | 2407.40 |
| 4 | 1 | 0.64 | 0.03 | 150 | 10 | 0.76 | 0.80 | 34.35 | 99.80 | 1816.80 |
| 5 | 1 | 0.64 | 0.03 | 150 | 6 | 0.93 | 0.90 | 40.50 | 104.40 | 2493.00 |
| 6 | 1 | 0.64 | 0.03 | 150 | 8 | 1.29 | 1.50 | 41.65 | 122.12 | 1635.20 |

Figure 13:
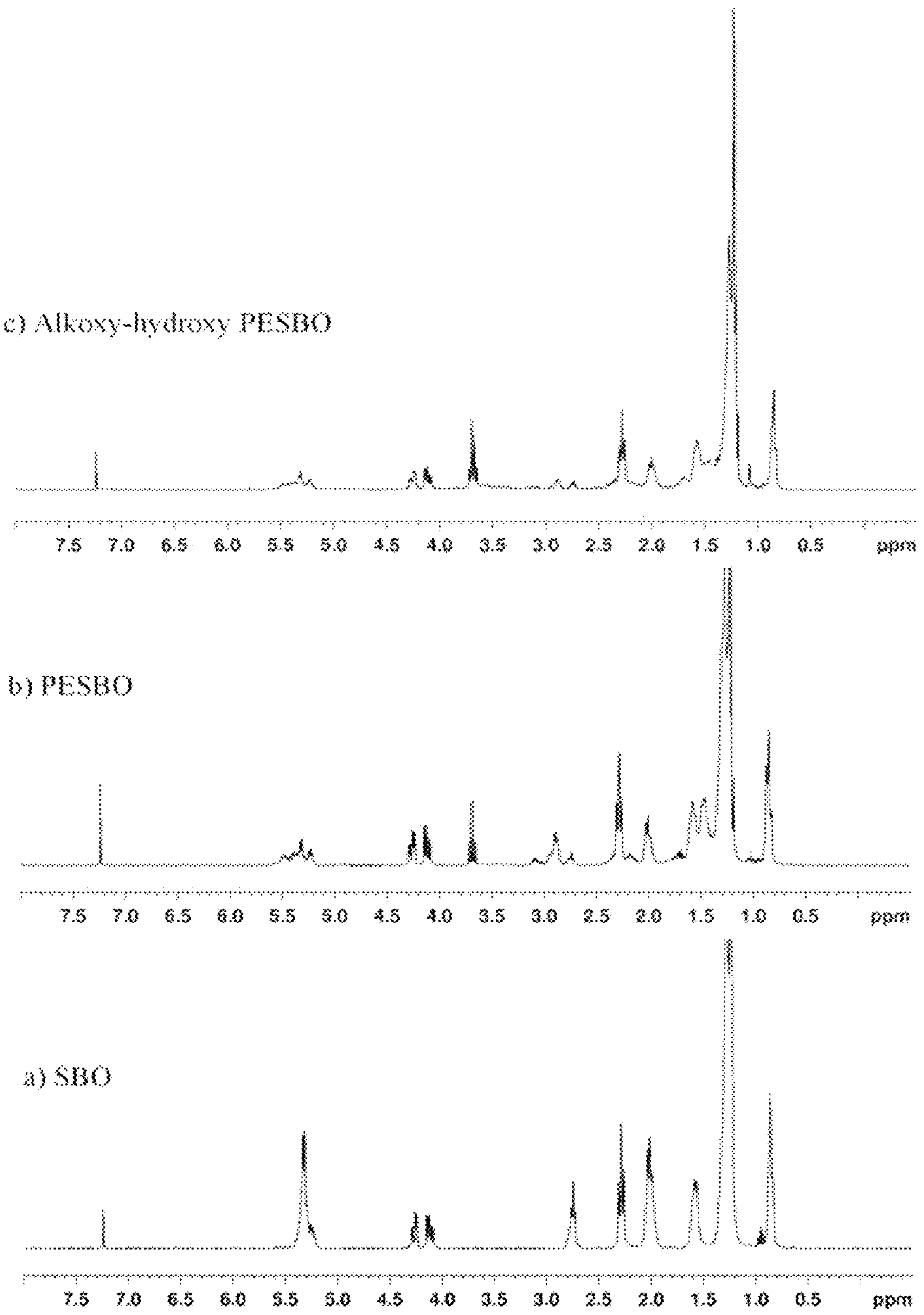
FIG. 13 presents $^1$H-NMR spectra. a) soybean oil (SBO); partial epoxidized soybean oil (PESBO); and c) alkoxy hydroxyl partial epoxidized soybean oil (alkoxy hydroxyl PESBO).

FIG. 13 shows the $^1$H-NMR spectra of soybean oil (a), partial epoxidized soybean oil (b) and alcoholysis of partial epoxidized soybean oil (c), respectively. The triglyceride of soybean oil has approximately 4.5 carbon-carbon double bonds per molecule according to the spectra, shown in FIG. 13(*a*). The three side chains are composed mainly of ~20-30% oleic acid (ester), ~50-80% linoleic acid (ester) and ~5-10% linolenic acid (ester). The structure of partially epoxidized soybean oil is similar to that of the soybean oil, but with relatively low carbon-carbon double bonds (peaks at 2.7-2.8 ppm).

As shown in FIG. 13(*b*), the appearance in the spectra of the peaks at 2.9-3.1 ppm in the partial epoxidized soybean oil implies an epoxy ring formation —CH—CH— and the vinylic protons at 5.23-5.48 ppm nearly disappears. The hydroxyl group formation was confirmed in the $^1$H-NMR spectra for the partial epoxidized soybean oil and the alcoholysis of PESBO in FIG. 13 (*b-c*). In both spectrums, the peaks at 3.6-3.7 ppm were the multiplet signal for the —$CH_2$— in the hydroxyl groups formed in the reactions. Also, the FIG. 13 (*b-c*) shows a reduction in the epoxy ring group and the olefinic protons at 2.9-3.1 ppm and 5.23-5.48 ppm. Lee and co-workers (Korean J. Chem. Engineering, 2008, 25(3):474-482) report a detailed $^1$H-NMR analysis for soybean oil and epoxidized soybean oil samples.

Figure 14:
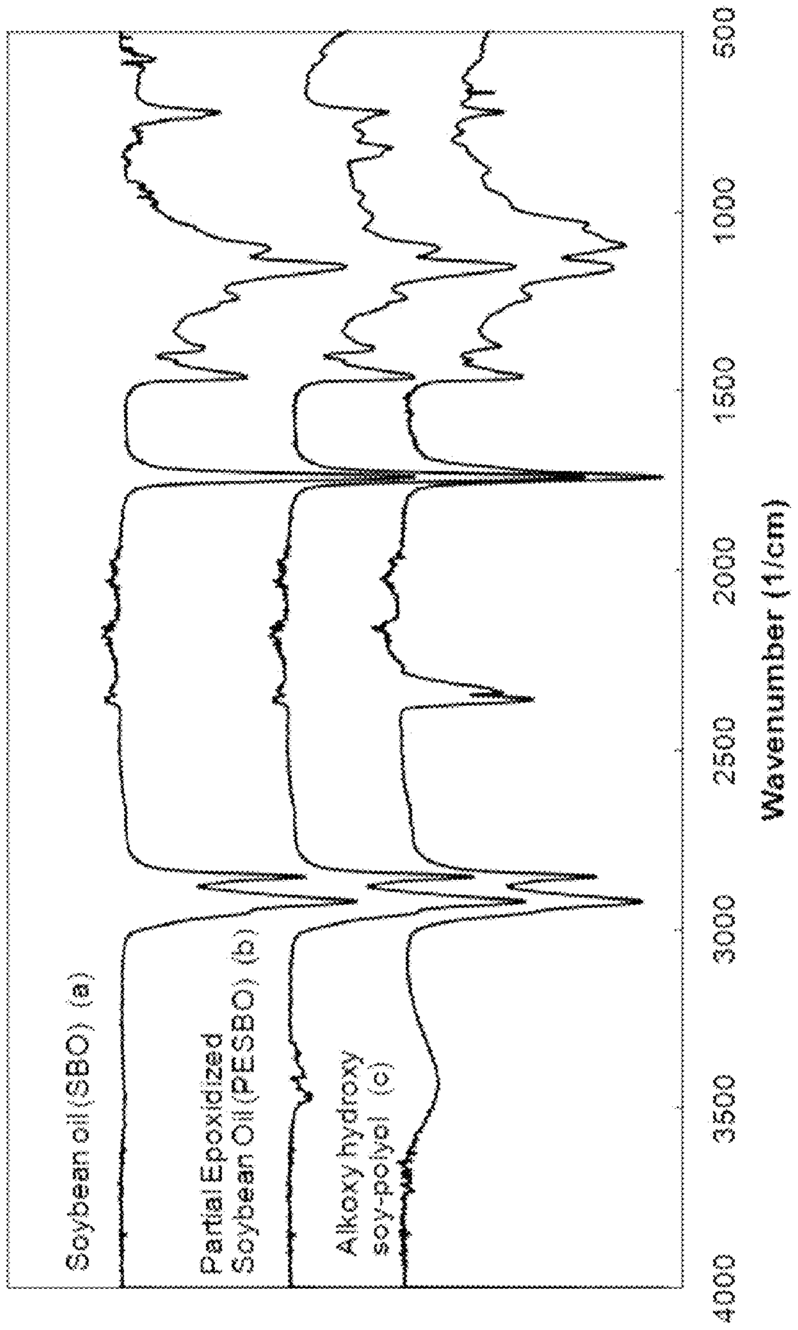
FIG. 14 presents FT-IR spectra. a) soybean oil (SBO); b) partial epoxidized soybean oil (PESBO); and c) alkoxy hydroxyl of partial epoxidized soybean oil (alkoxy hydroxyl soy-polyol).

A FT-IR spectrum of the soybean oil, partially epoxidized soybean oil and the alkoxy-hydroxy PESBO were presented in FIG. 14. The spectra of PESBO (b) shows an appearance of the epoxy group at 825-845 $cm^{-1}$ compared with the starting material, SBO (a) in FIG. 13. The alkoxy hydroxy PESBO (c) shows the characteristic signals at 1050 $cm^{-1}$ indicating the presence of ester groups and the emergence of hydroxyl groups at 3450 $cm^{-1}$. Also, the disappearances of the epoxy groups at 825-845 $cm^{-1}$ are obvious. The FT-IR spectra confirmed the epoxidation reaction and the pathway mechanism illustrated previously in FIGS. 10-12. The poly-alcohol compound formation was confirmed at 3450 $cm^{-1}$. The ether compound and poly-ether alcohol compound formation were confirmed by peak signals from 1250-1040 $cm^{-1}$.

Extractability for evaluation of catalysts. Extractability method was established by Lubguban et al., J. Appl. Polymer Sci, 2009, 112(1):19-27) to evaluate the reactivity of the polyol products with polymeric MDI and a subsequent extraction test to determine the percentage of the unreacted oil phase. Low extractability is believed to correlate with high crosslinking, whereas high extractability is believed to correlate with the presence of nonfunctional or single-functional components in the B-side (alcohol side) of the urethane formulation. Extractability method was used to evaluate the effect of different catalysts added in epoxidized soybean oil. The mass percentage of extracted oil phase in the elastomeric wafer reflects the degree of crosslinking in the samples brought about by the catalysts. Relatively, a lower extractable content value indicates higher crosslinking and better catalyst performance. Table 30 shows the extractability values of samples using different catalysts.

TABLE 30

Catalysts evaluation by extractable content method. A sample elastomeric wafer was a mixture of 50% pMDI and 0.5% by weight catalyst in ESBO cured at 140° C./24 h in a convection oven.

| Sample | Catalyst Used | Extracted Oil Phase, % |
|---|---|---|
| CONTROL | None | 16.0 |
| 1 | $K_2HPO_4$ | 17.2 |
| 2 | Tin(II) 2-Ethylhexanoate | 10.0 |
| 3 | Triethanolamine | 15.1 |
| 4 | o-Phosphoric acid | 2.85 |
| 5 | Glycerol | 15.6 |
| 6 | DABCO 8154 | 21.1 |
| 7 | Polycat SA-1 | 22.6 |
| 8 | DABCO BL-17 | 21.6 |
| 9 | Propylamine | 18.9 |
| 10 | Propionamide | 17.9 |
| 11 | Octadecanamide | 19.5 |
| 12 | N-methyl-N-nitroso-p-toluenesulfonamide (Diazald) | 14.0 |
| 13 | N-Bromo-succinimide | 15.4 |
| 14 | N,N-Dimethylformamide | 15.9 |
| 15 | $KH_2PO_4$ | 14.4 |
| 16 | Calcium carbonate | 15.1 |
| 17 | n-Butanol | 15.6 |
| 18 | Methanol | 16.2 |
| 19 | Methanol + Sulfuric acid | 17.0 |
| 20 | Perfluoric acid-PTF prepolymer | 13.8 |
| 21 | Cobalt acetate | 15.2 |
| 22 | Phthalic acid | 13.1 |
| 23 | Acetic acid | 19.8 |
| 24. | Formic acid | 11.3 |
| 25 | p-Toluenesulfonic acid | 11.0 |
| 26 | Titanocene Dichloride | 10.2 |

TABLE 30-continued

Catalysts evaluation by extractable content method. A sample elastomeric wafer was a mixture of 50% pMDI and 0.5% by weight catalyst in ESBO cured at 140° C./24 h in a convection oven.

| Sample | Catalyst Used | Extracted Oil Phase, % |
|---|---|---|
| 27 | 1-Naphthol-3,6-Disulfonic Acid Disodium Salt Hydrate | 12.7 |
| 28 | Phenylenediamine | 22.1 |
| 29 | Potassium hydroxide | 41.5 |
| 30 | Ammonium chloride | 16.1 |
| 31 | Sulfuric acid | 15.2 |

Figure 15:
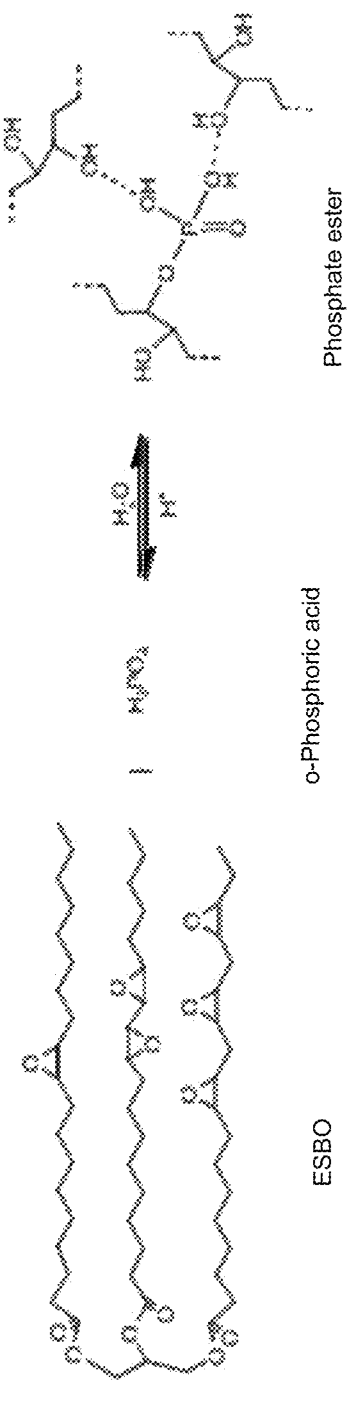
FIG. 15 presents a schematic representation of phosphate ester formation.

Mixing of epoxide and alcohol. Two mixing sequences were performed to investigate any changes in properties of the final ESP. In the first sequence, ESBO was made to react with o-$H_3PO_4$ separately before castor oil (CO) was added. The other sequence was performed by mixing ESBO, CO and o-$H_3PO_4$ simultaneously. All reactions were performed at room temperature. The schematic of this reaction is shown in FIG. 15. The chemical properties of the final ESPs are summarized in Table 31. From the determined results, we observed that there were no significant changes in the chemical properties of the final ESPs using different mixing sequences; therefore, the alcohol did not significantly interfere in the phosphate-epoxy ring reaction. Under the conditions of the reaction, the o-$H_3PO_4$ is believed to react directly with the oxirane group as shown in FIG. 15 causing an increase in viscosity and decrease in the oxirane oxygen concentration. There was only a slight increase in hydroxyl value as o-$H_3PO_4$ was increased for both sequences. This change was attributed to residual water coming from the aqueous o-$H_3PO_4$.

TABLE 31

Chemical properties of ESPs using two different mixing sequences. The Gardner color indices of the samples range from 1 to 3. All reacted samples composition: 1:1 by wt ESBO and CO.

| % o-$H_3PO_4$ based on ESBO | Acid Value, mg KOH/g (±0-5%) | Viscosity, cP (±0.2-1%) | % Oxirane Oxygen (±0.2-3%) | AOCS Hydroxyl Value, mg KOH/g (±2-4%) |
|---|---|---|---|---|
| Control | | | | |
| 0 | 1.54 | 434 | 3.44 | 84.10 |
| Separate | | | | |
| 0.5 | 1.75 | 501 | 3.22 | 84.30 |
| 1.0 | 1.65 | 665 | 3.12 | 89.56 |
| 2.0 | 1.63 | 1240 | 2.69 | 95.36 |
| Simultaneous | | | | |
| 0.5 | 1.90 | 507 | 3.30 | 87.70 |
| 1.0 | 1.80 | 660 | 3.04 | 89.30 |
| 2.0 | 1.90 | 1100 | 2.73 | 98.24 |

"Separate" indicates acid reaction was done first before alcohol addition while Simultaneous" indicates acid and alcohol reactions were done at the same time.

Figure 16:
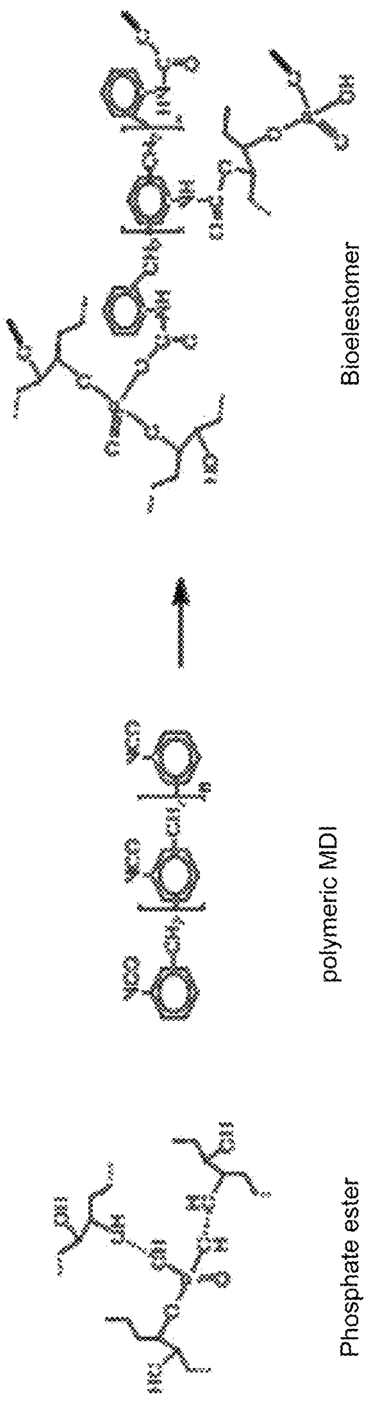
FIG. 16 depicts a schematic representation of urethane reaction.
Figure 17:
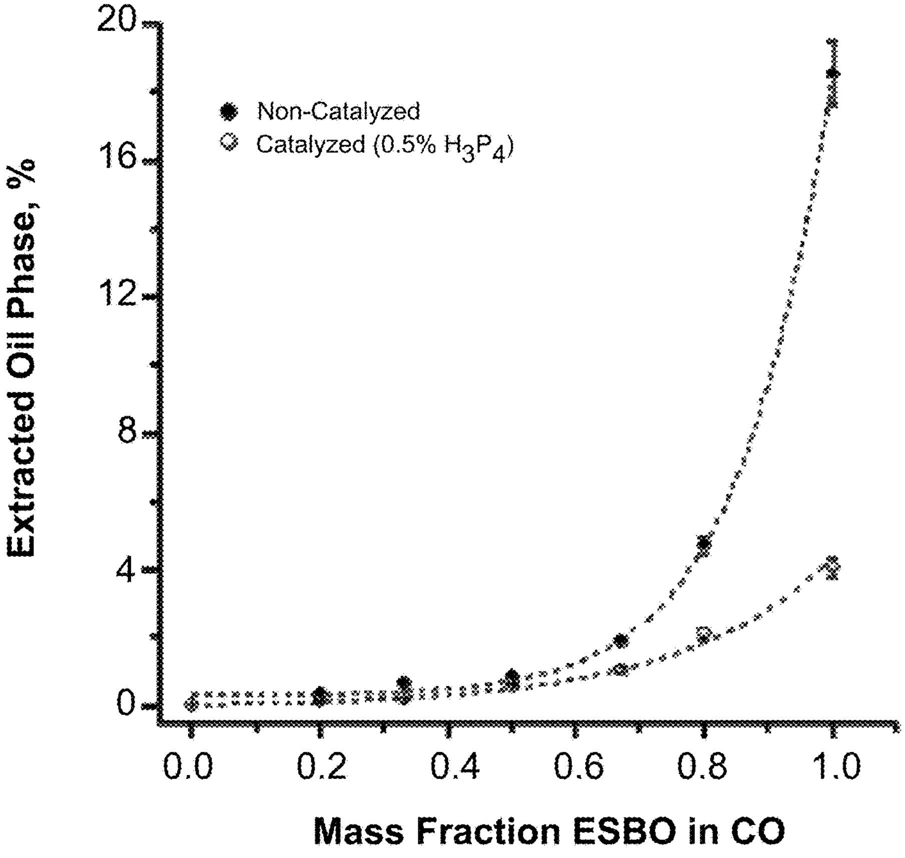
FIG. 17 illustrates the extractability trend of urethane elastomers based on catalyzed and non-catalyzed ESBO.
Figure 18:
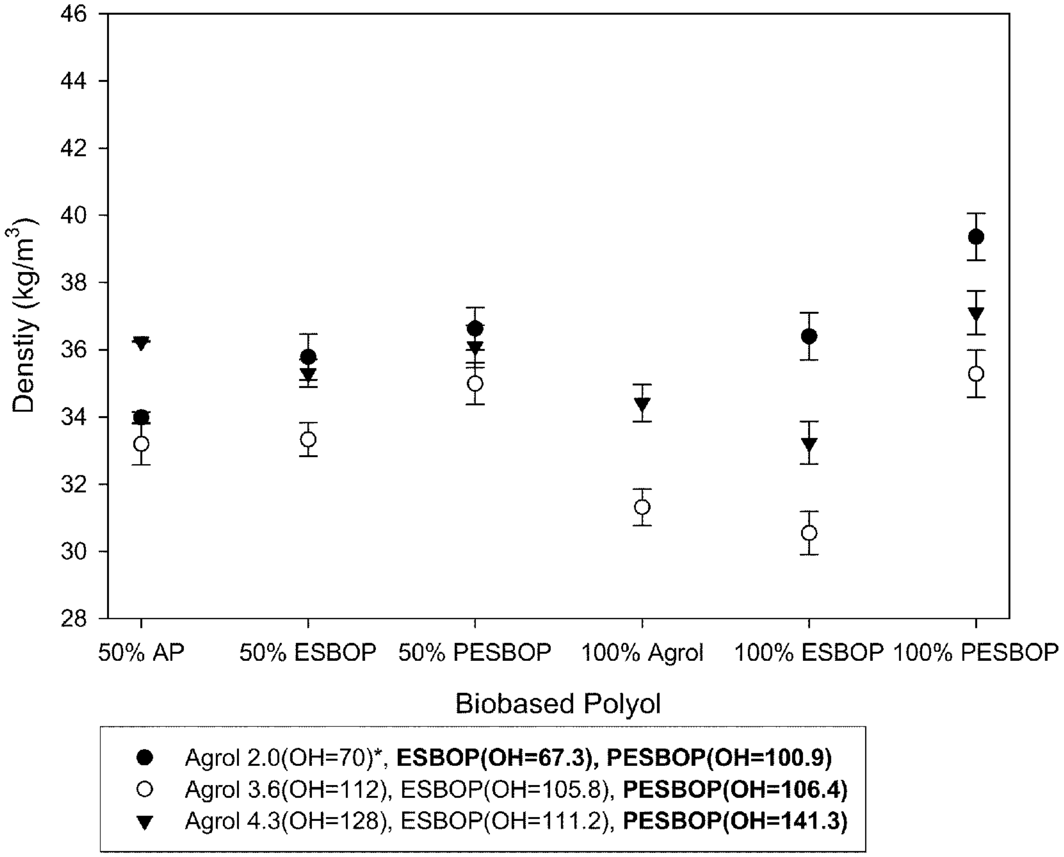
FIG. 18 presents the density of flexible polyurethane foams prepared from different biobased polyols and replacements. The foams made with Agrol 2.0(OH=70) collapsed, so there are no solid circle points at Agrol, 100%.
Figure 19:
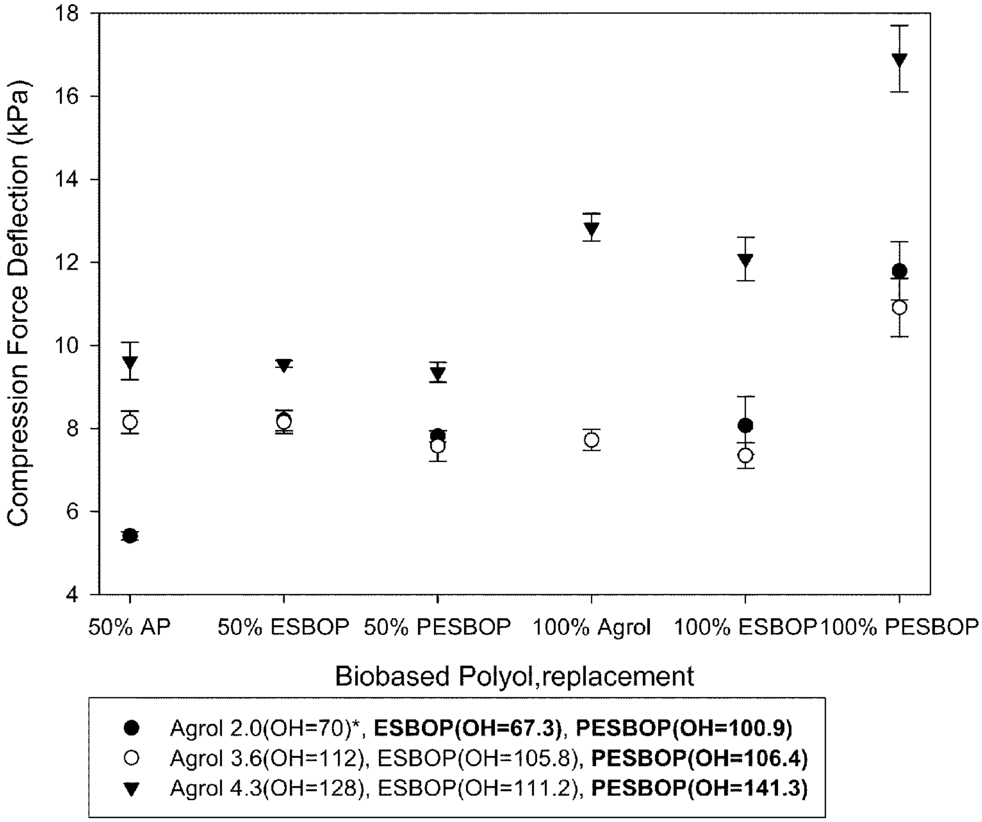
FIG. 19 depicts the compression force deflection of flexible polyurethane foams prepared from different biobased polyols and replacements. The foams made with Agrol 2.0(OH=70) collapsed, so there are no solid circle points at Agrol, 100%.
Figure 20:
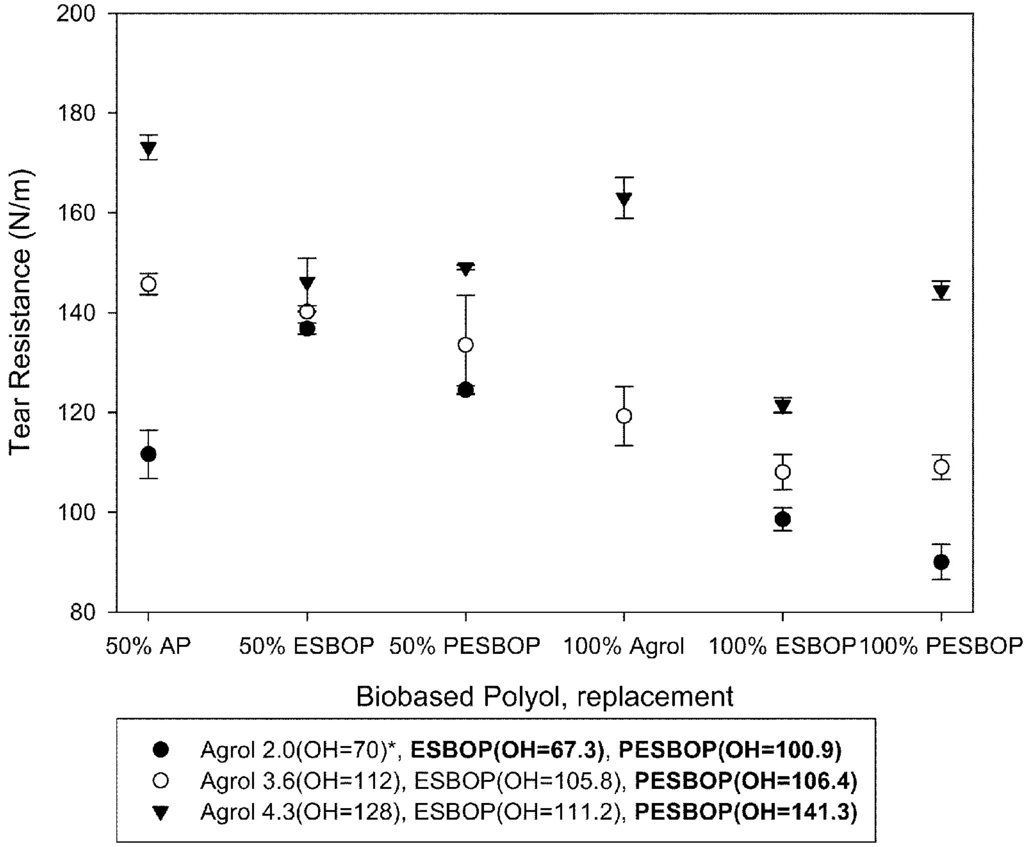
FIG. 20 presents the tear resistance of flexible polyurethane foams prepared from different biobased polyols and replacements. The foams made with Agrol 2.0(OH=70) collapsed, so there are no solid circle points at Agrol, 100%.
Figure 21:
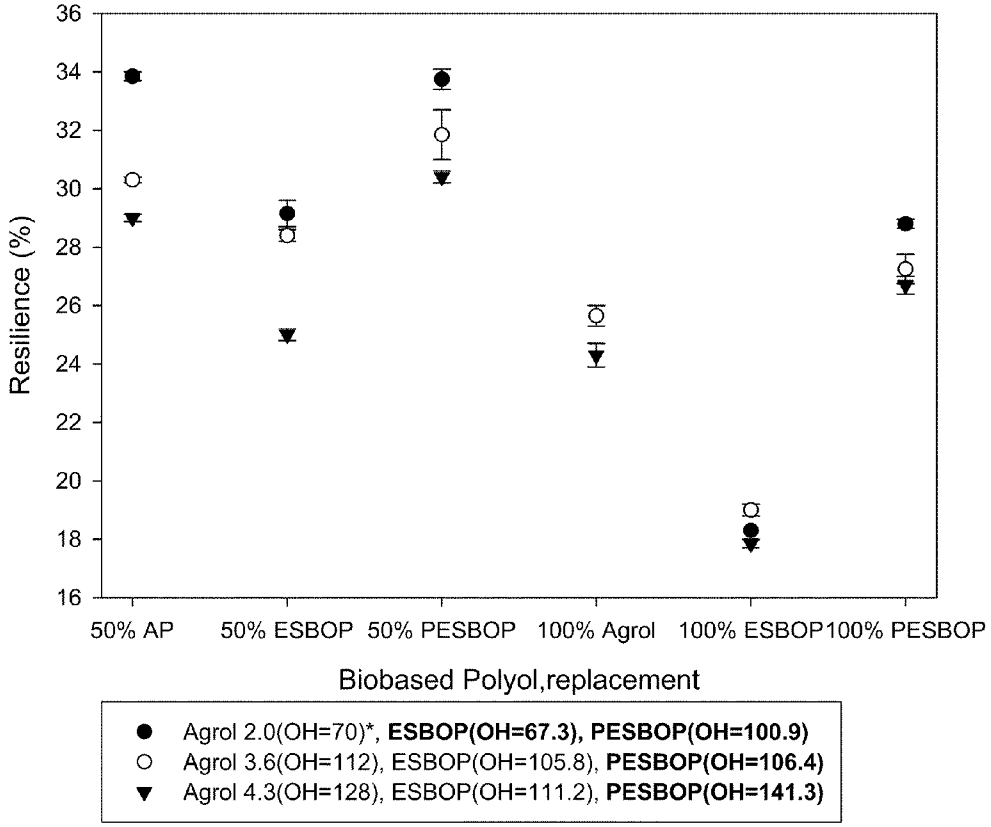
FIG. 21 depicts the resilience of flexible polyurethane foams prepared from different biobased polyols and replacements. The foams made with Agrol 2.0(OH=70) collapsed, so there are no solid circle points at Agrol, 100%.
Figure 22:
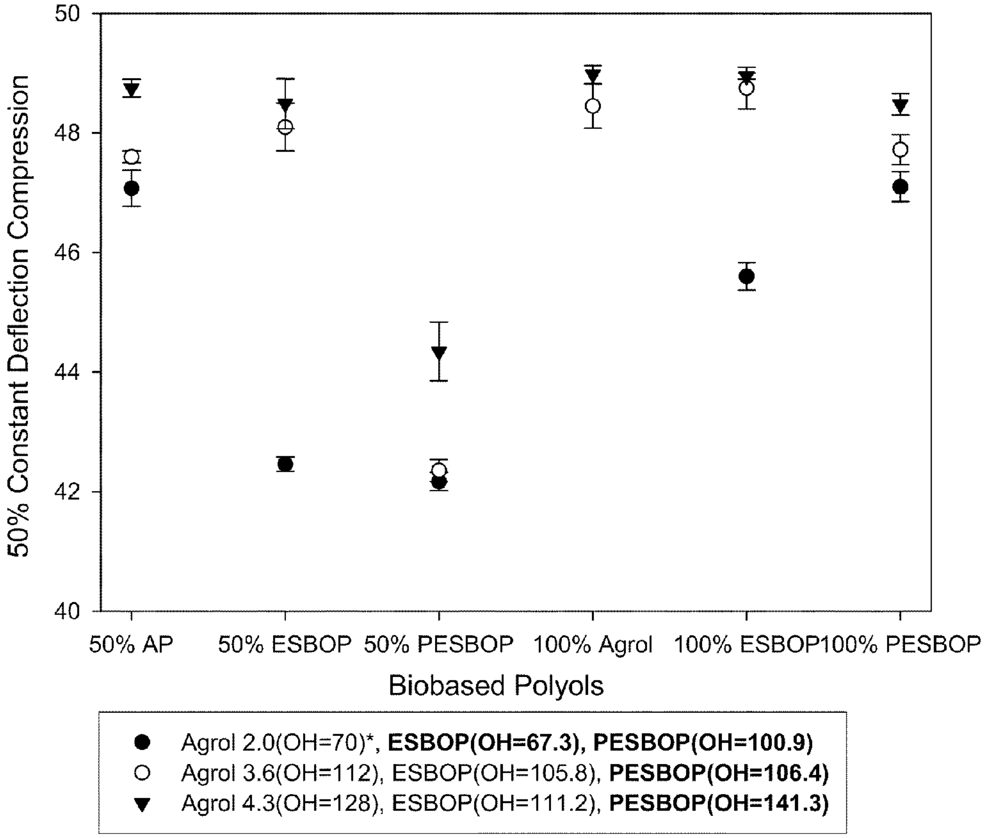
FIG. 22 presents 50% constant deflection compression of flexible polyurethane foams prepared from different biobased polyols and replacements. The foams made with Agrol 2.0 (OH=70) collapsed, so there are no solid circle points at Agrol, 100%.

Extractability for ESPs. The schematic representation of the reaction of ESP/phosphate esters with pMDI is shown in FIG. 16. For ESPs with higher alcohol concentration it is expected that the unreacted oil extractability is lower because the hydroxyl groups of castor oil readily react with the NCO functional group of pMDI forming crosslinked polymer macromolecules. The effect of catalysis and reaction of ESBO with o-$H_3PO_4$ is more pronounced at mass fractions between 0.5 to 1.0 ESBO in CO as shown in FIG. 17. With no alcohol loading an increase from 4.1% (catalyzed) to 18.6% (non-catalyzed) unreacted oil phase is observed which means that we can significantly increase the efficiency of ESP-pMDI reaction by o-$H_3PO_4$ catalysis. A lower alcohol loading can be compensated by increasing the average functionality (increase the hydroxyl equivalent weights at the same hydroxyl number) of the ESP which was achieved by epoxy reaction with o-$H_3PO_4$.

Acid-catalyzed epoxide. A second batch of urethane bioelastomers were prepared by reacting ESBO with o-$H_3PO_4$ without solvent or alcohol source as mentioned in the Experimental section. Table 32 presents the chemical properties of these samples with untreated ESBO as control. A significant reduction of about 25% oxirane oxygen content was observed upon reacting ESBO with 1.5% phosphoric acid. Gel point was observed at about 2.0% acid loading. This was verified by a more intense FTIR peak for untreated ESBO sample compared with acid-treated sample at wavenumber 824 $cm^{-1}$, characteristic of an epoxy signal. A steep increase in viscosity was also observed from 362 cP for untreated ESBO to about 4000 cP for the 1.5% acid-treated sample. This was indicative of the formation of phosphate esters which was verified by FTIR spectral intensity at wavenumber 1020 $cm^{-1}$. This characteristic signal was not at all observed with the untreated ESBO sample. The acid number did not increase significantly with increasing phosphoric acid loading. As mentioned, higher residual acidity is an undesirable polyol property as it competes with hydroxyls to react with isocyanates and consumes catalysts when these samples are further processed to produce bioelastomers and urethane foams. The increase in AOCS hydroxyl values from 11.0 to 38.4 was attributed wholly to the residual water that came from the aqueous o-$H_3PO_4$.

TABLE 32

Chemical properties of o-$H_3PO_4$-reacted ESBO (at RT) without solvent or alcohol source.

| Sample Code | % o-H3PO4 based on ESBO | Acid Value, mg KOH/g (±0-5%) | % Oxirane Oxygen (±0.2-3%) | AOCS Hydroxyl Value, mg KOH/g (±2-4%) | ASTM Hydroxyl Value, mg KOH/g (±0.3-5%) | Viscosity, cP (±0.2-1%) |
|---|---|---|---|---|---|---|
| Control | 0 | <0.20 | 7.06 | 11.0 | 404 | 362 |
| A | 0.5 | 0.77 | 6.77 | 23.0 | — | 559 |
| B | 1.0 | 0.89 | 6.30 | 32.2 | — | 1020 |
| C | 1.5 | 0.95 | 5.34 | 38.4 | 240 | 3950 |

Bioelastomer formation. Physicochemical properties of bioelastomers synthesized from treated epoxides in Table 32 are presented in Table 33. The general trend shows that comparatively, the higher mass percentage pMDI added to the acid-treated epoxides will yield better tensile properties. More epoxy-NCO and hydroxyl-NCO interactions are expected with higher isocyanate loading for samples with the same hydroxyl value. The more urethane bonds form the higher the degree of crosslinking between epoxide and isocyanate molecules resulting in a stronger three-dimensional polyurethane network. This translates to relatively stronger tensile properties of bioelastomers. Urethane bond signal was verified by FTIR spectra at wavenumber 3340 $cm^{-1}$ with a higher peak intensity observed with the bioelastomer synthesized from non-treated epoxide. This observation was consistent with epoxy and hydroxyl content of the starting epoxide. Higher epoxy/hydroxyl content translates to more epoxy-NCO and epoxy-hydroxyl interaction which form more urethane bonds. In the case of the acid-treated epoxide, lower epoxy content was measured due to ring-opening reaction brought about by acid catalysis.

TABLE 33

Tensile and thermal properties of bioelastomers from reacted epoxides of Table 26. Bioelastomers were evaluated at 15% and 25% by weight pMDI based on treated ESBO.

| Sample Code | Description | Strength at Break, MPa | Strain at Break, % | Young's Modulus, MPa | $T_g$ (DSC), ° C. |
|---|---|---|---|---|---|
| 15A | A + 15% pMDI | Not Applicable, material too soft | | | −10.2 |
| 15B | B + 15% pMDI | 0.295 | 4.32 | 0.221 | −13.8 |
| 15C | C + 15% pMDI | 0.416 | 5.10 | 0.465 | −17.4 |
| 25A | A + 25% pMDI | 0.940 | 9.00 | 0.462 | −11.5 |
| 25B | B + 25% pMDI | 1.32 | 5.93 | 0.949 | −15.9 |
| 25C | C + 25% pMDI | 1.47 | 5.13 | 2.044 | −18.4 |

A very important trend can be observed in relation to higher o-$H_3PO_4$ loading in ESBO and its effect on tensile properties of the resulting bioelastomers. From Table 33, at the same pMDI loading tensile properties increases with increasing the mass percentage of phosphoric acid added to ESBO. Also, at different pMDI loading taking samples 15C and 25A, the Young's Modulus of the two samples are comparatively similar which means that both samples have the same resistance to elastic deformation under load. For both cases, the preliminary catalysis of ESBO with o-$H_3PO_4$ formed the polymer network of phosphate esters which enhanced the strength of the macromolecule. More phosphate esters were formed in sample 15C than 25A, although upon addition of the A-side component, more NCO-epoxy interaction can be expected from 25A but the high concentration of phosphate esters in 15C is suggested to compensate the epoxy-isocyanate network. The $T_g$ values of the bioelastomers in Table 33 shows consistent trend, an increasing $T_g$ value as OH/NCO molar ratio increases. Each bioelastomer sample show only one glass transition temperature which reflects a high degree of phase mixing between the hard segment and the soft-segment domains.

In addition to the bioelastomer studies, our group has extensively evaluated bio-based polyols for rigid polyurethane foam using ESBO.[6] The ASTM hydroxyl value of the polyol is used in order to calculate the amount of isocyanate needed to react with the polyol. The catalyzed epoxide sample C in Table 32 shows an ASTM hydroxyl value of 240 mg KOH/g. The amount of isocyanate can be reduced to about 40% relative to the control with a hydroxyl value of 404 mg KOH/g. ESBO catalysis with o-$H_3PO_4$ presents the following advantages: enhanced polymer network, improved tensile properties and reduced pMDI loading for both urethane bioelastomer and rigid foaming formulations.

Example 14

The Properties of Soy-Based Flexible Polyurethane Foams

Figure 23:
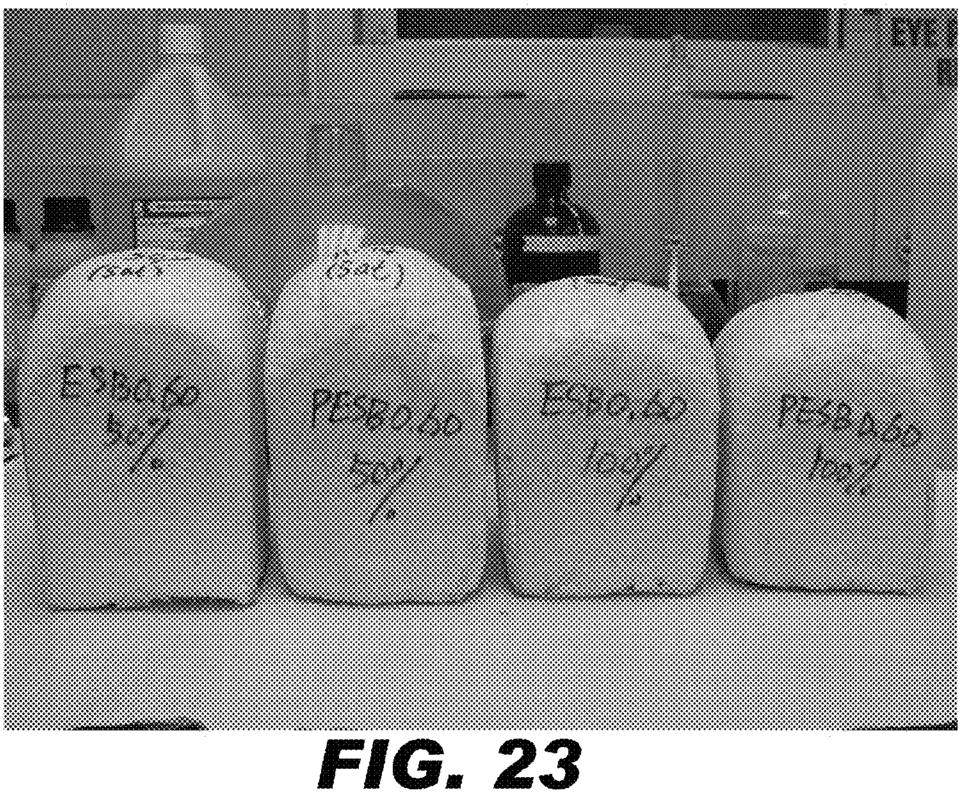
FIG. 23 presents images of flexible polyurethane foams prepared from 50% and 100% A1 and B1.
Figure 24:
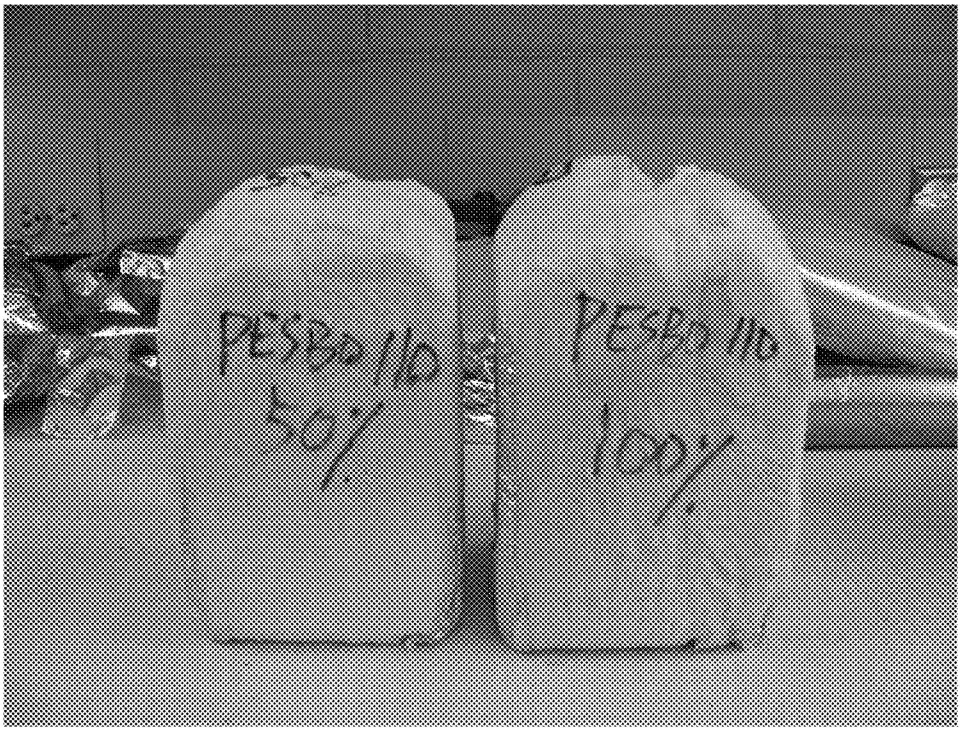
FIG. 24 presents images of flexible polyurethane foams prepared from 50% and 100% B3.

The viscosity and AOCS OH values of ESBO based polyols (ESBOPs) and PESBO based polyols (PESBOPs) after reheating are shown in Tables 34 and 35. They are summarized along with Agrol polyols in Table 36. The SBOPs marked in bold are reheated samples and their viscosities are all greater than 3000 cP after reheating. The properties of flexible polyurethane (PU) foams made of 50%, 100% various SBOPs are shown in FIGS. 18-22. Images of completed foams are shown in FIGS. 23 and 24

Figure 25:
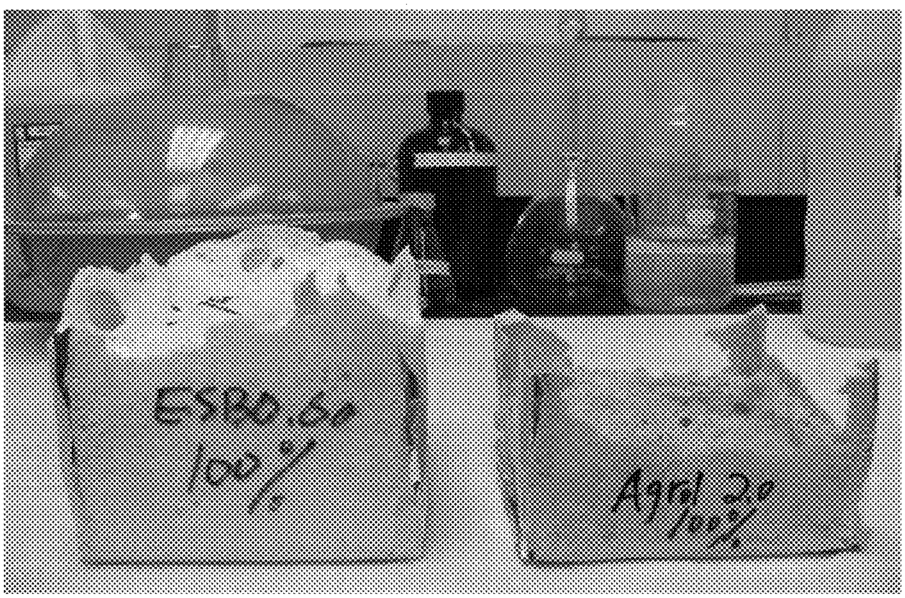
FIG. 25 presents images of flexible polyurethane foams prepared from 100% A1 and Agrol 2.0.

Increasing viscosity of SBOPs indeed improved the properties of flexible PU foams made of SBOPs. Compared to foams made from SBOPs before reheating, the foams made from reheated SBOPs displayed better flexibility, including higher resilience and lower constant deflection compression (CDC), due to an increase of viscosity. Also, foams made from PESBOPs showed better properties in resilience and CDC than foams made from Agrol polyols (APs). In addition, polyols with a higher viscosity helped build up the foam matrix. Foams made from ESBOP (OH=76.3, viscosity=4567) were successfully produced with 100% reheated ESBOP, while foams made from the same polyol (OH=72.7, viscosity=1111.1) before reheating totally collapsed (FIG. 25).

TABLE 34

| Polyols starting from ESBO (7% oxirane) | | | | |
|---|---|---|---|---|
| No. | OH Target | Sample | Viscosity [cP] | AOCS OH Value |
| A1 | 60 | ESBO:EG (1:0.4mr) + 0.5% pTSA (wt) | 4567 | 67.3 |
| A2a | 80 | ESBO:EG (1:0.8 mr) + 0.5% pTSA (wt) | 7345.6/ 10876/ 12520 | 105.8 |
| A2b | 80 | | 23188/ 29369.8/ 35806 | 127.2 |
| A3 | 110 | ESBO:EG (1:1 mr) + 0.5% pTSA (wt) | 8092.6/ 9433.5/ 9459.5 | 111.2-132.4 |
| A4 | 180 | ESBO:EG (1:2 mr) + 0.5% pTSA (wt) | 3801.7 | 210.9 (ASTM OH) |

TABLE 35

| Polyols Starting from PESBO (4.0% oxirane after removing water). | | | | |
|---|---|---|---|---|
| No. | OH Target | Sample | Viscosity [cP] | AOCS OH Value |
| B1 | 60 | PESBO:EG (1:0.4mr) + 0.5% pTSA (wt) | 3142 | 100.9 |
| B2 | 80 | PESBO:EG (1:0.8 mr) + 0.5% pTSA (wt) | 3245.9 | 106.4 |
| B3a | 110 | PESBO:EG (1:1mr) + 0.5% pTSA (wt) | 3096.3 | 141.3 |
| B4 | 180 | PESBO:EG (1:3 mr) + 0.5% pTSA (wt) | 6503 | 154.4 (ASTM OH) |

TABLE 36

| Summary of various soybean oil-based polyols. | | | |
|---|---|---|---|
| | Agrol Polyols | | |
| | Agrol 2.0 | Agrol 3.6 | Agrol 4.3 |
| AOCS OH (mg KOH/g) | 70 | 112 | 128 |
| Viscosity [cP] | 201 | 610 | 1150 |
| Fully Epoxidized Soybean oil-based Polyols (ESBOP) | **ESBOP (OH = 67.3)** | ESBOP (OH = 105.8) | ESBOP (OH = 111.2) |
| AOCS OH (mg KOH/g) | 67.3 | 105.8 | 111.2-132.4 |
| Viscosity [cP] | 4567 | 7345.6-12520 | 7406.3-9459.5 |
| Partially Epoxidized | **PESBOP** | **PESBOP** | **PESBOP** |

TABLE 36-continued

| Summary of various soybean oil-based polyols. | | | |
|---|---|---|---|
| | Agrol Polyols | | |
| | Agrol 2.0 | Agrol 3.6 | Agrol 4.3 |
| Soybean oil-based Polyols (PESBOP) | **(OH = 100.9)** | **(OH = 106.4)** | **(OH = 141.3)** |
| AOCS OH (mg KOH/g) | 100.9 | 106.4 | 141.3 |
| Viscosity [cP] | 3142 | 3245.9 | 3096.3 |

What is claimed is:

1. A process for preparing an oligomeric polyol, the process comprising contacting an epoxidized triglyceride having a viscosity of about 3,000 to about 6,000 cP at 22° C. with a hydroxyl-containing reactant in the presence of an aromatic sulfonic acid to form the oligomeric polymer, the oligomeric polymer having a hydroxyl value of at least 100 mg KOH/g.

2. The process of claim 1, wherein the epoxidized triglyceride is derived from soybean oil, and wherein about 20% to 100% of the double bonds of the epoxidized triglyceride comprise an oxirane ring.

3. The process of claim 2, wherein about 60% to 90% of the double bonds of the epoxidized triglyceride comprise an oxirane ring.

4. The process of claim 2, wherein epoxidized triglyceride has an epoxy content of about 5% to about 6.5%.

5. The process of claim 1, wherein the epoxidized triglyceride has a viscosity of about 3,500 to about 4,500 cP at 22° C.

6. The process of claim 1, wherein the hydroxyl-containing reactant is chosen from an alcohol and a diacid.

7. The process of claim 6, wherein the alcohol is a diol chosen from ethylene glycol, propylene glycol, diethylene glycol, triethylene glycol, and tetraethylene glycol.

8. The process of claim 1, wherein the aromatic sulfonic acid is chosen from p-toluenesulfonic acid and benzenesulfonic acid.

9. The process of claim 1, wherein the molar ratio of the epoxidized triglyceride to the hydroxyl-containing reagent to the aromatic sulfonic acid is about 1:0.1:0.005 to about 1:3:0.2; and the process is conducted at a temperature of about 100° C. to about 240° C.

10. The process of claim 1, wherein the hydroxyl-containing reactant is ethylene glycol; the aromatic sulfonic acid is p-toluenesulfonic acid; the molar ratio of epoxidized triglyceride to ethylene glycol to p-toluenesulfonic acid is about 1:0.4:0.02 to about 1:0.8:0.05; and the process is conducted at a temperature of about 130° C. to about 160° C.

* * * * *